(12) United States Patent
Ates et al.

(10) Patent No.: US 9,067,930 B2
(45) Date of Patent: Jun. 30, 2015

(54) 2-OXO-PIPERIDINYL DERIVATIVES

(71) Applicant: UCB Pharma, S.A., Brussels (BE)

(72) Inventors: Ali Ates, Brussels (BE); Florian Montel, Brussels (BE); Anne Valade, Brussels (BE); Olivier Lorthioir, Brussels (BE)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 14/350,534

(22) PCT Filed: Oct. 10, 2012

(86) PCT No.: PCT/EP2012/070000
§ 371 (c)(1),
(2) Date: Apr. 8, 2014

(87) PCT Pub. No.: WO2013/053725
PCT Pub. Date: Apr. 18, 2013

(65) Prior Publication Data
US 2015/0011526 A1    Jan. 8, 2015

(30) Foreign Application Priority Data

Oct. 11, 2011    (EP) .................................... 11184578

(51) Int. Cl.
| | | |
|---|---|---|
| *C07D 417/14* | (2006.01) |
| *C07D 401/14* | (2006.01) |
| *C07D 405/14* | (2006.01) |
| *C07D 413/14* | (2006.01) |
| *C07D 401/10* | (2006.01) |

(52) U.S. Cl.
CPC ............ *C07D 417/14* (2013.01); *C07D 401/14* (2013.01); *C07D 405/14* (2013.01); *C07D 413/14* (2013.01); *C07D 401/10* (2013.01)

(58) Field of Classification Search
CPC ...................................................... C07D 417/14
USPC ....................................... 546/188; 514/210.2
See application file for complete search history.

(56) References Cited

FOREIGN PATENT DOCUMENTS

EP        1997807 A1     12/2008

*Primary Examiner* — John Mabry
(74) *Attorney, Agent, or Firm* — McDonnell Boehen Hulbert & Berghoff LLP

(57) ABSTRACT

The present invention relates to 2-oxo-piperidinyl derivatives, processes for preparing them, pharmaceutical compositions containing them and their use as pharmaceuticals.

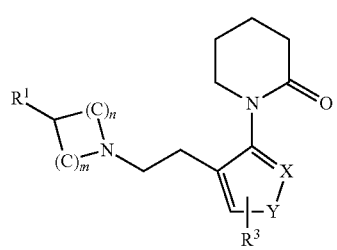

(I)

11 Claims, No Drawings

2-OXO-PIPERIDINYL DERIVATIVES

This application is a US national phase of International Application No. PCT/EP2012/070000 filed on Oct. 10, 2012, which claims priority to European Patent Application No. 11184578.0 filed on Oct. 11, 2011.

INTRODUCTION

The present invention relates to 2-oxo-piperidinyl derivatives, their preparation as well as their use in the treatment of migraine.

Migraine, with a prevalence of ±10% in the general population, is ranked as one of the most debilitating diseases by the WHO and represents a significant burden on society in terms of indirect costs due to losses in revenues. In the European community, 600,000 workdays/day are missed by migraine sufferers. Migraine is grossly under-diagnosed and under-treated. There are two types of treatment: acute treatment seeks to abort an ongoing migraine headache and preventive or prophylactic treatment aims to diminish the frequency and severity of headache episodes. Acute and prophylactic treatments are usually prescribed by general practitioners and specialists, respectively. The benchmarks for acute and preventive treatments are the triptans and topiramate, respectively. Both approaches have clear unmet medical needs in terms of efficacy (overall only 50 to 65% of patients are relieved by these treatments) and side-effects (experienced by 40-50% of patients).

Migraine headache results from cranial blood vessel vasodilatation, associated with exacerbated neuronal activity of the trigeminal complex, leading to peripheral sensitization (neurogenic inflammation accompanied by release of CGRP, a potent vasodilatator) and subsequently central sensitization (hyper-responsiveness of neurons in the trigeminal nucleus caudalis leading to increased transmission of pain signals). The mechanism of action of current acute treatments is largely focused on counteracting vasodilatation (e.g., all triptans are $5\text{-HT}_{1B/D/E/F}$ agonists inducing vasoconstriction; CGRP antagonists are also approved for acute therapy, having shown efficacy comparable to the triptans, while NO inhibitors are being evaluated in clinical trials). Common analgesics are poorly efficacious in migraine. Mechanisms of action for preventive treatments include raising the threshold to migraine activation, enhancing anti-nociception, inhibiting cortical spreading depression (a phenomenon preceding headache and consisting of a wave of neural hyperactivity followed by neural depression; this wave moves across the brain at a speed about 2-3 mm/min and is speculated to underlie the aura experienced by 30% of migraineurs), inhibiting peripheral and central sensitization, blocking neurogenic inflammation and modulating sympathetic, parasympathetic or serotoninergic tones. Topiramate, valproate and beta-adrenergic antagonists are the oral drugs approved by the FDA for the prophylactic treatment of migraine. These have been joined over the last year by cranial intramuscular injections of onabotulinumtoxin A (Botox®). Other drugs are used off-label and include 5-HT antagonists ($5\text{-HT}_2$, poorly selective), calcium antagonists and antidepressants (none are active in acute migraine treatment).

Migraine, depression and sleep disorders are characterized by a dysfunction in serotonin levels and transmission. They share patterns of rhythmicity in their occurrence and are often associated as co-morbidities, suggesting partially common underlying mechanisms. Literature evidence demonstrates that $5\text{-HT}_7$ antagonists have promising efficacy in pre-clinical models of depression (Wesolowska et al., Effect of the selective $5\text{-HT}_7$ receptor antagonist SB 269970 in animal models of anxiety and depression, Neuropharmacology, 2006, 51 578-586) and sleep disorders (Shelton et al. "$5\text{-HT}_7$ receptor deletion enhances REM sleep suppression induced by selective serotonin reuptake inhibitors, but not by direct stimulation of $5\text{-HT}_{1A}$ receptor" Neuropharmacology 2009, 56, 448-454).

$5\text{-HT}_7$ receptors belong to the large family of serotonin receptors composed of 14 members. $5\text{-HT}_7$ receptors are distributed in the central nervous system where they are highly expressed in the brainstem, the hypothalamus, thalamus and hippocampus. In the periphery, high levels are detected in the intestine and arteries, while much lower levels are measured in the heart. Pre-clinical experiments with SB-269970, a purportedly selective $5\text{-HT}_7$ antagonist, and knock-out data show convincing evidence for the involvement of $5\text{-HT}_7$ receptors in mood, sleep and circadian rhythm regulation (Shelton et al. "$5\text{-HT}_7$ receptor deletion enhances REM sleep suppression induced by selective serotonin reuptake inhibitors, but not by direct stimulation of $5\text{-HT}_{1A}$ receptor" Neuropharmacology 2009, 56 448-454). $5\text{-HT}_7$ receptors have also clearly been demonstrated to induce vasodilatation of blood vessels including cerebral arteries (Terron, J. A., Br J Pharmacol, 1997, 121:563-571 "Role of $5\text{-HT}_7$ receptors in the long lasting hypotensive response induced by 5-hydroxytryptamine in the rat"). Vasodilatation of cerebral blood vessels is an early event in the cascade leading to migraine headaches. Therefore, inhibition of serotonin-induced vasodilatation by $5\text{-HT}_7$ antagonists is expected to bring pain relief in migraine. These observations led Terron to formulate an original hypothesis about the potential roles of $5\text{-HT}_7$ receptors in migraine ((Terron, J. A., 2002, Eur. J. Pharmacol., 439:1-1 1 "Is the 5-HT7 receptor involved in the pathogenesis and prophylactic treatment of migraine?").

$5\text{-HT}_7$ antagonists are expected to have efficacy in the prophylactic (and potentially acute) treatment of migraine by:
1) Preventing serotonin-induced vasodilatation of cranial blood vessels (Matthys, A., et al., Role of the $5\text{-HT}_7$ receptor in the central nervous system: from current status to future perspectives. Molecular Neurobiology, 2011; Leopoldo, M., et al., Serotonin $5\text{-HT}_7$ receptor agents: Structure-activity relationships and potential therapeutic applications in central nervous system disorders. Pharmacology & Therapeutics, 2011, 129, 120-148; Hedlund, P. B., The $5\text{-HT}_7$ receptor and disorders of the nervous system: an overview. Psychopharmacology, 2009, 206, 345-354). Contrary to the triptans, $5\text{-HT}_7$ antagonists would only reverse a pre-existing vasodilatation, without producing vasoconstriction by themselves. This would make $5\text{-HT}_7$ antagonists, in contrast to triptans, compatible with chronic use and therefore with prophylactic treatment.
2) By inhibiting peripheral and central sensitization. Inhibition of neurogenic inflammation by SB-269970, a reference $5\text{-HT}_7$ receptor antagonist and by our most advanced compounds has been observed in the plasma protein extravasation (PPE) model of migraine. In this rat model of migraine, dural protein extravasation is induced by electrical stimulation of the trigeminal ganglion. $5\text{-HT}_7$ antagonists were as efficacious as sumatriptan and topiramate in reducing protein extravasation. Additionally, a recent study showed that SB-269970 inhibits the release of CGRP after electrical stimulation of the trigeminal ganglion (Wang et al., "Selective Inhibition of $5\text{-HT}_7$ Receptor Reduces CGRP Release in an Experimental Model for Migraine", Headache, 2010, 50, 579-587), lending further support to the potential efficacy of $5\text{-HT}_7$ antagonists in treating migraine.

Although the triptans have been shown to reduce peripheral and central sensitization as well as counteracting vasodilatation, their chronic use for prophylactic treatment is precluded by their cardiovascular side-effects, due mainly to their active vasoconstriction. 5-HT$_7$ antagonists do not actively provoke vasoconstriction but prevent vasodilatation and should not suffer from the same limitation as the triptans during chronic administration (an internal study has shown that SB-269970 does not induce human coronary artery contraction; sumatriptan used as a comparator did). Topiramate, the current standard of care, as well as the other drugs used for prophylaxis treatment suffer from side-effects and limited efficacy. Side effects with topiramate are severe enough to provoke high drop-out rates (25-30%) in clinical trials. In addition, topiramate is not effective against acute migraine. From current pre-clinical data, selective 5-HT$_7$ antagonists are not expected to have the side-effects seen with most of the current prophylactic drugs. We don't know at this stage if they could be more efficacious, but we anticipate that they could also be active in the acute treatment of migraine. In addition, the pre-clinical data showing activity of 5-HT$_7$ antagonists in depression models and in modulating sleep patterns indicate that there is a potential to treat two common migraine co-morbidities.

Antagonists of 5-HT$_7$ receptors, in particular for the treatment of migraine, have been disclosed in WO 2009/029439 and in WO 2009/048765.

It has been an objective of the present invention to provide 5-HT$_7$ receptor antagonists, preferably selective 5-HT$_7$ receptor antagonists. A further objective was to provide a new form for the treatment of migraine.

SUMMARY OF THE INVENTION

The invention provides new 2-oxo-piperidinyl derivatives, their preparation as well as their use in the treatment of migraine. Further aspects of the invention will become apparent from the detailed description.

DETAILED DESCRIPTION OF THE INVENTION

The present invention relates to 2-oxo-piperidinyl derivatives according to formula I,

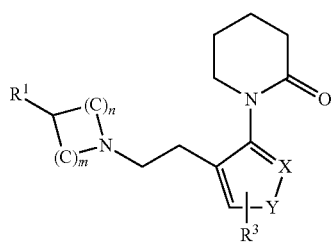

(I)

wherein
X is either CH or N;
Y is either —NR$^4$— or —CH═CH—, however with the proviso that X shall be N when Y is —NR$^4$—; whereby R$^4$ is either hydrogen or a C$_{1-4}$ alkyl.
n is an integer selected from 1, 2 or 3; m is 1 or 2;
R$^1$ is selected from the group comprising or consisting of a substituted or unsubstituted C$_{1-6}$ alkyl, a substituted or unsubstituted aryl, a substituted or unsubstituted heterocycle, a substituted or unsubstituted C$_{3-8}$ cycloalkyl; or R$^1$ is a —O—R$^2$ moiety, whereby R$^2$ is selected from the group comprising or consisting of a substituted or unsubstituted C$_{1-6}$ alkyl, a substituted or unsubstituted aryl or a substituted or unsubstituted heteroaryl.

R$^3$ is hydrogen, substituted or unsubstituted C$_{1-4}$ alkyl or halogen.

The present invention relates in particular to 2-oxo-piperidinyl derivatives according to formula I-A,

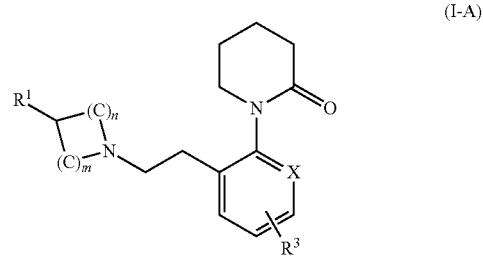

(I-A)

wherein
X is either CH or N;
n is an integer selected from 1, 2 or 3; m is 1 or 2;
R$^1$ is selected from the group comprising or consisting of a substituted or unsubstituted C$_{1-6}$ alkyl, a substituted or unsubstituted aryl, a substituted or unsubstituted heterocycle, a substituted or unsubstituted C$_{3-8}$ cycloalkyl; or R$^1$ is a —O—R$^2$ moiety, wherein R$^2$ is selected from the group comprising or consisting of a substituted or unsubstituted C$_{1-6}$ alkyl, a substituted or unsubstituted aryl or a substituted or unsubstituted heteroaryl; and
R$^3$ is hydrogen, substituted or unsubstituted C$_{1-4}$ alkyl or halogen.

In one embodiment of the formula I-A, X is CH. In a further embodiment X is N.

The present invention relates also to 2-oxo-piperidinyl derivatives according to formula I-B,

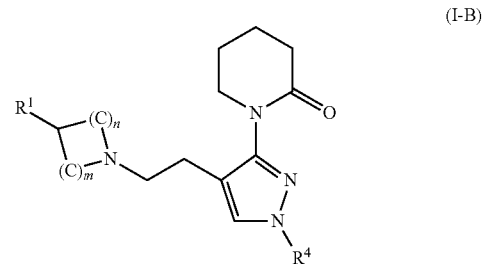

(I-B)

wherein
n is an integer selected from 1, 2 or 3; m is 1 or 2;
R$^1$ is selected from the group comprising or consisting of a substituted or unsubstituted C$_{1-6}$ alkyl, a substituted or unsubstituted aryl, a substituted or unsubstituted heterocycle, a substituted or unsubstituted C$_{3-8}$ cycloalkyl; or R$^1$ is a —O—R$^2$ moiety, wherein R$^2$ is selected from the group comprising or consisting of a substituted or unsubstituted C$_{1-6}$ alkyl, a substituted or unsubstituted aryl or a substituted or unsubstituted heteroaryl; and
R$^4$ is hydrogen or C$_{1-4}$ alkyl, preferably methyl.

In one embodiment m is 1. In a further embodiment, n is 1, in another n is 2, and in another it is 3.

In one embodiment of any of formulae I, I-A or I-B, R$^1$ or R$^2$ may be substituted by one, two or more halogens, or a C$_{1-6}$ alkyl, C$_{1-4}$ alkoxy, cyano, amido, acyl, hydroxy, or an aryl, an heteroaryl, a heterocycloalkyl, which in their turn may optionally be substituted with from 1 to 5 substituents selected from the group consisting of C$_{1-6}$ alkyl, C$_{2-6}$ alkenyl, C$_{2-6}$ alkynyl, cycloalkyl, heterocycloalkyl, amino, aryl, heteroaryl, alkoxy, halogen, cyano, hydroxy, amido.

In a further specific embodiment, R$^1$ of formulae I, I-A or I-B, is a substituted or unsubstituted C$_{1-4}$ alkyl.

In a further specific embodiment, R¹ is selected from the group comprising or consisting of a substituted or unsubstituted C₁₋₄ alkyl, a substituted or unsubstituted phenyl, a substituted or unsubstituted pyridinyl, a substituted or unsubstituted pyrimidinyl, a substituted or unsubstituted thiazolyl, a substituted or unsubstituted piperidinyl, a substituted or unsubstituted tetrahydropyranyl, a substituted or unsubstituted tetrahydrofuranyl, a substituted or unsubstituted cyclohexyl; or R¹ is a —O—R² moiety.

In another specific embodiment, R¹ is benzyl, 2-bromobenzyl, tert-butyl, 2-methylpropyl, 2-fluoro-2-methylpropyl, 2-chloro-2,2-difluoroethyl, 2-oxo-2-(pyrrolidin-1-yl)ethyl, 2,2,2-trifluoroethyl, propyl, phenyl, 2-carbamoylphenyl, 2-chlorophenyl, 3-chlorophenyl, 4-chlorophenyl, 2-cyanophenyl, 3-cyanophenyl, 4-cyanophenyl, 3,4-difluorophenyl, 2-fluorophenyl, 3-fluorophenyl, 4-fluorophenyl, 2-hydroxyphenyl, 2-methoxyphenyl, 3-methoxyphenyl, 4-methoxyphenyl, 2-(methylcarbamoyl)phenyl, 2-(3-methyl-1,2,4-oxadiazol-5-yl)phenyl, 2-(pyrrolidin-1-ylcarbonyl)phenyl, 2-(trifluoromethyl)phenyl, 3-(trifluoromethyl)phenyl, 4-(trifluoromethyl)phenyl, cyclohexyl, 4,4-difluorocyclohexyl, pyridin-2-yl, 6-cyanopyridin-2-yl, 3-fluoropyridin-2-yl, 5-fluoropyridin-2-yl, 6-methoxypyridin-2-yl, 6-methylpyridin-2-yl, 6-(4-fluorophenyl)pyridin-2-yl, 6-(propan-2-yloxy)pyridin-2-yl, 6-(1H-pyrazol-1-yl)pyridin-2-yl, 6-trifluoromethylpyridin-2-yl, 6-(cyclo-butyloxy)pyridin-2-yl, 6-(difluoromethoxy)pyridin-2-yl, 6-(2,2,2-trifluoroethoxy)pyridin-2-yl, pyridin-3-yl, 2-fluoropyridin-3-yl, pyridin-4-yl, 4-methoxypyrimidin-2-yl, 4-methyl-1,3-thiazol-2-yl, 4-methyl-1,3-thiazol-5-yl, 1-acetylpiperidin-2-yl, tetrahydro-2H-pyran-3-yl, tetrahydro-2H-pyran-4-yl, tetrahydrofuran-2-yl; or R¹ is a —O—R² moiety.

In one embodiment, R² of formulae I, I-A or I-B is selected from the group comprising or consisting of a substituted or unsubstituted C₁₋₄-alkyl, or a substituted or unsubstituted aryl, or a substituted or unsubstituted heteroaryl.

In another specific embodiment of formulae I, I-A or I-B, R² is selected from the group comprising or consisting of a substituted or unsubstituted benzyl, a substituted or unsubstituted phenyl, or a substituted or unsubstituted pyridinyl; preferably a benzyl or a substituted or unsubstituted phenyl.

In a further specific embodiment of formulae I, I-A or I-B, R² is benzyl, phenyl, 5-bromo-2-methoxyphenyl, 2-cyanophenyl, 3-cyanophenyl, 4-cyanophenyl, 2-fluorophenyl, 4-fluorophenyl, 2-methoxy-phenyl, 3-methoxyphenyl or 5-fluoropyridin-2-yl.

In one specific embodiment, R³ is hydrogen, fluorine or trifluoromethyl.

In one specific embodiment, R⁴ is methyl.

In a further specific embodiment, the present invention relates to 2-oxo-piperidinyl derivatives according to formula I-C, (I-C)

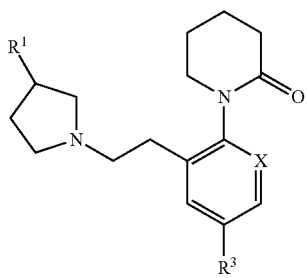

wherein
X is either CH or N;
R¹ is selected from the group comprising or consisting of a substituted or unsubstituted C₁₋₄ alkyl, a substituted or unsubstituted aryl, a substituted or unsubstituted heteroaryl, a substituted or unsubstituted heterocycloalkyl, a substituted or unsubstituted C₃₋₆ cycloalkyl; or R¹ is a —O—R² moiety, wherein R² is selected from the group comprising or consisting of a substituted or unsubstituted C₁₋₄-alkyl aryl, a substituted or unsubstituted aryl, or a substituted or unsubstituted heteroaryl; and R³ is hydrogen, substituted or unsubstituted C₁₋₄ alkyl or halogen.

In another particular embodiment, R¹ in compounds of formula I-C is benzyl, 2-methylpropyl, 2,2,2-trifluoroethyl, propyl, phenyl, 2-carbamoylphenyl, 2-chlorophenyl, 3-chlorophenyl, 4-chlorophenyl, 2-cyanophenyl, 3-cyanophenyl, 4-cyanophenyl, 3,4-difluorophenyl, 2-fluorophenyl, 3-fluorophenyl, 4-fluorophenyl, 2-hydroxyphenyl, 2-methoxyphenyl, 3-methoxyphenyl, 4-methoxyphenyl, 2-(methylcarbamoyl)phenyl, 2-(3-methyl-1,2,4-oxadiazol-5-yl)phenyl, 2-(pyrrolidin-1-ylcarbonyl)phenyl, 2-(trifluoromethyl)-phenyl, 3-(trifluoromethyl)phenyl, 4-(trifluoromethyl)phenyl, cyclohexyl, 4,4-difluorocyclohexyl, pyridin-2-yl, 6-cyanopyridin-2-yl, 3-fluoropyridin-2-yl, 6-methoxypyridin-2-yl, 6-methylpyridin-2-yl, 6-(4-fluorophenyl)pyridin-2-yl, 6-(propan-2-yloxy)pyridin-2-yl, 6-(1H-pyrazol-1-yl)pyridin-2-yl, 6-trifluoromethylpyridin-2-yl, 6-(cyclobutyloxy)pyridin-2-yl, 6-(2,2,2-trifluoroethoxy)pyridin-2-yl, 6-(difluoromethoxy)pyridin-2-yl, pyridin-4-yl, 4-methoxypyrimidin-2-yl, 4-methyl-1,3-thiazol-2-yl, 4-methyl-1,3-thiazol-5-yl; or R¹ is a group of formula —OR² wherein R² is 4-cyanophenyl.

In a preferred embodiment, R¹ in compounds of formula I-C is phenyl, 2-carbamoylphenyl, 2-chlorophenyl, 3-chlorophenyl, 4-chlorophenyl, 2-cyanophenyl, 4-cyanophenyl, 3,4-difluorophenyl, 2-fluorophenyl, 3-fluorophenyl, 4-fluorophenyl, 2-hydroxyphenyl, 2-methoxyphenyl, 3-methoxyphenyl, 4-methoxyphenyl, 2-(3-methyl-1,2,4-oxadiazol-5-yl)phenyl, 2-(trifluoromethyl)phenyl, cyclohexyl, 6-cyanopyridin-2-yl, 3-fluoropyridin-2-yl, 6-methoxypyridin-2-yl, 6-(propan-2-yloxy)pyridin-2-yl, 6-(cyclobutyloxy)pyridin-2-yl, 6-(2,2,2-trifluoroethoxy)pyridin-2-yl, 6-(difluoromethoxy)pyridin-2-yl, 4-methyl-1,3-thiazol-2-yl.

In another preferred embodiment, R¹ in compounds of formula I-C is phenyl, 4-cyanophenyl, 2-fluorophenyl, 4-fluorophenyl, 2-hydroxyphenyl, cyclohexyl, 6-methoxypyridin-2-yl, 6-(propan-2-yloxy)pyridin-2-yl or 6-(cyclobutyloxy)pyridin-2-yl.

In a preferred embodiment, R³ in compounds of formula I-C is hydrogen, fluorine or trifluoromethyl. More preferably R³ in compounds of formula I-C is hydrogen or trifluoromethyl, most preferably hydrogen.

In still a further specific embodiment, the present invention relates to 2-oxo-piperidinyl derivatives according to formula I-D, (I-D)

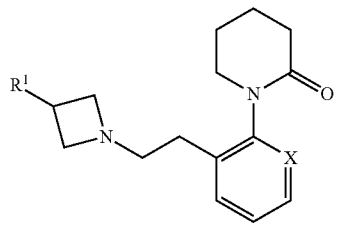

wherein
X is either CH or N;
R¹ is selected from the group comprising or consisting of a substituted or unsubstituted C₁₋₄ alkyl, a substituted or unsubstituted aryl, a substituted or unsubstituted heteroaryl, a substituted or unsubstituted heterocycloalkyl, a substituted or unsubstituted C$_{3-6}$ cycloalkyl; or R$^1$ is a —O—R$^2$ moiety, wherein R$^2$ is selected from the group comprising or consisting of a substituted or unsubstituted C$_{1-4}$-alkyl aryl, a substituted or unsubstituted aryl, or a substituted or unsubstituted heteroaryl.

In another particular embodiment, R$^1$ in compounds of formula I-D is benzyl, 2-bromobenzyl, 3-cyanophenyl, 2-fluorophenyl, 2-methoxyphenyl, 3-methoxyphenyl; or R$^1$ is a group of formula —OR$^2$ wherein R$^2$ is phenyl, 5-bromo-2-methoxyphenyl, 2-cyanophenyl, 2-fluorophenyl or 4-fluorophenyl.

In a preferred embodiment, R$^1$ in compounds of formula I-D is 2-bromobenzyl, 2-methoxyphenyl; or R$^1$ is a group of formula —OR$^2$ wherein R$^2$ is 5-bromo-2-methoxy-phenyl or 4-fluorophenyl.

In another preferred embodiment, R$^1$ in compounds of formula I-D is 2-bromobenzyl or a group of formula —OR$^2$ wherein R$^2$ is 5-bromo-2-methoxyphenyl.

In still another particular embodiment, the present invention relates to 2-oxo-piperidinyl derivatives according to formula I-E,

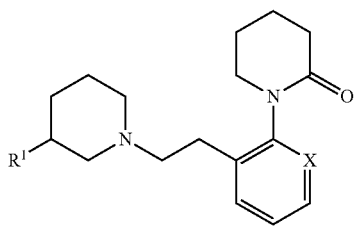

(I-E)

wherein

X is either CH or N;

R$^1$ is selected from the group comprising or consisting of a substituted or unsubstituted C$_{1-4}$ alkyl, a substituted or unsubstituted phenyl, a substituted or unsubstituted pyridinyl, a substituted or unsubstituted pyrimidinyl, a substituted or unsubstituted thiazolyl, a substituted or unsubstituted piperidinyl, a substituted or unsubstituted tetrahydropyranyl, a substituted or unsubstituted tetrahydrofuranyl, a substituted or unsubstituted cyclohexyl; or R$^1$ is a —O—R$^2$ moiety, wherein R$^2$ is a substituted or unsubstituted benzyl, a substituted or unsubstituted phenyl, or a substituted or unsubstituted pyridinyl; preferably a benzyl or a substituted or unsubstituted phenyl.

In another particular embodiment, R$^1$ in compounds of formula I-E is phenyl, 2-carbamoylphenyl, 4-cyanophenyl or 2-methoxyphenyl, preferably 2-methoxyphenyl.

Also comprised are tautomers, geometrical isomers, enantiomers, diastereomers and mixtures, or a pharmaceutically acceptable salt of compounds of formula I, I-A, I-B, I-C, I-D and I-E, as well as any deuterated variant, at any position. Any moiety "H" in formula I, I-A, I-B, I-C, I-D and I-E may be the isotope hydrogen, deuterium or tritium.

Specific compounds of the present invention are those selected from the group consisting of:
(+)-2-(1-{2-[2-(2-oxopiperidin-1-yl)phenyl]ethyl}pyrrolidin-3-yl)benzamide oxalate;
N-methyl-2-(1-{2-[2-(2-oxopiperidin-1-yl)phenyl]ethyl}pyrrolidin-3-yl)benzamide oxalate;
2-(1-{2-[2-(2-oxopiperidin-1-yl)phenyl]ethyl}pyrrolidin-3-yl)benzonitrile oxalate;
2-(1-{2-[2-(2-oxopiperidin-1-yl)phenyl]ethyl}piperidin-3-yl)benzamide oxalate;
1-[2-(2-{3-[2-(trifluoromethyl)phenyl]pyrrolidin-1-yl}ethyl)phenyl]piperidin-2-one oxalate;
1-(2-{2-[3-(2-methoxyphenyl)pyrrolidin-1-yl]ethyl}phenyl)piperidin-2-one oxalate;
1-(2-{2-[3-(3-methoxyphenyl)pyrrolidin-1-yl]ethyl}phenyl)piperidin-2-one oxalate;
1-(2-{2-[3-(4-methoxyphenyl)pyrrolidin-1-yl]ethyl}phenyl)piperidin-2-one oxalate;
1-(2-{2-[3-(2-fluorophenyl)pyrrolidin-1-yl]ethyl}phenyl)piperidin-2-one oxalate;
1-(2-{2-[3-(2-chlorophenyl)pyrrolidin-1-yl]ethyl}phenyl)piperidin-2-one oxalate;
1-[2-(2-{3-[2-(3-methyl-1,2,4-oxadiazol-5-yl)phenyl]pyrrolidin-1-yl}ethyl)phenyl]piperidin-2-one;
(+)-2-(1-{2-[2-(2-oxopiperidin-1-yl)phenyl]ethyl}pyrrolidin-3-yl)benzonitrile oxalate;
(−)-2-(1-{2-[2-(2-oxopiperidin-1-yl)phenyl]ethyl}pyrrolidin-3-yl)benzonitrile oxalate;
1-{2-[2-(3-phenylpyrrolidin-1-yl)ethyl]phenyl}piperidin-2-one;
3-(1-{2-[2-(2-oxopiperidin-1-yl)phenyl]ethyl}pyrrolidin-3-yl)benzonitrile oxalate;
4-(1-{2-[2-(2-oxopiperidin-1-yl)phenyl]ethyl}pyrrolidin-3-yl)benzonitrile oxalate;
(−)-1-[2-(2-{3-[2-(pyrrolidin-1-ylcarbonyl)phenyl]pyrrolidin-1-yl}ethyl)phenyl]piperidin-2-one;
1-(2-{2-[3-(2-methoxyphenyl)piperidin-1-yl]ethyl}phenyl)piperidin-2-one oxalate;
(+)-1-(2-{2-[3-(2-methoxyphenyl)pyrrolidin-1-yl]ethyl}phenyl)piperidin-2-one oxalate;
(−)-1-(2-{2-[3-(2-methoxyphenyl)pyrrolidin-1-yl]ethyl}phenyl)piperidin-2-one oxalate;
1-[2-(2-{3-[3-(trifluoromethyl)phenyl]pyrrolidin-1-yl}ethyl)phenyl]piperidin-2-one oxalate;
1-(2-{2-[3-(3-fluorophenyl)pyrrolidin-1-yl]ethyl}phenyl)piperidin-2-one oxalate;
1-{2-[2-(3-phenylazetidin-1-yl)ethyl]phenyl}piperidin-2-one oxalate;
1-(2-{2-[3-(3-fluorophenyl)piperidin-1-yl]ethyl}phenyl)piperidin-2-one oxalate;
1-(2-{2-[3-(3-methoxyphenyl)piperidin-1-yl]ethyl}phenyl)piperidin-2-one oxalate;
1-{2-[2-(3-phenylpiperidin-1-yl)ethyl]phenyl}piperidin-2-one oxalate;
1-(2-{2-[3-(4-chlorophenyl)pyrrolidin-1-yl]ethyl}phenyl)piperidin-2-one oxalate;
1-(2-{2-[3-(3-chlorophenyl)pyrrolidin-1-yl]ethyl}phenyl)piperidin-2-one oxalate;
1-(2-{2-[3-(benzyloxy)pyrrolidin-1-yl]ethyl}phenyl)piperidin-2-one oxalate;
1-(2-{2-[3-(4-fluorophenyl)azetidin-1-yl]ethyl}phenyl)piperidin-2-one oxalate;
3-(1-{2-[2-(2-oxopiperidin-1-yl)phenyl]ethyl}azetidin-3-yl)benzonitrile oxalate;
1-(2-{2-[3-(2-fluorophenyl)azetidin-1-yl]ethyl}phenyl)piperidin-2-one oxalate;
1-{2-[2-(3-cyclohexylpyrrolidin-1-yl)ethyl]phenyl}piperidin-2-one oxalate;
1-(2-{2-[3-(2-hydroxyphenyl)pyrrolidin-1-yl]ethyl}phenyl)piperidin-2-one oxalate;
1-(2-{2-[3-(pyridin-2-yl)pyrrolidin-1-yl]ethyl}phenyl)piperidin-2-one dioxalate;
1-(2-{2-[3-(pyridin-2-yl)pyrrolidin-1-yl]ethyl}phenyl)piperidin-2-one;

1-(2-{2-[3-(4-fluorophenyl)pyrrolidin-1-yl]ethyl}phenyl)piperidin-2-one oxalate;
1-(2-{2-[(3R)-3-(2,2,2-trifluoroethyl)pyrrolidin-1-yl]ethyl}phenyl)piperidin-2-one oxalate;
1-(2-{2-[(3S)-3-(2,2,2-trifluoroethyl)pyrrolidin-1-yl]ethyl}phenyl)piperidin-2-one trifluoroacetate;
1-(2-{2-[(3S)-3-(2,2,2-trifluoroethyl)pyrrolidin-1-yl]ethyl}phenyl)piperidin-2-one oxalate;
4-(1-{2-[2-(2-oxopiperidin-1-yl)phenyl]ethyl}piperidin-3-yl)benzonitrile oxalate;
(−)-4-(1-{2-[2-(2-oxopiperidin-1-yl)phenyl]ethyl}pyrrolidin-3-yl)benzonitrile oxalate;
(+)-4-(1-{2-[2-(2-oxopiperidin-1-yl)phenyl]ethyl}pyrrolidin-3-yl)benzonitrile oxalate;
1-(2-{2-[3-(2-methoxyphenyl)azetidin-1-yl]ethyl}phenyl)piperidin-2-one oxalate;
1-(2-{2-[3-(3-fluorophenyl)azetidin-1-yl]ethyl}phenyl)piperidin-2-one oxalate;
1-(2-{2-[3-(3,4-difluorophenyl)pyrrolidin-1-yl]ethyl}phenyl)piperidin-2-one oxalate;
1-(2-{2-[3-(3-methoxyphenyl)azetidin-1-yl]ethyl}phenyl)piperidin-2-one oxalate;
1-{2-[2-(3-benzylpyrrolidin-1-yl)ethyl]phenyl}piperidin-2-one oxalate;
1-(2-{2-[3-(2-methoxyphenoxy)pyrrolidin-1-yl]ethyl}phenyl)piperidin-2-one oxalate;
4-[(1-{2-[2-(2-oxopiperidin-1-yl)phenyl]ethyl}pyrrolidin-3-yl)oxy]benzonitrile;
1-(2-{2-[3-(tetrahydro-2H-pyran-4-yl)pyrrolidin-1-yl]ethyl}phenyl)piperidin-2-one oxalate;
1-{2-[2-(3-benzylazetidin-1-yl)ethyl]phenyl}piperidin-2-one;
1-(2-{2-[3-(pyridin-3-yl)pyrrolidin-1-yl]ethyl}phenyl)piperidin-2-one;
1-(2-{2-[3-(4,4-difluorocyclohexyl)pyrrolidin-1-yl]ethyl}phenyl)piperidin-2-one trifluoroacetate;
4-[(1-{2-[2-(2-oxopiperidin-1-yl)phenyl]ethyl}azetidin-3-yl)oxy]benzonitrile oxalate;
1-(2-{2-[3-(2-methylpropyl)pyrrolidin-1-yl]ethyl}phenyl)piperidin-2-one trifluoroacetate;
1-{2-[2-(3-propyl pyrrolidin-1-yl)ethyl]phenyl}piperidin-2-one trifluoroacetate;
3-[(1-{2-[2-(2-oxopiperidin-1-yl)phenyl]ethyl}azetidin-3-yl)oxy]benzonitrile;
2-[(1-{2-[2-(2-oxopiperidin-1-yl)phenyl]ethyl}azetidin-3-yl)oxy]benzonitrile;
1-(2-{2-[3-(4-fluorophenoxy)azetidin-1-yl]ethyl}phenyl)piperidin-2-one;
1-(2-{2-[3-(3-methoxyphenoxy)azetidin-1-yl]ethyl}phenyl)piperidin-2-one;
1-(2-{2-[3-(2-bromobenzyl)azetidin-1-yl]ethyl}phenyl)piperidin-2-one;
4-(1-{2-[2-(2-oxopiperidin-1-yl)pyridin-3-yl]ethyl}pyrrolidin-3-yl)benzonitrile;
1-(2-{2-[3-(4-methyl-1,3-thiazol-5-yl)pyrrolidin-1-yl]ethyl}phenyl)piperidin-2-one;
1-(2-{2-[3-(5-bromo-2-methoxyphenoxy)azetidin-1-yl]ethyl}phenyl)piperidin-2-one oxalate;
1-{2-[2-(3-phenoxyazetidin-1-yl)ethyl]phenyl}piperidin-2-one oxalate;
1-{2-[2-(3-tert-butylpyrrolidin-1-yl)ethyl]phenyl}piperidin-2-one;
1-(2-{2-[3-(2-methoxyphenoxy)azetidin-1-yl]ethyl}phenyl)piperidin-2-one oxalate;
1-(2-{2-[3-(2-chloro-2,2-difluoroethyl)pyrrolidin-1-yl]ethyl}phenyl)piperidin-2-one;
1-(3-{2-[3-(pyridin-2-yl)pyrrolidin-1-yl]ethyl}pyridin-2-yl)piperidin-2-one;
1-(3-{2-[3-(pyridin-2-yl)pyrrolidin-1-yl]ethyl}pyridin-2-yl)piperidin-2-one oxalate;
1-(2-{2-[3-(1-acetylpiperidin-2-yl)pyrrolidin-1-yl]ethyl}phenyl)piperidin-2-one;
1-(2-{2-[3-(pyridin-4-yl)pyrrolidin-1-yl]ethyl}phenyl)piperidin-2-one;
1-(2-{2-[3-(2-fluoropyridin-3-yl)pyrrolidin-1-yl]ethyl}phenyl)piperidin-2-one;
1-(2-{2-[3-(tetrahydrofuran-2-yl)pyrrolidin-1-yl]ethyl}phenyl)piperidin-2-one;
1-(2-{2-[3-(tetrahydrofuran-2-yl)pyrrolidin-1-yl]ethyl}phenyl)piperidin-2-one oxalate;
(+)-1-(2-{2-[3-(tetrahydro-2H-pyran-4-yl)pyrrolidin-1-yl]ethyl}phenyl)piperidin-2-one trifluoroacetate;
(+)-1-(2-{2-[3-(tetrahydro-2H-pyran-4-yl)pyrrolidin-1-yl]ethyl}phenyl)piperidin-2-one oxalate;
1-(3-{2-[(3S)-3-(2,2,2-trifluoroethyl)pyrrolidin-1-yl]ethyl}pyridin-2-yl)piperidin-2-one oxalate;
1-(3-{2-[(3S)-3-(2,2,2-trifluoroethyl)pyrrolidin-1-yl]ethyl}pyridin-2-yl)piperidin-2-one;
1-(2-{2-[3-(tetrahydro-2H-pyran-3-yl)pyrrolidin-1-yl]ethyl}phenyl)piperidin-2-one trifluoroacetate;
1-(2-{2-[3-(6-methoxypyridin-2-yl)pyrrolidin-1-yl]ethyl}phenyl)piperidin-2-one;
1-(2-{2-[3-(5-fluoropyridin-2-yl)pyrrolidin-1-yl]ethyl}phenyl)piperidin-2-one;
1-(2-{2-[3-(3-fluoropyridin-2-yl)pyrrolidin-1-yl]ethyl}phenyl)piperidin-2-one;
1-(2-{2-[3-(2-fluoro-2-methylpropyl)pyrrolidin-1-yl]ethyl}phenyl)piperidin-2-one;
1-[2-(2-{3-[2-oxo-2-(pyrrolidin-1-yl)ethyl]pyrrolidin-1-yl}ethyl)phenyl]piperidin-2-one;
1-(2-{2-[3-(4-methyl-1,3-thiazol-2-yl)pyrrolidin-1-yl]ethyl}phenyl)piperidin-2-one oxalate;
1-(3-{2-[3-(5-fluoropyridin-2-yl)pyrrolidin-1-yl]ethyl}pyridin-2-yl)piperidin-2-one;
1-(3-{2-[3-(pyridin-2-yl)pyrrolidin-1-yl]ethyl}pyridin-2-yl)piperidin-2-one oxalate, isomer A;
(+)-1-(3-{2-[3-(4,4-difluorocyclohexyl)pyrrolidin-1-yl]ethyl}pyridin-2-yl)piperidin-2-one oxalate;
(−)-1-(3-{2-[3-(4,4-difluorocyclohexyl)pyrrolidin-1-yl]ethyl}pyridin-2-yl)piperidin-2-one oxalate;
1-(3-{2-[3-(6-methoxypyridin-2-yl)pyrrolidin-1-yl]ethyl}pyridin-2-yl)piperidin-2-one;
1-(3-{2-[3-(6-methoxypyridin-2-yl)pyrrolidin-1-yl]ethyl}pyridin-2-yl)piperidin-2-one oxalate;
1-[3-(2-{3-[6-(propan-2-yloxy)pyridin-2-yl]pyrrolidin-1-yl}ethyl)pyridin-2-yl]piperidin-2-one oxalate;
1-(3-{2-[(3R)-3-(2,2,2-trifluoroethyl)pyrrolidin-1-yl]ethyl}pyridin-2-yl)piperidin-2-one oxalate;
6-(1-{2-[2-(2-oxopiperidin-1-yl)pyridin-3-yl]ethyl}pyrrolidin-3-yl)pyridine-2-carbonitrile oxalate;
1-(3-{2-[3-(3-fluoropyridin-2-yl)pyrrolidin-1-yl]ethyl}pyridin-2-yl)piperidin-2-one oxalate;
1-[3-(2-{3-[6-(trifluoromethyl)pyridin-2-yl]pyrrolidin-1-yl}ethyl)pyridin-2-yl]piperidin-2-one;
1-[3-(2-{3-[(5-fluoropyridin-2-yl)oxy]azetidin-1-yl}ethyl)pyridin-2-yl]piperidin-2-one;
1-(3-{2-[3-(4-fluorophenoxy)azetidin-1-yl]ethyl}pyridin-2-yl)piperidin-2-one oxalate;
1-(3-{2-[3-(2-fluorophenoxy)azetidin-1-yl]ethyl}pyridin-2-yl)piperidin-2-one oxalate;
(−)-1-(3-{2-[3-(pyridin-2-yl)pyrrolidin-1-yl]ethyl}pyridin-2-yl)piperidin-2-one oxalate;

1-(3-{2-[3-(6-methylpyridin-2-yl)pyrrolidin-1-yl]
ethyl}pyridin-2-yl)piperidin-2-one;
1-[3-(2-{3-[6-(1H-pyrazol-1-yl)pyridin-2-yl]pyrrolidin-1-
yl}ethyl)pyridin-2-yl]piperidin-2-one oxalate;
1-(3-{2-[3-(4-methoxypyrimidin-2-yl)pyrrolidin-1-yl]
ethyl}pyridin-2-yl)piperidin-2-one;
1-[3-(2-{3-[6-(4-fluorophenyl)pyridin-2-yl]pyrrolidin-1-
yl}ethyl)pyridin-2-yl]piperidin-2-one;
1-[3-(2-{3-[6-(cyclobutyloxy)pyridin-2-yl]pyrrolidin-1-
yl}ethyl)pyridin-2-yl]piperidin-2-one oxalate;
1-[3-(2-{3-[6-(2,2,2-trifluoroethoxy)pyridin-2-yl]pyrroli-
din-1-yl}ethyl)pyridin-2-yl]piperidin-2-one;
1-[3-(2-{3-[6-(difluoromethoxy)pyridin-2-yl]pyrrolidin-1-
yl}ethyl)pyridin-2-yl]piperidin-2-one; 1-[3-{2-[3-(pyri-
din-2-yl)pyrrolidin-1-yl]ethyl}-5-(trifluoromethyl)pyri-
din-2-yl]piperidin-2-one:
1-[3-{2-[3-(pyridin-2-yl)pyrrolidin-1-yl]ethyl}-5-(trifluo-
romethyl)pyridin-2-yl]piperidin-2-one oxalate;
1-(5-fluoro-3-{2-[3-(pyridin-2-yl)pyrrolidin-1-yl]
ethyl}pyridin-2-yl)piperidin-2-one, as a mixture of (+)-1-
(5-fluoro-3-{2-[3-(pyridin-2-yl)pyrrolidin-1-yl]
ethyl}pyridin-2-yl)piperidin-2-one and (−)-1-(5-fluoro-3-
{2-[3-(pyridin-2-yl)pyrrolidin-1-yl]ethyl}pyridin-2-yl)
piperidin-2-one.

The following paragraphs provide definitions of the various chemical moieties that make up the compounds according to the invention and are intended to apply uniformly throughout the specification and claims unless an otherwise expressly set out definition provides a broader definition.

"$C_{1-6}$ alkyl" or "$C_{1-4}$ alkyl" refers to a group which represents saturated, monovalent hydrocarbon radicals having straight (unbranched) or branched moities or combinations thereof, and containing 1 to 6 carbon atoms, or 1 to 4 carbon atoms. Examples of $C_{1-4}$ alkyl groups are methyl, ethyl, n-propyl, isopropyl, n-butyl, isobutyl, tert-butyl. "$C_{1-4}$ alkyl" or "$C_{1-6}$ alkyl" groups may be substituted by one or more substituents selected from halogen, amido, aryl or alkoxy. Particular alkyl groups according to the present invention are methyl, difluoromethyl, trifluoromethyl, 2-chloro-2,2-difluoroethyl, 2,2,2-trifluoroethyl, propyl, 2-methylpropyl, 2-fluoro-2-methylpropyl, tert-butyl, 2-oxo-2-(pyrrolidin-1-yl)ethyl, benzyl and 2-bromobenzyl.

"Alkoxy" refers to the group —O—R where R includes "$C_{1-4}$ alkyl". Examples of alkoxy groups according to the present invention are methoxy, difluoromethoxy, 2,2,2-trifluoroethoxy, propan-2-yloxy, and cyclobutoxy.

"$C_{3-8}$ cycloalkyl" refers to a saturated carbocyclic group of from 3 to 8 carbon atoms having a single ring (e.g., cyclohexyl) or multiple condensed rings (e.g., norbornyl). Cycloalkyl include cyclopropyl, cyclobutyl, cyclopentyl, cyclohexyl, and the like. Examples of aryl groups according to the present invention are cyclobutyl, cyclohexyl, and 4,4-difluorocyclohexyl.

"Aryl" refers to an unsaturated aromatic carbocyclic group of from 6 to 14 carbon atoms having a single ring (e.g., phenyl) or multiple condensed rings (e.g., naphthyl). The "aryl" groups may be unsubstituted or substituted by 1 to 3 substituents independently selected from $C_{1-4}$ alkyl, $C_{1-4}$ alkoxy, halogen, cyano, amido, hydroxy or heterocycle. Aryl include phenyl and the like. Examples of aryl groups according to the present invention are phenyl, 2-bromophenyl, 5-bromo-2-methoxyphenyl, 2-carbamoylphenyl, 2-chlorophenyl, 3-chlorophenyl, 4-chlorophenyl, 2-cyanophenyl, 3-cyanophenyl, 4-cyanophenyl, 3,4-difluorophenyl, 2-fluorophenyl, 3-fluorophenyl, 4-fluorophenyl, 2-hydroxyphenyl, 2-methoxyphenyl, 3-methoxyphenyl, 4-methoxyphenyl, 2-(methylcarbamoyl)phenyl, 2-(3-methyl-1,2,4-oxadiazol-5-yl)phenyl, 2-(pyrrolidin-1-ylcarbonyl)phenyl, 2-(trifluoromethyl)phenyl, and 3-(trifluoromethyl)phenyl.

$C_{1-4}$-alkyl aryl refers to a $C_{1-4}$ alkyl having an aryl substituent as defined hereabove. Examples of $C_{1-4}$-alkyl aryl groups according to the present invention are benzyl and 2-bromobenzyl.

"Heterocycle" refers to a saturated or unsaturated ring system containing, in addition to carbon atoms, at least one hetero atom, such as nitrogen, oxygen and/or sulfur. "Heterocycle" includes both "heteroaryl" and "heterocycloalkyl".

"Heteroaryl" refers to a monocyclic heteroaromatic, or a bicyclic or a tricyclic fused-ring heteroaromatic group. Particular examples of heteroaromatic groups include optionally substituted pyridyl, pyrimidinyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl, imidazopyrimidine, imidazopyridazine, imidazothiazole, imidazothiadiazole, preferably pyridyl, pyrimidynyl, oxazolyl, thiazolyl, pyrazolyl and 1,2,4-oxadiazolyl. Examples of heteroaryl groups according to the present invention are pyridin-2-yl, 1-acetylpiperidin-2-yl, 3-fluoropyridin-2-yl, 5-fluoropyridin-2-yl, 6-cyanopyridin-2-yl, 6-(trifluoromethyl)pyridin-2-yl, 6-methylpyridin-2-yl, 6-methoxypyridin-2-yl, 6-(propan-2-yloxy)pyridin-2-yl, 6-(4-fluorophenyl)pyridin-2-yl, 6-(cyclobutoxy)pyridin-2-yl, 6-(difluoromethoxy)pyridin-2-yl, 6-(2,2,2-trifluoroethoxy)pyridin-2-yl, 6-(1H-pyrazol-1-yl)pyridin-2-yl, pyridin-3-yl, 2-fluoropyridin-3-yl, pyridin-4-yl, 3-methyl-1,2,4-oxadiazol-5-yl, 4-methyl-1,3-thiazol-2-yl, 4-methyl-1,3-thiazol-5-yl, 1H-pyrazol-1-yl, and 4-methoxypyrimidin-2-yl.

"Heterocycloalkyl" refers to a $C_{3-8}$ cycloalkyl group according to the definition above, in which 1 to 3 carbon atoms are replaced by hetero atoms chosen from the group consisting of O, S, NR, R being defined as hydrogen, acyl or $C_{1-6}$ alkyl. Preferred heterocycloalkyl include pyrrolidinyl, piperidinyl, piperazinyl, 1-acetylpiperazinyl, 1-methylpiperazinyl, morpholinyl, tetrahydropyranyl, tetrahydrofuranyl, and the like. Examples of heterocycloalkyl groups according to the present invention are pyrrolidin-1-yl, tetrahydro-2H-pyran-4-yl, tetrahydro-2H-pyran-3-yl and tetrahydrofuran-2-yl.

"$C_{2-6}$ alkenyl" refers to alkenyl groups preferably having from 2 to 6 carbon atoms and having at least 1 or 2 sites of alkenyl unsaturation. Preferable alkenyl groups include ethenyl (vinyl, —CH=$CH_2$), n-2-propenyl (allyl, —$CH_2$CH=$CH_2$) and the like.

"$C_{2-6}$ alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Amido" refers to the group C(=O)NRR' where each R, R' is independently hydrogen, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", and where R and R', together with the nitrogen atom to which they are attached, can optionally form a 3-8-membered heterocycloalkyl ring. Examples of amido groups according to the present invention are carbamoyl, methylcarbamoyl and pyrrolidin-1-ylcarbonyl.

"Amino" refers to the group NRR' where each R, R' is independently hydrogen, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", and where R and R', together with the nitrogen atom to which they are attached, can optionally form a 3-8-membered heterocycloalkyl ring.

"Halogen" refers to fluoro, chloro, bromo and iodo atoms.

"Cyano" refers to —CN.

"Acyl" refers to the group —C(=O)R where R is "$C_{1-6}$ alkyl", "$C_{2-6}$ alkenyl", "$C_{2-6}$ alkynyl", "$C_{3-8}$ cycloalkyl", "heterocycloalkyl", "aryl" or "heteroaryl". Example of acyl group according to the present invention is acetyl.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_{1-6}$ alkyl" or "$C_{1-4}$ alkyl", "$C_{2-6}$ alkenyl", "$C_{2-6}$ alkynyl", "cycloalkyl", "heterocycloalkyl", "amino", "aryl", "heteroaryl", "alkoxy", "halogen", cyano, hydroxy, mercapto, nitro, "amido", "acyl", and the like.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, oxalic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Compounds of formula I and some of their intermediates may have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

In one embodiment, the compounds of formula (I) show a good affinity for the 5-$HT_7$ receptor. Such property may be determined with methods known to a person skilled in the art, including the one set out in example 20.

In one embodiment of the present invention, the compounds of formula (I) are antagonists of 5-$HT_7$, i.e. they inhibit the activity of 5-$HT_7$ agonists. Such property may be determined with methods known to a person skilled in the art, including the one set out in example 21.

In further embodiment of the present invention, some compounds of formula (I) have a high selectivity ratio ranging from 10 to 1000 or more for 5-$HT_7$ receptors compared to other serotonin receptor subtypes.

The compounds of formula I according to the invention can be prepared analogously to conventional methods as understood by the person skilled in the art of synthetic organic chemistry.

According to one embodiment, some compounds of general formula I may be prepared by reaction of an amine of formula II (or a corresponding salt) with an aldehyde of formula III according to the equation:

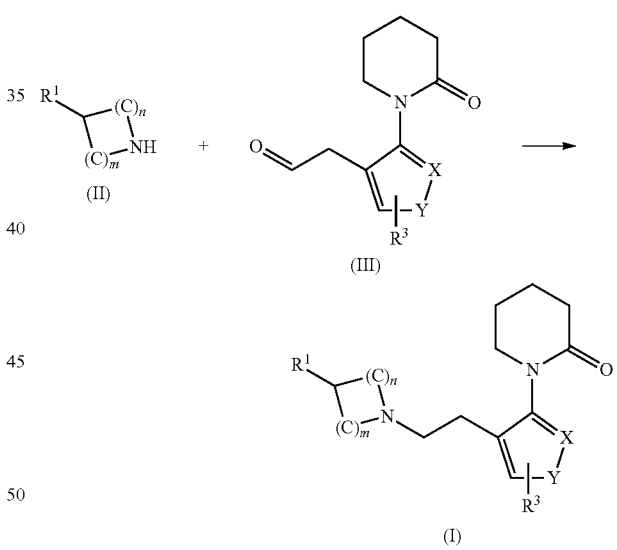

wherein X, Y, m, n, $R^1$ and $R^3$ have the same definitions as defined above for compounds of formula I.

This reductive amination may be carried out in an alcohol such as methanol, in the presence of an acid such as acetic acid and of a mild reducing agent such as sodium cyanoborohydride, at a temperature comprise between 0° C. and room temperature, or according to any other method known to the person skilled in the art.

According to another embodiment, some compounds of formula I-A wherein X is C, $R^3$ is hydrogen, m=1 and n=2 or 3 may be prepared by reaction of an amine of formula II (or a corresponding salt) with an alkylating agent such as a tosylate of formula IV according to the equation:

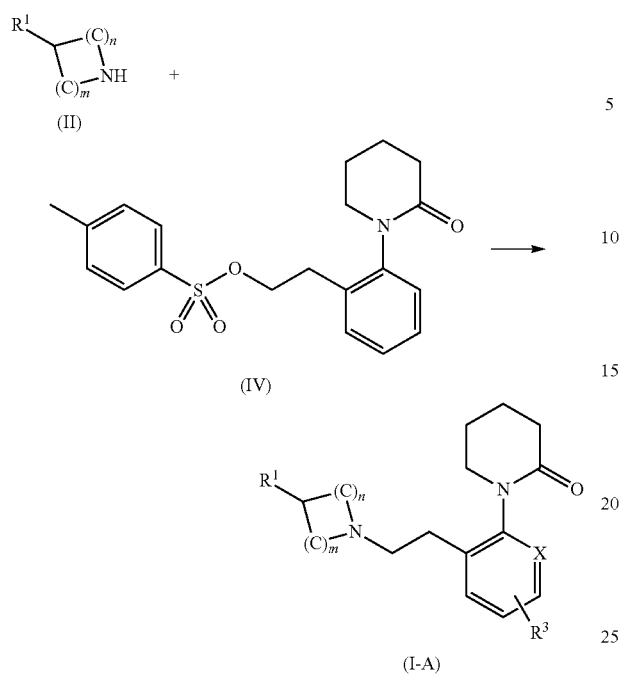

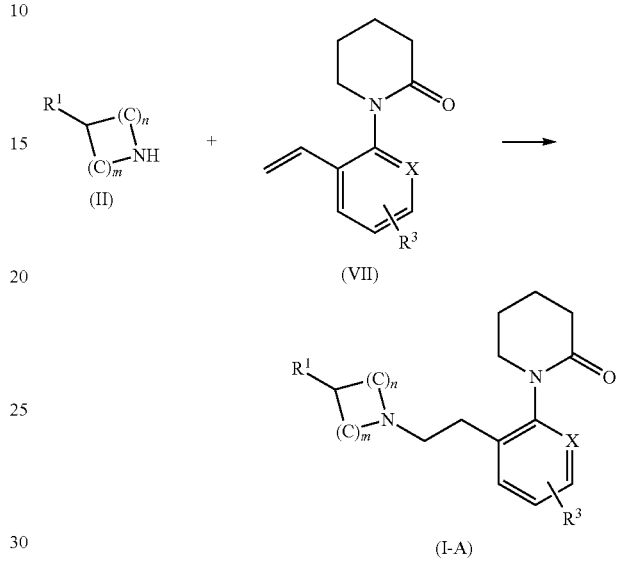

wherein X is C, m=1, n=2 or 3, $R^3$ is hydrogen and $R^1$ has the same definition as defined above for compounds of formula I.

This reaction may be performed in an inert solvent, for example acetonitrile, in the presence of a base such as $K_2CO_3$ and at reflux temperature, or according to any method known to the person skilled in the art.

Alternatively, some compounds of formula I-A wherein X is C, m=1, n=2, $R^3$ is hydrogen and $R^1$ is heteroaryl, may be prepared by reaction of a vinyl aromatic of formula V with a compound of formula VI according to the equation:

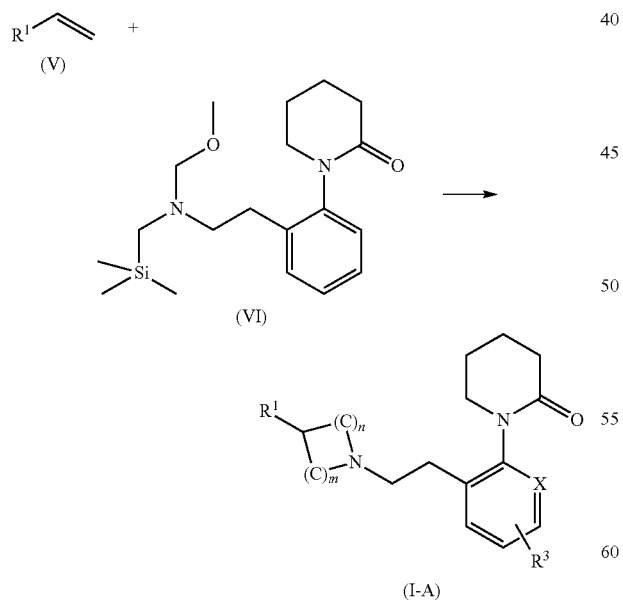

wherein X is C, m=1, n=2, $R^3$ is hydrogen and $R^1$ is heteroaryl.

This reaction may be performed in a polar solvent such as dichloromethane, in the presence of a Bronstedt acid such as trifluoroacetic acid, at room temperature, or according to any method known to the person skilled in the art.

Alternatively, some compounds of formula I-A wherein X is N, m=1, n=2, $R^3$ is substituted or unsubstituted $C_{1-4}$ alkyl or halogen and $R^1$ has the same definition as defined above for compounds of formula I-A, may be prepared by hydroamination of a vinyl heteroaromatic of formula VII with an amine of formula II according to the equation:

wherein X is N, m=1, n=2, $R^3$ is substituted or unsubstituted $C_{1-4}$ alkyl or halogen and $R^1$ has the same definition as defined above for compounds of formula I-A.

This reaction may be performed in a polar solvent such as ethanol, in the presence of a Bronstedt base such as triethylamine, at reflux, or according to any method known to the person skilled in the art.

Alternatively, some compounds having the general formula I may be prepared by functional group conversion on already assembled analogs of compounds having the general formula I, using procedures described in the literature or known to the person skilled in the art.

Amines of formula II wherein m=1, n=2 and $R^1$ is heteroaryl may be prepared by reaction of a heteroaromatic vinyl of formula V with a compound of formula VIII, followed by deprotection of the obtained compound of formula IX according to the equation:

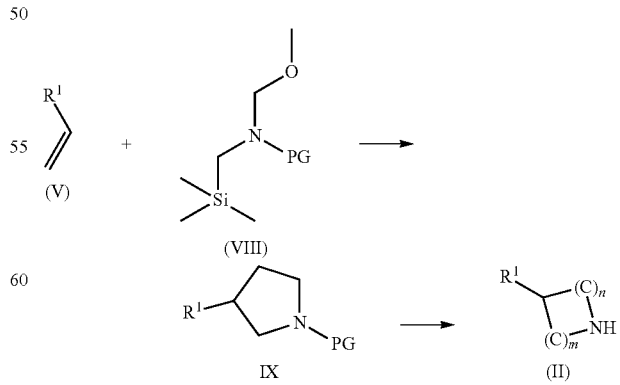

wherein m=1, n=2, $R^1$ is heteroaryl and PG represents a protecting group such as benzyl or allyl. This reaction may be performed in a polar solvent such as dichloromethane, in the presence of a Bronstedt acid such as trifluoroacetic acid, at room temperature, or according to any method known to the person skilled in the art.

The subsequent deprotection of compound of formula IX may be performed using procedures described in the literature such as palladium based deprotection (when PG is an allyl), hydrogenolysis using ammonium acetate as hydrogen source (when PG is a benzyl), or according to any other method known to the person skilled in the art.

Alternatively amines of formula II wherein m=1, n=2 and $R^1$ is substituted or unsubstituted alkyl or substituted or unsubstituted cycloalkyl may be prepared by reduction of the corresponding pyrrolidones of formula X according to the equation:

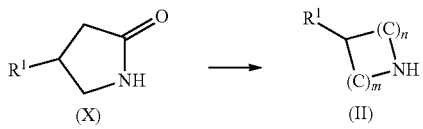

This reaction may be performed in THF, in the presence of LiAlH$_4$, at reflux temperature, or according to any method known to the person skilled in the art.

Alternatively, some amines of formula II wherein m is 1 and n is 1, 2 or 3 may be prepared by functional group transformation(s) on commercially available pyrrolidines or pyrrolidin-3-ones (when n=2) or commercially available azetidines (when n=1) or commercially available piperidines (when n=3) using procedures described in the literature or known to the person skilled in the art.

Alternatively, some amines of formula II wherein m=1 and n=3 may be prepared by hydrogenation of the corresponding substituted pyridines using procedures described in the literature or known to the person skilled in the art.

The synthesis of aldehydes of formula III can be performed using procedures described in the literature such as Dess Martin periodinane oxidation of the corresponding alcohol of formula XI (Dess, D. B., Martin, J. C., J. Org. Chem. 1983, 48, 4155-4156), or hydrolysis of an enol ether of formula XII, or according to any other method known to the person skilled in the art.

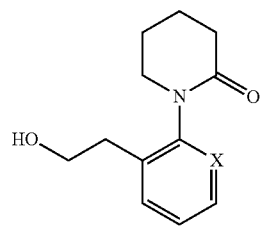

(XI)

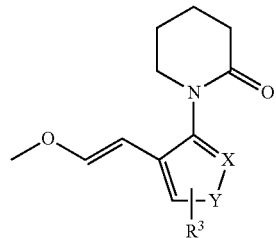

(XII)

Tosylate of formula IV may be prepared from the corresponding alcohol of formula XI wherein X is C according to any method known to the person skilled in the art.

The synthesis of compounds of formula V can be performed using procedures described in the literature such as heteroaromatic aldehyde olefination or heteroaromatic halide cross coupling, or according to any other method known to the person skilled in the art.

Compound of formula VI may be prepared by reaction of a tosylate of formula IV with 1-(trimethylsilyl)methanamine in an inert solvent such as acetonitrile, in the presence of a base such as K$_2$CO$_3$ and at reflux temperature followed by treatment with a mixture of aqueous formaldehyde and methanol in the presence of K$_2$CO$_3$ at 0° C., or according to any method known to the person skilled in the art.

Vinyl heteroaromatic compound of formula VII may be prepared by cross coupling reaction between vinylboronic acid pinacol ester and the corresponding heteroaromatic halide of formula XIII wherein Hal is bromide, chloride or iodide, or according to any method known to the person skilled in the art.

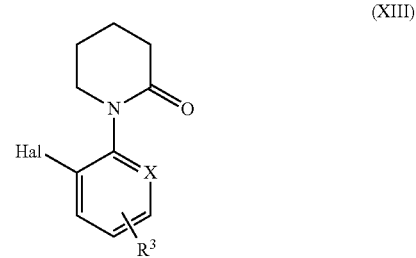

(XIII)

Compound of formula VIII wherein PG is allyl may be prepared according to the method described in PCT patent application WO2009/087058 or according to any other method known to the person skilled in the art.

The synthesis of compounds of formula X can be performed using procedures described in the literature or known to the person skilled in the art.

Alcohol of formula XI may be prepared according to any conventional method known to the person skilled in the art.

Some enol ether of formula XII may be preformed via a Wittig type reaction on aldehyde of formula XIV or according to any other method known to the person skilled in the art.

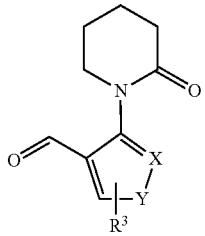

(XIV)

Some enol ether of formula XII may be preformed via a lactamisation of the corresponding aromatic amine of formula XV, or according to any other method known to the person skilled in the art.

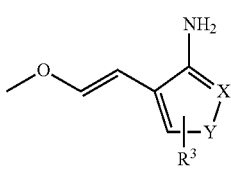

(XV)

In another embodiment, the present invention includes the synthesis of the following intermediates:

tert-butyl 3-[2-(methoxycarbonyl)phenyl]pyrrolidine-1-carboxylate;
tert-butyl 3-(2-carbamoylphenyl)pyrrolidine-1-carboxylate;
tert-butyl 3-(2-carbamoylphenyl)pyrrolidine-1-carboxylate, enantiomer 1;
tert-butyl 3-(2-carbamoylphenyl)pyrrolidine-1-carboxylate, enantiomer 2;
2-(pyrrolidin-3-yl)benzamide, enantiomer 1;
2-(pyrrolidin-3-yl)benzamide, enantiomer 2;
(3R)-3-(2,2,2-trifluoroethyl)pyrrolidine;
(3S)-3-(2,2,2-trifluoroethyl)pyrrolidine;
3-(2-chloro-2,2-difluoroethyl)pyrrolidine;
methyl 3-(4,4-difluorocyclohexyl)prop-2-enoate;
methyl 3-(tetrahydro-2H-pyran-4-yl)prop-2-enoate;
methyl 3-(tetrahydrofuran-2-yl)prop-2-enoate;
methyl 3-(tetrahydro-2H-pyran-3-yl)prop-2-enoate;
methyl 3-(4,4-difluorocyclohexyl)-4-nitrobutanoate;
methyl 3-(4,4-difluorocyclohexyl)-4-nitrobutanoate enantiomer 1;
methyl 3-(4,4-difluorocyclohexyl)-4-nitrobutanoate enantiomer 2;
methyl 4-nitro-3-(tetrahydro-2H-pyran-4-yl)butanoate;
methyl 4-nitro-3-(tetrahydrofuran-2-yl)butanoate;
methyl 4-nitro-3-(tetrahydro-2H-pyran-3-yl)butanoate;
4-(4,4-difluorocyclohexyl)pyrrolidin-2-one;
4-(4,4-difluorocyclohexyl)pyrrolidin-2-one enantiomer 1;
4-(4,4-difluorocyclohexyl)pyrrolidin-2-one enantiomer 2;
4-(tetrahydro-2H-pyran-4-yl)pyrrolidin-2-one;
4-(tetrahydro-2H-pyran-4-yl)pyrrolidin-2-one enantiomer 1;
4-(tetrahydro-2H-pyran-4-yl)pyrrolidin-2-one enantiomer 2;
4-(tetrahydrofuran-2-yl)pyrrolidin-2-one;
4-(tetrahydro-2H-pyran-3-yl)pyrrolidin-2-one;
3-(4,4-difluorocyclohexyl)pyrrolidine;
3-(4,4-difluorocyclohexyl)pyrrolidine enantiomer 1;
3-(4,4-difluorocyclohexyl)pyrrolidine enantiomer 2;
3-(tetrahydro-2H-pyran-4-yl)pyrrolidine enantiomer 1;
3-(tetrahydro-2H-pyran-4-yl)pyrrolidine enantiomer 2;
3-(tetrahydrofuran-2-yl)pyrrolidine;
3-(tetrahydro-2H-pyran-3-yl)pyrrolidine;
tert-butyl 3-(3-cyanophenoxy)azetidine-1-carboxylate;
tert-butyl 3-(5-bromo-2-methoxyphenoxy)azetidine-1-carboxylate;
3-(5-bromo-2-methoxyphenoxy)azetidine;
tert-butyl 3-[(5-fluoropyridin-2-yl)oxy]azetidine-1-carboxylate;
2-(azetidin-3-yloxy)-5-fluoropyridine;
2-ethenyl-6-(propan-2-yloxy)pyridine;
2-ethenyl-6-(1H-pyrazol-1-yl)pyridine;
2-methoxy-6-[1-(prop-2-en-1-yl)pyrrolidin-3-yl]pyridine;
4-methoxy-2-[1-(prop-2-en-1-yl)pyrrolidin-3-yl]pyrimidine;
2-(propan-2-yloxy)-6-[1-(prop-2-en-1-yl)pyrrolidin-3-yl]pyridine;
2-[1-(prop-2-en-1-yl)pyrrolidin-3-yl]-6-(1H-pyrazol-1-yl)pyridine;
4-methoxy-2-(pyrrolidin-3-yl)pyrimidine;
2-(propan-2-yloxy)-6-(pyrrolidin-3-yl)pyridine;
2-(1H-pyrazol-1-yl)-6-(pyrrolidin-3-yl)pyridine;
2-(1-benzylpyrrolidin-3-yl)pyridine enantiomer 1;
2-(1-benzylpyrrolidin-3-yl)pyridine enantiomer 2;
2-(pyrrolidin-3-yl)pyridine enantiomer 1 dihydrochloride;
2-(pyrrolidin-3-yl)pyridine enantiomer 2 dihydrochloride;
4-(pyrrolidin-3-yl)benzonitrile enantiomer 2;
4-(pyrrolidin-3-yl)benzonitrile enantiomer 1;
2-(cyclobutyloxy)-6-(pyrrolidin-3-yl)pyridine; 5-bromo-N-[2-(2-hydroxyethyl)phenyl]pentanamide;
1-[2-(2-hydroxyethyl)phenyl]piperidin-2-one;
2-[2-(2-oxopiperidin-1-yl)phenyl]ethyl 4-methylbenzenesulfonate;
[2-(2-oxopiperidin-1-yl)phenyl]acetaldehyde;
2-(2-oxopiperidin-1-yl)pyridine-3-carbaldehyde;
1-[3-(2-methoxyethenyl)pyridin-2-yl]piperidin-2-one;
[2-(2-oxopiperidin-1-yl)pyridin-3-yl]acetaldehyde;
1-[2-(2-{[(trimethylsilyl)methyl]amino}ethyl)phenyl]piperidin-2-one;
1-[2-(2-{(methoxymethyl)[(trimethylsilyl)methyl]amino}ethyl)phenyl]piperidin-2-one;
3-ethenyl-2-fluoropyridine;
2-ethenyl-3-fluoropyridine;
methyl 2-(1-{2-[2-(2-oxopiperidin-1-yl)phenyl]ethyl}piperidin-3-yl)benzoate;
methyl 2-(1-{2-[2-(2-oxopiperidin-1-yl)phenyl]ethyl}pyrrolidin-3-yl)benzoate;
methyl 2-(1-{2-[2-(2-oxopiperidin-1-yl)phenyl]ethyl}pyrrolidin-3-yl)benzoate enantiomer 1;
methyl 2-(1-{2-[2-(2-oxopiperidin-1-yl)phenyl]ethyl}pyrrolidin-3-yl)benzoate enantiomer 2;
2-(1-{2-[2-(2-oxopiperidin-1-yl)phenyl]ethyl}piperidin-3-yl)benzoic acid;
2-(1-{2-[2-(2-oxopiperidin-1-yl)phenyl]ethyl}pyrrolidin-3-yl)benzoic acid;
2-(1-{2-[2-(2-oxopiperidin-1-yl)phenyl]ethyl}pyrrolidin-3-yl)benzoic acid enantiomer 1;
2-(1-{2-[2-(2-oxopiperidin-1-yl)phenyl]ethyl}pyrrolidin-3-yl)benzoic acid enantiomer 2;
1-{2-[2-(3-hydroxypyrrolidin-1-yl)ethyl]phenyl}piperidin-2-one;
1-{2-[2-(2-oxopiperidin-1-yl)phenyl]ethyl}pyrrolidin-3-yl methanesulfonate;
1-{2-[2-(3-hydroxyazetidin-1-yl)ethyl]phenyl}piperidin-2-one;
1-{2-[2-(2-oxopiperidin-1-yl)phenyl]ethyl}azetidin-3-yl methanesulfonate;
1-(2-{2-[3-(piperidin-2-yl)pyrrolidin-1-yl]ethyl}phenyl)piperidin-2-one;
methyl (1-{2-[2-(2-oxopiperidin-1-yl)phenyl]ethyl}pyrrolidin-3-yl)acetate;
1-(2-{2-[3-(2-hydroxy-2-methylpropyl)pyrrolidin-1-yl]ethyl}phenyl)piperidin-2-one;
(1-{2-[2-(2-oxopiperidin-1-yl)phenyl]ethyl}pyrrolidin-3-yl)acetic acid;
1-(3-{2-[3-(6-fluoropyridin-2-yl)pyrrolidin-1-yl]ethyl}pyridin-2-yl)piperidin-2-one;
1-(3-{2-[3-(6-hydroxypyridin-2-yl)pyrrolidin-1-yl]ethyl}pyridin-2-yl)piperidin-2-one;
4-(2-methoxyvinyl)-1-methyl-1H-pyrazol-3-amine;
1-[4-(2-methoxyvinyl)-1-methyl-1H-pyrazol-3-yl]piperidin-2-one;
[1-methyl-3-(2-oxopiperidin-1-yl)-1H-pyrazol-4-yl]acetaldehyde;
1-[3-chloro-5-(trifluoromethyl)pyridin-2-yl]piperidin-2-one;
1-[5-(trifluoromethyl)-3-vinylpyridin-2-yl]piperidin-2-one;
5-fluoro-2-(2-oxopiperidin-1-yl)nicotinaldehyde;
1-[5-fluoro-3-(2-methoxyvinyl)pyridin-2-yl]piperidin-2-one; and
[5-fluoro-2-(2-oxopiperidin-1-yl)pyridin-3-yl]acetaldehyde.

The compounds of the present invention are for use as a medicament, in the acute or prophylactic treatment of migraine.

The methods of the invention comprise administration to a mammal (preferably a human) suffering from migraine of a compound according to the invention in an amount sufficient to alleviate or prevent the disorder or condition.

The compound is conveniently administered in any suitable unit dosage form, including but not limited to one containing 0.1 to 2000 mg, preferably 0.1 to 1000 mg, more preferably 0.1 to 500 mg of active ingredient per unit dosage form.

The term "treatment" as used herein includes curative treatment and prophylactic treatment.

By "prophylactic" is meant prevention of the occurrence or recurrence of a disorder or condition.

A further aspect of the present invention relates to a pharmaceutical composition comprising an effective amount of a compound of formula I in combination with a pharmaceutically acceptable diluent or carrier.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

For oral compositions, the daily dosage is in the range 0.1 mg to 2000 mg of compounds of formula I. For oral compositions the dosage unit is in the range 0.1 mg to 1000 mg of compounds of formula I, preferably 0.1 mg to 500 mg.

In compositions for parenteral administration, the quantity of compound of formula I present is at least 0.5% by weight and can be up to 33% by weight with respect to the total weight of the composition. For the preferred parenteral compositions, the dosage unit is in the range 0.1 mg to 2000 mg of compounds of formula I.

The daily dose can fall within a wide range of dosage units of compound of formula I and is generally in the range 0.1 to 2000 mg, preferably 0.1 to 1000 mg. However, it should be understood that the specific doses can be adapted to particular cases depending on the individual requirements, at the physician's discretion.

EXAMPLES

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

NMR spectra are recorded on a BRUKER AVANCE 400 NMR Spectrometer fitted with a Linux workstation running XWIN NMR 3.5 software and a 5 mm inverse $^1$H/BB probehead, or BRUKER DRX 400 NMR fitted with a SG Fuel running XWIN NMR 2.6 software and a 5 mm inverse geometry $^1$H/$^{13}$C/$^{19}$F triple probehead. The compound is studied in $d_6$-dimethylsulfoxide (or $d_3$-chloroform) solution at a probe temperature of 300 K and at a concentration of 10 mg/ml. The instrument is locked on the deuterium signal of $d_6$-dimethylsulfoxide (or $d_3$-chloroform). Chemical shifts are given in ppm downfield from TMS (tetramethylsilane) taken as internal standard.

HPLC analyses are performed using an Agilent 1100 series HPLC system mounted with a Waters XBridge MS C18, 5 µm, 150×4.6 mm column. The gradient runs from 100% solvent A (water/acetonitrile/ammonium formate solution 85/5/10 (v/v/v)) to 100% solvent B (water/acetonitrile/ammonium formate solution 5/85/10 (v/v/v) in 6 minutes with a hold at 100% B of 5 minutes. The flow rate is set at 1.8 ml/min during 6 minutes then increased at 2.3 ml/min during 2 minutes with a hold at 2.3 ml/min during 3 minutes. A split of 1/25 is used just before API source. The chromatography is carried out at 45° C. The ammonium formate solution (pH~8.5) is prepared by dissolution of ammonium formate (630 mg) in water (1 l) and addition of ammonium hydroxide 30% (500 µl).

Mass spectrometric measurements in LC/MS mode are performed as follows:

HPLC Conditions

For basic elution, analyses are performed using:
    a WATERS Alliance HPLC system with diode array detector mounted with a WATERS XBridge MS C18, 5 µm, 150×4.6 mm column. The gradient runs from 100% solvent A (water/acetonitrile/ammonium formate solution 85/5/10 (v/v/v)) to 100% solvent B (water/acetonitrile/ammonium formate solution 5/85/10 (v/v/v)) in 6 minutes with a hold at 100% B of 5 minutes. The flow rate is set at 1.8 ml/min during 6 minutes then increased at 2.3 ml/min during 2 minutes with a hold at 2.3 ml/min during 3 minutes. A split of 1/25 is used just before API source. The chromatography is carried out at 45° C. The ammonium formate solution (pH~8.5) is prepared by dissolution of ammonium formate (630 mg) in water (1 l) and addition of ammonium hydroxide 30% (500 µl).

A WATERS Acquity UPLC system with diode array detector mounted with a Acquity UPLC BEH C18, 1.7 µm, 100×2.1 mm column. The gradient runs from a mixture of solvent A/solvent B 99/1 (v/v) to solvent A/solvent B 5/95 (v/v) in 4.5 minutes with a 2 minutes hold. The flow rate is set at 0.4 ml/min during 4.5 minutes then increased at 0.5 ml/min with a hold at 0.5 ml/min during 2 minutes without split before API source. The chromatography is carried out at 55° C. Solvent A (pH~8.5) is prepared by dissolution of ammonium formate (63 mg) in water (1 l) and addition of ammonium hydroxide 30% (50 µl), solvent B is acetonitrile.

For acidic elution analyses are performed using a WATERS Alliance HPLC system with diode array detector mounted with a Waters Sunfire MS C18, 5 µm, 150×4.6 mm column. The gradient runs from 100% solvent A (water/acetonitrile/trifluoroacetic acid solution 85/5/10 (v/v/v)) to 100% solvent B (water/acetonitrile/trifluoroacetic acid solution 5/85/10 (v/v/v) in 6 minutes with a hold at 100% B of 5 minutes. The flow rate is set at 1.8 ml/min during 6 minutes then increased at 2.3 ml/min during 2 minutes with a hold at 2.3 ml/min during 3 minutes. A split of 1/25 is used just before API source. The chromatography is carried out at 45° C. The trifluoroacetic acid solution is prepared with water, acetonitrile and trifluoroacetic acid (49.75/49.75/0.5, v/v/v) and has a pH around 2.

MS Conditions

Samples are dissolved in acetonitrile/water 70/30 (v/v) at the concentration of about 250 µg/ml. API spectra (+ or −) are performed using:
- a FINNIGAN LCQ ion trap mass spectrometer. APCI source operated at 450° C. and the capillary heater at 160° C. ESI source operated at 3.5 kV and the capillary heater at 210° C.
- a SQD Waters single quadrupole mass spectrometer with an ESI source. The source parameters are as follows: ESI capillary voltage 3.0 kV, Cone and Extractor voltage 25 and 2 V respectively, Source block temperature 130° C., Desolvatation temperature 370° C., Cone gaz flow 120 L/Hr (Nitrogen), Desolvatation gaz flow 800 L/Hr.
- a Quattro Micro Waters triple quadrupole mass spectrometer with an ESI source. The source parameters are as follows: ESI capillary voltage 2.8 kV, Cone and Extractor voltage 30 and 2 V respectively, Source block temperature 120° C., Desolvatation temperature 320° C., Cone gaz flow 120 L/Hr (Nitrogen), Desolvatation gaz flow 550 L/H.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 µm) from J&W Scientific. Helium (purity 99.999%) is used as carrier gas. The injector (CTC A200S autosampler) and the transfer line operate at 290 and 250° C., respectively. Sample (1 µl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

High resolution mass spectrometry measurements are run on a Waters LCT Time of flight mass spectrometer equipped with an ESI source The source parameters are as follows: ESI capillary voltage 2.5 kV, cone voltage 135 V, source block temperature 135° C., desolvation temperature 350° C., cone gas flow 20 L/Hr (Nitrogen), desolvation Gas flow 800 L/Hr. The detector is set with a flight tube at 7.2 KV and an MCP detector at 2,500 V.

Specific rotation is recorded on a Perkin-Elmer 341 polarimeter. The angle of rotation is recorded at 25° C. on solutions in methanol, at 589 nm or 365 nm.

Melting points are determined on a Büchi 535 or 545 Tottoli-type fusionometer, and are not corrected, or by the onset temperature on a Perkin Elmer DSC 7.

Preparative chromatographic separations are performed on Kromasil spherical silica, particle size 10-13 µm 100 Å, using Novasep dynamic axial compression columns (80 mmID), flow rates 140 ml/min. Solvent mixtures are described in individual procedures. Reverse phase separations are carried out using 500 g of either Kromasil C18 10 µm (acidic or neutral conditions) or Phenomenex Gemini C18 10 µM (basic conditions) in 80 mm ID columns with a flow rate of 150 ml/min. Products are detected at 215 nm unless otherwise specified.

Preparative Chiral Chromatographic separations are performed on using liquid phase chromatography instrument with various mixtures of lower alcohols and C5 to C8 linear, branched or cyclic alkanes at ±350 ml/min. Solvent mixtures as well as columns are described in individual procedures.

Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling).

Example 1

Synthesis of Amines of Formula II 1.1 Synthesis of 2-(pyrrolidin-3-yl)benzamide, enantiomer 1 a8

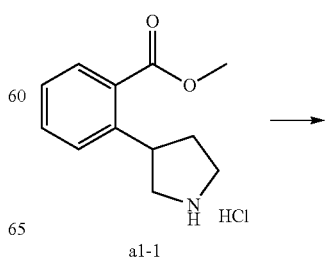

a1-1

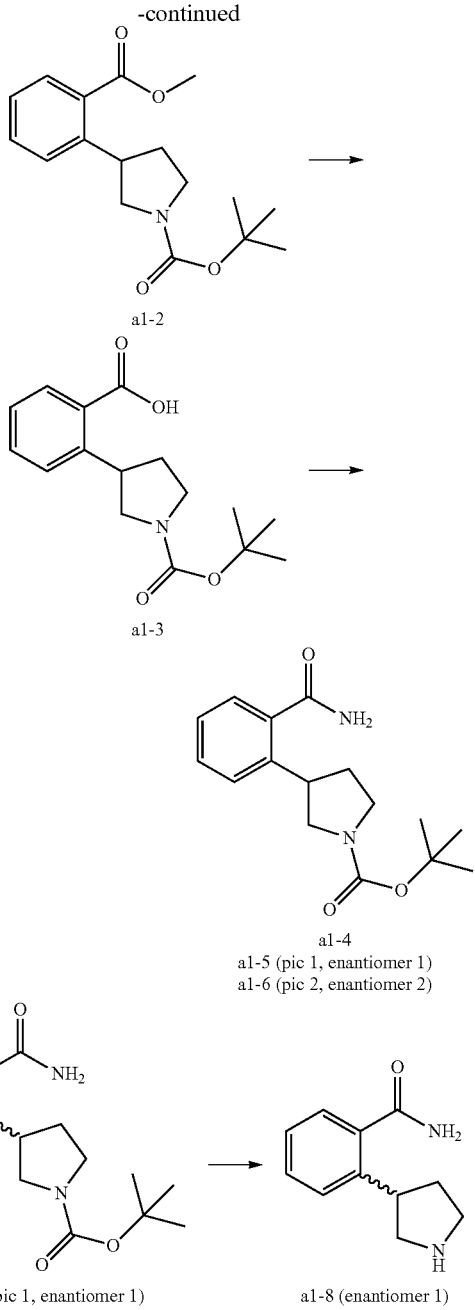

a1-2 a1-3 a1-4
a1-5 (pic 1, enantiomer 1)
a1-6 (pic 2, enantiomer 2)

a1-5 (pic 1, enantiomer 1)   a1-8 (enantiomer 1)

1.1.1 Synthesis of tert-butyl 3-[2-(methoxycarbonyl)phenyl]pyrrolidine-1-carboxylate a1-2

To a stirred solution of methyl 2-(pyrrolidin-3-yl)benzoate hydrochloride a1-1 (4.83 g, 20 mmol, 1 eq) in dichloromethane (100 ml) at room temperature are added 4-dimethylaminopyridine (244 mg, 2 mmol, 0.1 eq) and triethylamine (8.43 ml, 60 mmol, 3 eq). The solution is stirred at room temperature for 5 minutes and a solution of (Boc)$_2$O (4.58 g, 21 mmol, 1.05 eq) in dichloromethane is added. The reaction mixture is stirred at room temperature overnight and quenched with 1M HCl (100 ml). The organic layer is dried over MgSO$_4$, filtered off and evaporated under vacuum to give 6.1 g of pure tert-butyl 3-[2-(methoxycarbonyl)phenyl] pyrrolidine-1-carboxylate a1-2.

Yield: 100%.

1.1.2 Synthesis of 2-[1-(tert-butoxycarbonyl)pyrrolidin-3-yl]benzoic acid a1-3

NaOH 5M (7.7 ml, 38.6 mmol, 2 eq) is added to a stirred solution of 3-[2-(methoxycarbonyl)phenyl]pyrrolidine-1-carboxylate a1-2 (5.9 g, 19.3 mmol, 1 eq) in MeOH (50 ml) at 65° C. The reaction mixture is stirred overnight at 65° C., then evaporated under vacuum and water (40 ml) is added. The resulting mixture is extracted with ethyl acetate/ethanol (100 ml/10 ml) and again with ethyl acetate (100 ml). The combined organic layers are dried over MgSO$_4$, filtered off and evaporated under vacuum to afford 5.5 g of pure 2-[1-(tert-butoxycarbonyl)pyrrolidin-3-yl]benzoic acid a1-3.

Yield: 98%.

1.1.3 Synthesis of tert-butyl 3-(2-carbamoylphenyl)pyrrolidine-1-carboxylate a1-4 and enantiomers a1-5 and a1-6

A stirred solution of 2-[1-(tert-butoxycarbonyl)pyrrolidin-3-yl]benzoic acid a1-3 (5.5 g, 19 mmol, 1 eq) in dichloromethane (150 ml) is saturated, at 0° C., with gaseous ammonia NH$_3$ for 1 hour. BOP reagent (8.82 g, 19.9 mmol, 1.05 eq) is added portionwise to this solution. The reaction mixture is warmed to room temperature and stirred overnight. The reaction mixture is filtered off and the solid washed with dichloromethane (100 ml). The organic layer is evaporated under vacuum and the residue obtained is purified by chromatography over silicagel (eluent: CH$_2$Cl$_2$/MeOH 98.5/1.5) to give 5.4 g of tert-butyl 3-(2-carbamoylphenyl)pyrrolidine-1-carboxylate a1-4.

Yield: 100%.

LC-MS (MH$^+$): 291.

The two enantiomers are separated by chiral chromatography (Phase: LUX-CELL-2; 76×370 mm column; 200 ml/min; eluent: iPrOH/Heptane 30/70) to afford 2.5 g of enantiomer 1 a1-5 (first eluted) and 2.35 g of enantiomer 2 a1-6 (second eluted).

Yield for a1-5: 45%.

Yield for a1-6: 42%.

LC-MS (MH$^+$): 291.

1.1.4 Synthesis of 2-(pyrrolidin-3-yl)benzamide, enantiomer 1 a1-8

Tert-butyl 3-(2-carbamoylphenyl)pyrrolidine-1-carboxylate, enantiomer 1 a1-5 (2.5 g, 8.61 mmol, 1 eq) is dissolved in ethanol (100 ml). A saturated solution of HCl in EtOH is added (10 ml). The reaction mixture is stirred for 20 h and evaporated to dryness to afford 1.64 g of 2-(pyrrolidin-3-yl) benzamide, enantiomer 1 a1-8 which is used in the next step without any further purification.

Yield: assumed quantitative.

LC-MS (MH$^+$): 191.2-(pyrrolidin-3-yl)benzamide a1-7 and 2-(pyrrolidin-3-yl)benzamide, enantiomer 2 a1-9 may be prepared according to the same method.

1.2 Synthesis of 3-(2,2,2-trifluoroethyl)pyrrolidine a1-11

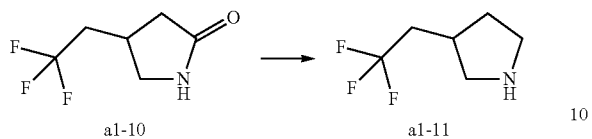

To a solution of 4-(2,2,2-trifluoroethyl)pyrrolidin-2-one a1-10 (4.0 g, 23.9 mmol, 1 eq) in freshly distilled THF, LiAlH$_4$ (2.27 g, 60 mmol, 2.5 eq) is added carefully at 0° C. After completion of the addition, the mixture is heated at reflux for 1.5 h in a flask equipped with a condenser cooled at −10° C. The reaction mixture is then carefully quenched with water at 0° C. and filtered on a pad of celite/MgSO$_4$. The filtrate is concentrated under reduced pressure at room temperature to afford 2.82 g of 3-(2,2,2-trifluoroethyl)pyrrolidine a1-11.

Yield: 77%.

LC-MS (MH$^+$): 154.

The following intermediates may be synthesized according to the same method.

| a1-12 | (3R)-3-(2,2,2-trifluoroethyl)pyrrolidine | LC-MS (MH$^+$): 154 |
|---|---|---|
| a1-13 | (3S)-3-(2,2,2-trifluoroethyl)pyrrolidine | LC-MS (MH$^+$): 154 |
| a1-14 | 3-(2-chloro-2,2-difluoroethyl)pyrrolidine | LC-MS (MH$^+$): 170/172 |

1.3 Synthesis of 3-(4,4-difluorocyclohexyl)pyrrolidine a1-34

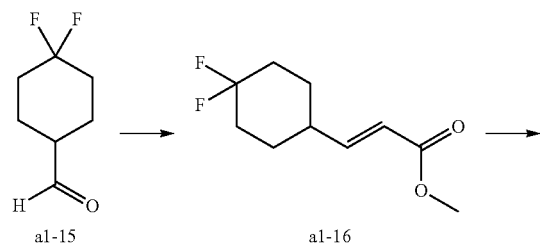

1.3.1 Synthesis of methyl 3-(4,4-difluorocyclohexyl)prop-2-enoate a1-16

Methyl(triphenylphosphoranylidene)acetate (8.827 g, 26 mmol, 1.1 eq) is added at room temperature to a solution of 4,4-difluorocyclohexanecarbaldehyde (3.55 g, 24 mmol, 1 eq) in dry THF (60 ml). The mixture is stirred for 6 h and the solvent is evaporated. Hexane (50 ml) is added to the crude, the mixture is put a few minutes in an ultrasonic bath, stirred for 1 h and filtered. The filtrate is concentrated under reduced pressure to afford 4.05 g of methyl 3-(4,4-difluorocyclohexyl)prop-2-enoate a1-16.

Yield: 83%.

$^1$H NMR (400 MHz, CDCl$_3$) δ 6.91 (m, 1H), 5.85 (m, 1H), 3.75 (m, 3H), 2.29 (m, 1H), 2.12 (m, 3H), 1.80 (m, 5H), 1.56 (t, 2H, J=12.5 Hz).

The following intermediates may be synthesized according to the same method.

| a1-17 | methyl 3-(tetrahydro-2H-pyran-4-yl)prop-2-enoate | GC-MS (MH$^+$): 170 |
|---|---|---|
| a1-18 | methyl 3-(tetrahydrofuran-2-yl)prop-2-enoate | $^1$H NMR δ 6.91 (dd, J = 15.7, 4.9 Hz, 1 H), 6.01 (dd, J = 15.7, 1.6 Hz, 1 H), 4.50 (m, 1 H), 3.86 (m, 6 H), 3.72 (s, 3 H), 2.12 (m, 2 H), 1.90 (m, 8 H), 1.68 (m, 1 H) |
| a1-19 | methyl 3-(tetrahydro-2H-pyran-3-yl)prop-2-enoate | $^1$H NMR δ 6.81 (dd, J = 15.8, 7.2 Hz, 1 H), 5.84 (d, J = 15.8 Hz, 1 H), 3.88 (d, J = 11.3 Hz, 2 H), 3.72 (m, 3 H), 3.39 (m, 1 H), 3.24 (t, J = 10.4 Hz, 1 H), 2.47 (m, 1 H), 1.91 (m, 1 H), 1.66 (m, 2 H), 1.44 (m, 1 H) |

1.3.2 Synthesis of methyl 3-(4,4-difluorocyclohexyl)-4-nitrobutanoate a1-20

Methyl 3-(4,4-difluorocyclohexyl)prop-2-enoate (4.054 g, 0.198 mol, 1 eq) is dissolved in nitromethane (23 L, 0.423 mol, 21.3 eq) and 1,8-diazabicyclo[5,4,0]undec-7-ene (3.025 g, 0.198 mol, 1 eq) is added at room temperature. The solution is stirred overnight at room temperature then evaporated. The residue is dissolved in ethyl acetate and the solution is washed with 1 M HCl and water. The organic phase is dried with $MgSO_4$ and evaporated under vacuum. The residue is purified by chromatography over silicagel (eluent: $CH_2Cl_2$ 100%) to afford methyl 3-(4,4-difluorocyclohexyl)-4-nitrobutanoate a1-20.

Yield: 68%.
LC-MS ($MH^+$): 266.

The following intermediates may be synthesized according to the same method.

| a1-23 | methyl 4-nitro-3-(tetrahydro-2H-pyran-4-yl)butanoate | LC-MS ($MH^+$): 232 |
|---|---|---|
| a1-24 | methyl 4-nitro-3-(tetrahydrofuran-2-yl)butanoate | LC-MS ($MH^+$): 218 |
| a1-25 | methyl 4-nitro-3-(tetrahydro-2H-pyran-3-yl)butanoate | LC-MS ($MH^+$): 232 |

Methyl 3-(4,4-difluorocyclohexyl)-4-nitrobutanoate enantiomer 1 a1-21 (first eluted) and enantiomer 2 a1-22 (second eluted) may be obtained by chiral chromatography of a1-20 (Phase: Chiralpak ASV; 50×490 mm column; 80 ml/min; eluent: i-PrOH/Heptane 50/50). Yield for a1-21: 70%.

Yield for a1-22: 70%.
LC-MS ($MH^+$): 266.

1.3.3 Synthesis of 4-(4,4-difluorocyclohexyl)pyrrolidin-2-one a1-26

Methyl 3-(4,4-difluorocyclohexyl)-4-nitrobutanoate a1-20 (1.390 g, 5.24 mmol, 1 eq) is dissolved in methanol (35 ml) and Raney Nickel (50% in water, 200 mg, 1.7 mmol, 0.3 eq) is rinsed 3 times with methanol and added to the solution. The mixture is heated overnight at 50° C. under a $H_2$ atmosphere (20 bars). The mixture is then filtered and the filtrate is evaporated under reduced pressure to afford 4-(4,4-difluorocyclohexyl)pyrrolidin-2-one a1-26.

Yield: assumed quantitative.
LC-MS ($MH^+$): 204.

The following intermediates may be synthesized according to the same method.

| a1-27 | 4-(4,4-difluorocyclohexyl)pyrrolidin-2-one enantiomer 1 | LC-MS ($MH^+$): 204 |
|---|---|---|
| a1-28 | 4-(4,4-difluorocyclohexyl)pyrrolidin-2-one enantiomer 2 | LC-MS ($MH^+$): 204 |
| a1-29 | 4-(tetrahydro-2H-pyran-4-yl)pyrrolidin-2-one | LC-MS ($MH^+$): 169 |
| a1-32 | 4-(tetrahydrofuran-2-yl)pyrrolidin-2-one | LC-MS ($MH^+$): 156 |
| a1-33 | 4-(tetrahydro-2H-pyran-3-yl)pyrrolidin-2-one | LC-MS ($MH^+$): 170 |

4-(Tetrahydro-2H-pyran-4-yl)pyrrolidin-2-one enantiomer 1 a1-30 (first eluted) and enantiomer 2 a1-31 (second eluted) may be obtained by chiral chromatography of a1-29 (Chiracel OJ Phase; solvent: iPrOH/Heptane 30/70)

Yield for a1-30 and a1-31: overall yield before chiral separation (over 4 steps, starting from corresponding aldehyde): 55%.

LC-MS ($MH^+$): 169.

1.3.4 Synthesis of 3-(4,4-difluorocyclohexyl)pyrrolidine a1-34

Lithium aluminium hydride (397.6 mg, 10.49 mmol, 2 eq) is added portionwise at 0° C. to a solution of 4-(4,4-difluorocyclohexyl)pyrrolidin-2-one a1-26 (assumed quantitative from previous step, 5.24 mmol, 1 eq) in dry THF (10 ml). The reaction mixture is allowed to warm to room temperature and stirred overnight, then quenched by water at 0° C. and filtered on celite. The solvent is evaporated under reduced pressure to afford 3-(4,4-difluorocyclohexyl)pyrrolidine a1-34.

Yield: assumed quantitative.
LC-MS ($MH^+$): 190.

The following intermediates may be synthesized according to the same method.

| a1-35 | 3-(4,4-difluorocyclohexyl)pyrrolidine enantiomer 1 | LC-MS ($MH^+$): 190 |
|---|---|---|
| a1-36 | 3-(4,4-difluorocyclohexyl)pyrrolidine enantiomer 2 | LC-MS ($MH^+$): 190 |
| a1-37 | 3-(tetrahydro-2H-pyran-4-yl)pyrrolidine | LC-MS ($MH^+$): 156 |
| a1-38 | 3-(tetrahydro-2H-pyran-4-yl)pyrrolidine enantiomer 1 | LC-MS ($MH^+$): 156 |
| a1-39 | 3-(tetrahydro-2H-pyran-4-yl)pyrrolidine enantiomer 2 | LC-MS ($MH^+$): 156 |
| a1-40 | 3-(tetrahydrofuran-2-yl)pyrrolidine | LC-MS ($MH^+$): 142 |
| a1-41 | 3-(tetrahydro-2H-pyran-3-yl)pyrrolidine | LC-MS ($MH^+$): 142 |

1.4 Synthesis of 3-(azetidin-3-yloxy)benzonitrile a1-45

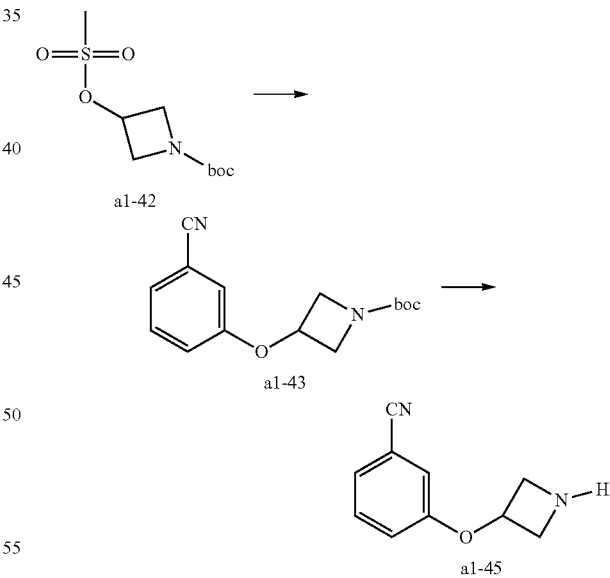

1.4.1 Synthesis of tert-butyl 3-(3-cyanophenoxy)azetidine-1-carboxylate a1-43

3-cyanophenol (284 mg, 2.38 mmol, 1.2 eq) is added to a mixture of tert-butyl 3-[(methylsulfonyl)oxy]azetidine-1-carboxylate (500 mg, 1.99 mmol, 1 eq) and $Cs_2CO_3$ (2.27 g, 6.96 mmol, 3.5 eq) in DMF (20 ml). The reaction is heated overnight at 80° C., then cooled to room temperature. Brine (100 ml) is added and the mixture is extracted twice with diethyl ether. The combined organic phases are washed with brine, dried over MgSO$_4$ and evaporated under reduced pressure. The residue is purified by basic reverse phase chromatography (gradient: acetonitrile/H$_2$O/NH$_4$OH from 50/50/0.1 to 80/20/0.1) to afford 262.4 mg of tert-butyl 3-(3-cyanophenoxy)azetidine-1-carboxylate a1-43.

Yield: 48%.
LC-MS (MH$^+$): 275.

Tert-butyl 3-(5-bromo-2-methoxyphenoxy)azetidine-1-carboxylate a1-44 may be synthesized according to the same method.

1.4.2 Synthesis of 3-(azetidin-3-yloxy)benzonitrile a1-45

Trifluoroacetic acid (10 ml) is added to a solution of tert-butyl 3-(3-cyanophenoxy)azetidine-1-carboxylate a1-43 (260 mg, 0.95 mmol, 1 eq) in dichloromethane (10 ml). The reaction mixture is stirred for 2 hours at room temperature, then concentrated to dryness to afford 262.3 mg of crude 3-(azetidin-3-yloxy)benzonitrile a1-45 as an oil. This oil is used in the next step without any further purification.

Yield: 100%.
LC-MS (MH$^+$): 175.

3-(5-Bromo-2-methoxyphenoxy)azetidine a1-46 may be synthesized according to the same method.

1.5 Synthesis of 2-(azetidin-3-yloxy)-5-fluoropyridine a1-49

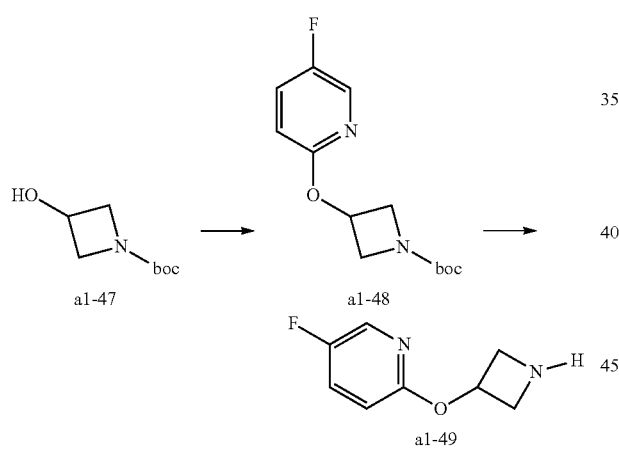

1.5.1 Synthesis of tert-butyl 3-[(5-fluoropyridin-2-yl)oxy]azetidine-1-carboxylate a1-48

Potassium tert-butoxide (1M in THF, 14.4 ml, 14.4 mmol, 5 eq) and 2,5-difluoropyridine (498.3 mg, 4.33 mmol, 1.5 eq) are added to a mixture of tert-butyl 3-hydroxyazetidine-1-carboxylate a1-47 (500 mg, 2.89 mmol, 1 eq) in DMSO (50 ml). The reaction is stirred for 4 h at room temperature. Brine (70 ml) and water (10 ml) are added. The resulting mixture is extracted with ethyl acetate (3×50 ml). The combined organic phases are dried over MgSO$_4$, filtered and concentrated in vacuo. The residue of evaporation is purified by flash chromatography over silicagel (eluent: EtOAc/Heptane 10/90) to afford 240 mg of tert-butyl 3-[(5-fluoropyridin-2-yl)oxy]azetidine-1-carboxylate a1-48.

Yield: 31%.
LC-MS (MH$^+$): 269.

1.5.2 Synthesis of 2-(azetidin-3-yloxy)-5-fluoropyridine a1-49

2-(Azetidin-3-yloxy)-5-fluoropyridine a1-49 may be prepared by deprotection of tert-butyl 3-[(5-fluoropyridin-2-yl)oxy]azetidine-1-carboxylate a1-48 as described in example 1.4.2.

LC-MS (MH$^+$): 169.

1.6 Synthesis of 2-methoxy-6-(pyrrolidin-3-yl)pyridine a1-59

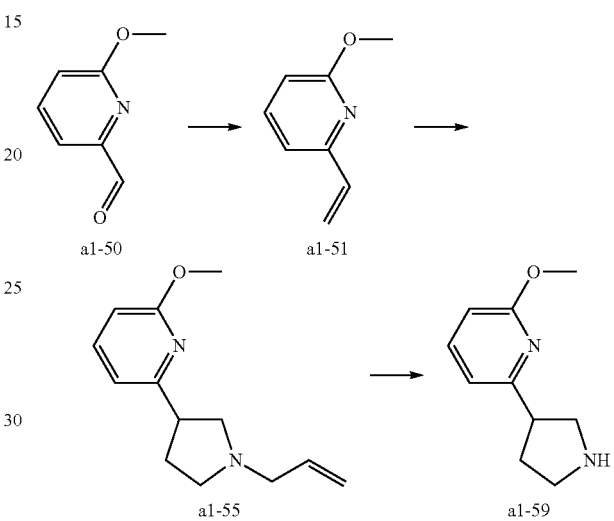

1.6.1 Synthesis of 2-ethenyl-6-methoxypyridine a1-51

To a suspension of methyl(triphenyl)phosphonium bromide (7.07 g, 19.8 mmol, 1.1 eq) in dry THF (50 ml) at 0° C. is added n-butyl lithium (1.6M in cyclohexane, 12.5 ml, 19.8 mmol, 1.1 eq). After stirring at 0° C. for 20 minutes, a solution of 6-methoxypyridine-2-carbaldehyde a1-50 (2.5 g, 18 mmol, 1 eq) in dry THF (10 ml) is added dropwise to the mixture. The reaction mixture is warmed to room temperature for 30 minutes. The reaction mixture is quenched with 3 drops of water, and Rochelle salt is added (10 g). The mixture is filtered on Celite and MgSO$_4$. The crude residue is distilled to afford 400 mg of pure 2-ethenyl-6-methoxypyridine a1-51.

Yield: 16%.
$^1$H NMR δ 7.51 (t, J=7.6 Hz, 1H), 6.82 (d, J=7.2 Hz, 1H), 6.72 (dd, J=17.0, 10.6 Hz, 1H), 6.62 (d, J=8.2 Hz, 1H), 6.29 (dd, J=17.2, 1.4 Hz, 1H), 5.41 (dd, J=10.6, 1.4 Hz, 1H), 3.96 (s, 3H).

Alternatively 2-ethenyl-4-methoxypyrimidine a1-52 and 2-ethenyl-6-(1H-pyrazol-1-yl)pyridine a1-54 may be prepared by reaction of 2-bromo-4-methoxypyrimidine with potassium ethenyl(trifluoro)borate.

a1-52, LC-MS (MH$^+$): 137.
a1-54, LC-MS (MH$^+$): 172.

Alternatively, 2-ethenyl-6-(propan-2-yloxy)pyridine a1-53 may be prepared by reaction 2-bromo-6-(propan-2-yloxy)pyridine of with tributyl(ethenyl)stannane.

LC-MS (MH$^+$): 400.

1.6.2 Synthesis of 2-methoxy-6-[1-(prop-2-en-1-yl)pyrrolidin-3-yl]pyridine a1-55

To a solution of 2-ethenyl-6-methoxypyridine a1-51 (400 mg, 3 mmol, 1 eq) in trifluoroacetic acid/dichloromethane (200 µl/2 ml) is added N-(methoxymethyl)-N-[(trimethylsilyl)methyl]prop-2-en-1-amine until all styrene a1-51 is consumed. The solvent is removed under vacuum and the crude residue is purified by basic reverse phase chromatography over silicagel (gradient: $CH_3CN/H_2O/NH_4OH$ from 50/50/0.1 to 80/20/0.1) to afford 210 mg of pure 2-methoxy-6-[1-(prop-2-en-1-yl)pyrrolidin-3-yl]pyridine a1-55.

Yield: 30%.
LC-MS ($MH^+$): 219.

The following intermediates may be synthesized according to the same method.

| | | |
|---|---|---|
| a1-56 | 4-methoxy-2-[1-(prop-2-en-1-yl)pyrrolidin-3-yl]pyrimidine | LC-MS ($MH^+$): 220 |
| a1-57 | 2-(propan-2-yloxy)-6-[1-(prop-2-en-1-yl)pyrrolidin-3-yl]pyridine | LC-MS ($MH^+$): 247 |
| a1-58 | 2-[1-(prop-2-en-1-yl)pyrrolidin-3-yl]-6-(1H-pyrazol-1-yl)pyridine | LC-MS ($MH^+$): 255 |

1.6.3 Synthesis of 2-methoxy-6-(pyrrolidin-3-yl)pyridine a1-59

To a solution of 2-methoxy-6-[1-(prop-2-en-1-yl)pyrrolidin-3-yl]pyridine a1-55 (218 mg, 1 mmol, 1 eq) in dichloromethane (3 ml) are added 1,3-dimethylbarbituric acid (470 mg, 3 mmol, 3 eq) and $Pd(PPh_3)_4$ (20 mg) and the mixture is warmed overnight at 40° C. The reaction mixture is loaded on an ion exchange acidic resin cartridge, washed with methanol (2×50 ml) and then released with a 1M solution of ammonia in methanol (20 ml) to afford 150 mg of crude 2-methoxy-6-(pyrrolidin-3-yl)pyridine a1-59 that is used in the next step without any further purification.

Yield: 84%.

The following intermediates may be synthesized according to the same method.

| | | |
|---|---|---|
| a1-60 | 4-methoxy-2-(pyrrolidin-3-yl)pyrimidine | — |
| a1-61 | 2-(propan-2-yloxy)-6-(pyrrolidin-3-yl)pyridine | LC-MS ($MH^+$): 207 |
| a1-62 | 2-(1H-pyrazol-1-yl)-6-(pyrrolidin-3-yl)pyridine | LC-MS ($MH^+$): 215 |

1.7 Synthesis of 2-(pyrrolidin-3-yl)pyridine enantiomers a1-66 and a1-67

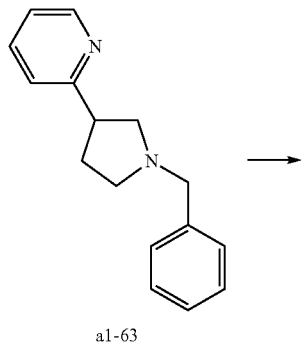

a1-63

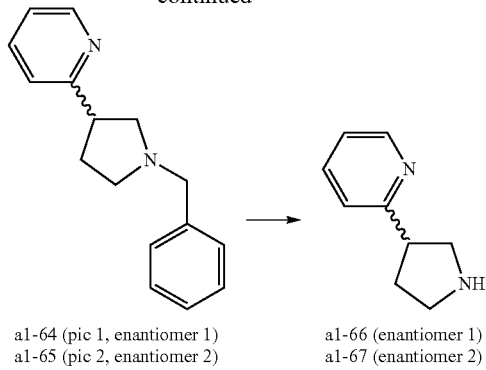

a1-64 (pic 1, enantiomer 1)　　a1-66 (enantiomer 1)
a1-65 (pic 2, enantiomer 2)　　a1-67 (enantiomer 2)

1.7.1 Synthesis of 2-(1-benzylpyrrolidin-3-yl)pyridine enantiomers a1-64 and a1-65

2-(1-Benzylpyrrolidin-3-yl)pyridine enantiomers a1-64 and a1-65 are obtained by chiral chromatography of the racemic mixture a1-63 (Phase: Chiralpak AD; 80*475 mm column; 200 ml/min; eluent: $CH_3CN$).

2-(1-Benzylpyrrolidin-3-yl)pyridine enantiomer 1 a1-64

$^1$H NMR (400 MHz, $CDCl_3$) δ 8.53 (d, 1H, J=4.3 Hz), 7.58 (td, 1H, J=7.7, 1.4 Hz), 7.33 (m, 4H), 7.23 (m, 2H), 7.09 (m, 1H), 3.69 (m, 2H), 3.55 (m, 1H), 3.08 (t, 1H, J=8.6 Hz), 2.87 (m, 1H), 2.69 (m, 2H), 2.34 (m, 1H), 2.10 (m, 1H).

2-(1-Benzylpyrrolidin-3-yl)pyridine enantiomer 2 a1-65

$^1$H NMR (400 MHz, $CDCl_3$) δ 8.53 (d, 1H, J=4.1 Hz), 7.58 (td, 1H, J=7.7, 1.7 Hz), 7.33 (m, 4H), 7.23 (m, 2H), 7.09 (m, 1H), 3.69 (m, 2H), 3.55 (m, 1H), 3.08 (t, 1H, J=8.6 Hz), 2.87 (m, 1H), 2.69 (m, 2H), 2.34 (m, 1H), 2.11 (m, 1H).

1.7.2 Synthesis of 2-(pyrrolidin-3-yl)pyridine enantiomer 1 dihydrochloride a1-66

To 2-(1-benzylpyrrolidin-3-yl)pyridine enantiomer 1 a1-64 (10.01 g, 41.96 mmol, 1 eq) in methanol (340 ml) is added Pd/C (5%, 1.98 g). A solution of ammonium formate (10.69 g, 167.83 mmol, 4 eq) in water (55 ml) is then added dropwise over a period of 10 minutes. The reaction mixture is heated for 45 mins at 68° C., then cooled to room temperature. The catalyst is filtered off using Celite, washed with methanol (60 ml) and the pooled filtrates evaporated to dryness. The residue is retaken in methanol (50 ml) and evaporated again. Dichloromethane (100 ml) is added to the residue, the solid obtained is filtered, washed with dichloromethane (30 ml) and the pooled filtrates are evaporated to dryness to give a yellow oil. This oil is dissolved in isopropanol (60 ml) and a mixture of isopropanol (21 ml)/aqueous HCl 6N (21 ml, 3 eq) is added slowly over a period of 15 minutes to the solution. The mixture is stirred at room temperature overnight, the precipitate obtained is filtered, washed with isopropanol (10 ml) and dried under vacuum for 4 hours at 40° C. to afford 7.90 g of 2-(pyrrolidin-3-yl)pyridine enantiomer 1 dihydrochloride a1-66. Yield: 85%.

LC-MS ($MH^+$): 149.

2-(pyrrolidin-3-yl)pyridine enantiomer 2 dihydrochloride a1-67 may be prepared according to the same method. Yield: 85%.

LC-MS (MH+): 149.

1.8 Chiral separation of 4-(pyrrolidin-3-yl)benzonitrile a1-68

4-(pyrrolidin-3-yl)benzonitrile enantiomer 1 a1-70 and 4-(pyrrolidin-3-yl)benzonitrile enantiomer 2 a1-69 may be prepared by chiral chromatography of 4-(pyrrolidin-3-yl)benzonitrile a1-68.

1.9 Synthesis of 2-(cyclobutyloxy)-6-(pyrrolidin-3-yl)pyridine a1-72

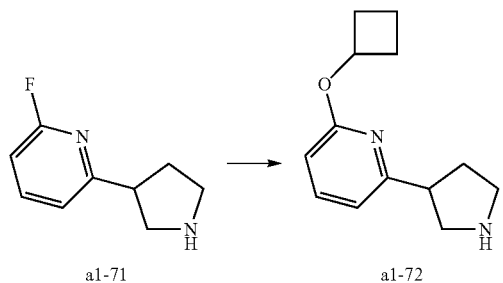 [SMILES: Fc1cccc(C2CCNC2)n1 ; c1cc(OC2CCC2)nc(C2CCNC2)c1]

a1-71      a1-72

Potassium tert-butoxide (337 mg, 3 mmol, 3 eq) is added portionwise at room temperature to a solution of cyclobutanol (144 mg, 2 mmol, 2 eq) in DMSO (2 ml) and the mixture is stirred for 2 days. 2-Fluoro-6-(pyrrolidin-3-yl)pyridine hydrochloride (202 mg, 1 mmol, 1 eq) in DMSO (2 ml) is added and the mixture is stirred for 48 hours. Dichloromethane and water are then added to the reaction mixture, and the two phases are separated after vigorous shaking. The aqueous layer is reextracted with dichloromethane. The combined organic layers are dried on MgSO4, filtered and the filtrate condensed under reduced pressure to afford crude 2-(cyclobutyloxy)-6-(pyrrolidin-3-yl)pyridine a1-72, which is used in the next step without any further purification.

Yield: assumed quantitative.

LC-MS (MH+): 219.

Example 2

Synthesis of 1-(2-{2-[3-(3-fluorophenyl)piperidin-1-yl]ethyl}phenyl) piperidin-2-one oxalate 24

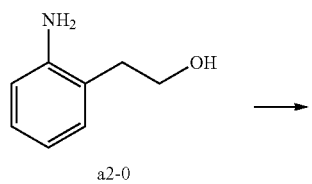

a2-0

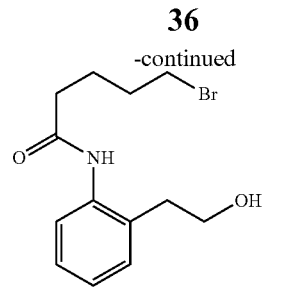

a2-1

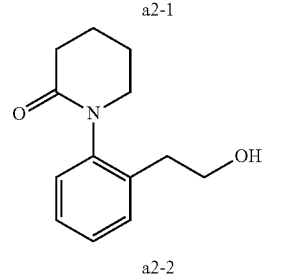

a2-2

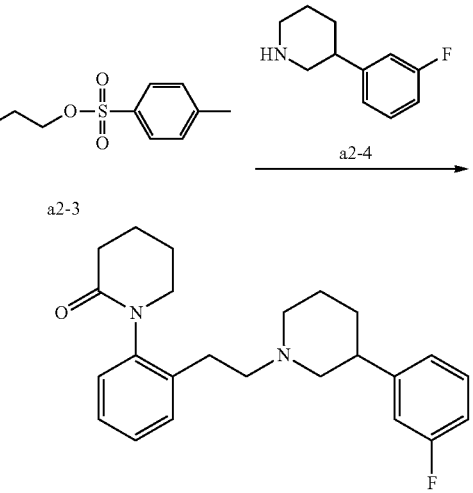

a2-3 a2-4

24

2.1 Synthesis of 5-bromo-N-[2-(2-hydroxyethyl)phenyl]pentanamide a2-1

A solution of 2-(2-aminophenyl)ethanol a2-0 (450 g, 3.28 mol, 1 eq) and triethylamine (332 g, 3.28 mol, 1 eq) in dichloromethane (2 l) is cooled at −5° C. and bromovalerylchloride (654 g, 3.28 mol, 1 eq) in dichloromethane (2 l) is added dropwise without exceeding 0° C. The organic phase is washed with HCl 1N (4×2 l) and brine (1×2 l). The aqueous layer is extracted with dichloromethane (1×2 l). The combined organic layers are dried over MgSO4, filtered and evaporated under vacuum to afford 1008 g of 5-bromo-N-[2-(2-hydroxyethyl)phenyl]pentanamide a2-1.

Yield: 100%.

LC-MS (MH+): 301.

2.2 Synthesis of 1-[2-(2-hydroxyethyl)phenyl]piperidin-2-one a2-2

A solution of 5-bromo-N-[2-(2-hydroxyethyl)phenyl]pentanamide a2-1 (938 g, 3.28 mol, 1 eq) in THF (6 l) is cooled at −5° C. Potassium tert-butoxide (552 g, 4.92 mol, 1.5 eq) is added portionwise, without exceeding 0° C., then the mixture is warmed up to room temperature. The reaction mixture is washed with a saturated aqueous solution of NaCl (3×2 l). The aqueous layers are extracted with dichloromethane (2×2 l), the combined organic layers are dried over MgSO$_4$, filtered and condensed under reduced pressure. The residue is recrystallized from tert-butyl methyl ether to afford 510 g of 1-[2-(2-hydroxyethyl)phenyl]piperidin-2-one a2-2.

Yield: 71%.
LC-MS (MH$^+$): 220.

2.3 Synthesis of 2-[2-(2-oxopiperidin-1-yl)phenyl]ethyl 4-methylbenzenesulfonate a2-3

Dimethylaminopyridine (1.83 g, 15 mmol, 0.05 eq) and triethylamine (63.5 ml, 450 mmol, 1.5 eq) are added to a solution of 1-[2-(2-hydroxyethyl)phenyl]piperidin-2-one a2-2 (65.7 g, 300 mmol, 1 eq) in dichloromethane (250 ml) at 0° C. The mixture is stirred at 0° C. for 15 minutes, then a solution of 4-toluenesulfonyl chloride (63 g, 330 mmol, 1.1 eq) in dichloromethane (250 ml) is added dropwise. The reaction mixture is then warmed up to room temperature and stirred overnight. The reaction mixture is washed with water, 1N HCl, then dried over MgSO$_4$, filtered and evaporated under vacuum. The residue is purified by chromatography over silicagel (gradient: CH$_2$Cl$_2$/MeOH from 100/0 to 98/2) to afford 99 g of 2-[2-(2-oxopiperidin-1-yl)phenyl]ethyl 4-methylbenzenesulfonate a2-3.

Yield: 88%.
LC-MS (MH$^+$): 374.

2.4 Synthesis of 1-(2-{2-[3-(3-fluorophenyl)piperidin-1-yl]ethyl}phenyl)piperidin-2-one oxalate 24

3-(3-Fluorophenyl)piperidine hydrochloride a2-4 (432 mg, 2 mmol, 1 eq) and K$_2$CO$_3$ (829 mg, 6 mmol, 3 eq) are added to a solution 2-[2-(2-oxopiperidin-1-yl)phenyl]ethyl 4-methylbenzenesulfonate a2-3 (747 mg, 2 mmol, 1 eq) in acetonitrile (10 ml). The reaction mixture is stirred at 85° C. overnight, then filtered and the filtrate is condensed under reduced pressure. The residue is purified by basic reverse phase chromatography over silicagel (gradient CH$_3$CN/H$_2$O/NH$_4$OH from 50/50/0.1 to 80/20/0.1) to afford 472 mg (1.24 mmol) of 1-(2-{2-[3-(3-fluorophenyl)piperidin-1-yl]ethyl}phenyl)piperidin-2-one as a free base. Oxalic acid (111 mg, 1.24 mmol, 1 eq) is added to the residue dissolved in diethylether. The precipitate obtained is filtered and dried under vacuum to afford 517 mg of 1-(2-{2-[3-(3-fluorophenyl)piperidin-1-yl]ethyl}phenyl)piperidin-2-one oxalate 24.

Yield: 55%.
LC-MS (MH$^+$): 381.

Compounds 1, 3, 5, 6, 7, 8, 9, 10, 14, 15, 16, 18, 21, 22, 24, 25, 26, 27, 28, 29, 33, 34, 35, 36, 37, 38, 39, 40, 41, 42, 43, 46, 48, 49, 51, 53, 54, 56, 57, 67, 69, 73, 75, 76, 77, 78 and 81 may be synthesized according to the same method.

Compounds 12 and 13 may be obtained by chiral chromatography of 3.

Compounds 19 and 20 may be obtained by chiral chromatography of 6.

Example 3

Synthesis of 3-(1-{2-[2-(2-oxopiperidin-1-yl)phenyl]ethyl}azetidin-3-yl)benzonitrile oxalate 31

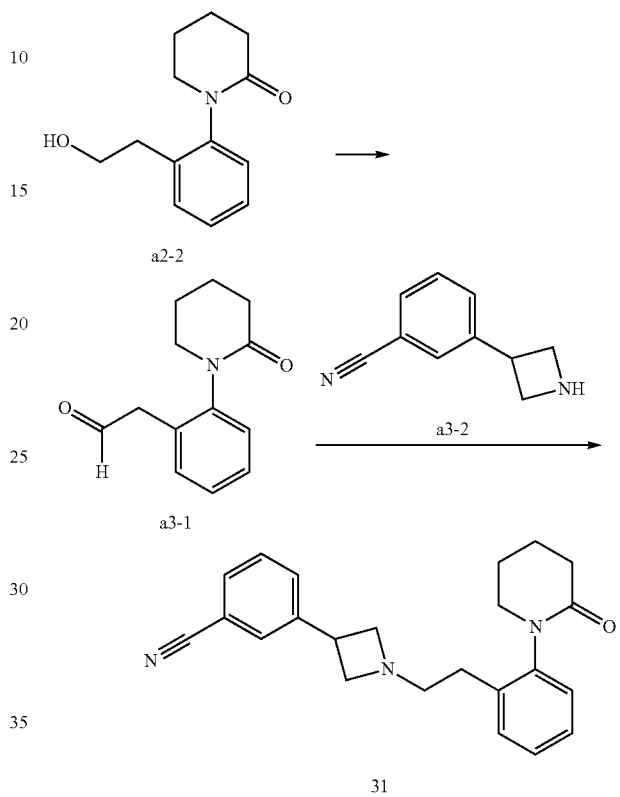

3.1 Synthesis of [2-(2-oxopiperidin-1-yl)phenyl]acetaldehyde a3-1

Dess Martin periodinane (3.36 g, 7.91 mmol, 1.3 eq) is added portionwise under stirring to 1-[2-(2-hydroxyethyl)phenyl]piperidin-2-one a2-2 (1.33 g, 6.09 mmol, 1 eq) in dichloromethane (40 ml). After a few hours additional Dess Martin periodinane (1.29 g, 3.04 mmol, 0.5 eq) is added and the reaction mixture is stirred overnight at room temperature, then filtrated and evaporated to dryness to afford crude [2-(2-oxopiperidin-1-yl)phenyl]acetaldehyde a3-1, which is used in the next step without any further purification.

Yield: assumed quantitative.

3.2 Synthesis of 3-(1-{2-[2-(2-oxopiperidin-1-yl)phenyl]ethyl}azetidin-3-yl)benzonitrile oxalate 31

To [2-(2-oxopiperidin-1-yl)phenyl]acetaldehyde a3-1 (108.6 mg, 0.5 mmol, 1 eq) and 3-(azetidin-3-yl)benzonitrile a3-2 (97.33 mg, 0.5 mmole, 1 eq) in methanol (4 ml) are added acetic acid (42.9 μl, 0.75 mmol, 1.5 eq) then NaBH$_3$CN (94.3 mg, 1.5 mmol, 3 eq). The reaction mixture is stirred overnight at room temperature. The crude reaction mixture is then loaded on an ion exchange acidic resin cartridge (2 g) prewashed with methanol. The cartridge is washed twice with approximately 3 column volumes of methanol, then eluted with 3 column volumes of 1M NH₃ in methanol. This eluate is evaporated to dryness to give 141 mg of a crude material which is purified by reverse phase chromatography (basic mode; gradient: H₂O/acetonitrile/NH₄OH from 60/40/0.1 to 30/70/0.1 in 10 minutes). The residue obtained is redissolved in acetone (approximately 3 ml), and after addition of oxalic acid (22.7 mg, 0.25 mmol, 1 eq), a precipitate slowly appeared. This precipitate is filtered, washed with diethylether and dried overnight under vacuum at 40° C. to afford 69.6 mg of 3-(1-{2-[2-(2-oxopiperidin-1-yl)phenyl]ethyl}azetidin-3-yl)benzonitrile oxalate 31.

Yield: 31%.

LC-MS (MH⁺):360.

Compounds 23, 30, 32, 44, 45, 47, 52, 58, 59, 60, 61, 62, 65, 66 and 68 may be synthesized according to the same method.

Example 4

Synthesis of 1-[3-(2-{3-[6-(propan-2-yloxy)pyridin-2-yl]pyrrolidin-1-yl}ethyl)pyridin-2-yl]piperidin-2-one oxalate 94

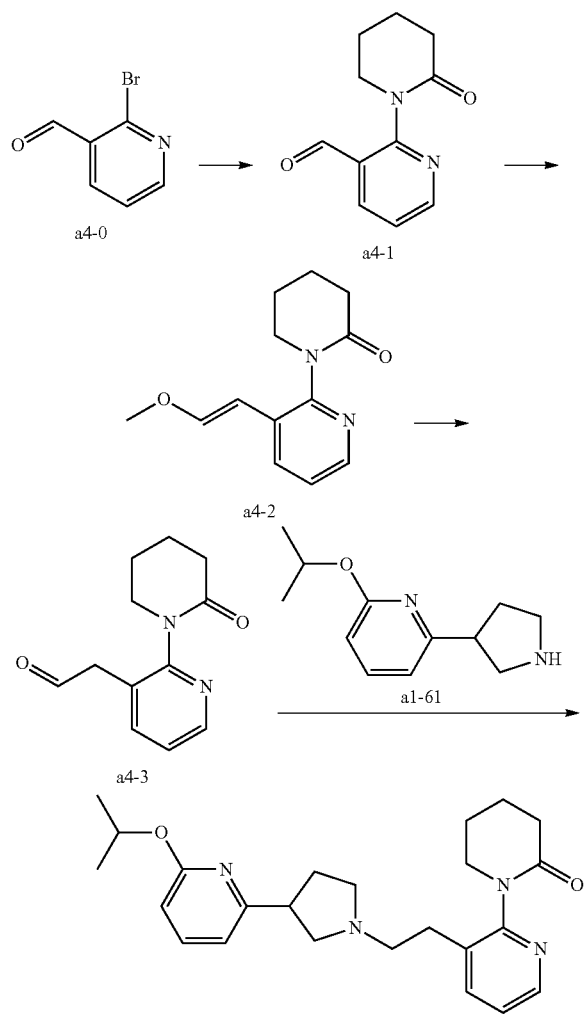

4.1 Synthesis of 2-(2-oxopiperidin-1-yl)pyridine-3-carbaldehyde a4-1

2-Bromopyridine-3-carbaldehyde a4-0 (0.5 g, 2.7 mmol, 1 eq) is dissolved in dry and degassed 1,4-dioxane (15 ml). Piperidin-2-one (0.4 g, 4.03 mmol, 1.5 eq), 9,9-dimethyl-4,5-bis(diphenylphosphino)xanthene (0.31 g, 0.538 mmol, 0.2 eq), tris(dibenzylideneacetone)dipalladium(0) (0.123 g, 0.134 mmol, 0.05 eq) and cesium carbonate (1.752 g, 5.376 mmol, 2 eq) are added. The mixture is heated in a sealed tube in a microwave oven at 120° C. for 45 min. The resulting suspension is filtered over celite and the celite washed with 1,4-dioxane. The filtrate is evaporated under reduced pressure. The residue is then dispersed in ethyl acetate, sonicated, filtered and the filtrate is evaporated under reduced pressure to afford 1.1 g of crude 2-(2-oxopiperidin-1-yl)pyridine-3-carbaldehyde a4-1 which is used in the next step without any further purification.

Yield: 50%.

LC-MS (MH⁺): 204.

4.2 Synthesis of 1-[3-(2-methoxyethenyl)pyridin-2-yl]piperidin-2-one a4-2

Methoxymethyl-triphenylphosphonium chloride (3.59 g, 10.48 mmol, 1.3 eq) is dissolved in dry tetrahydrofuran (150 ml) under nitrogen. This solution is cooled at 0° C. and potassium tert-butoxide (1.085 g, 9.67 mmol, 1.2 eq) is added. The reaction mixture is stirred at 0° C. for 30 min. A solution of crude 2-(2-oxopiperidin-1-yl)pyridine-3-carbaldehyde a4-1 (4.2 g, 8.06 mmol, 1 eq) in dry THF (50 ml) is added, then the reaction mixture is warmed up to room temperature and stirred for 1 hour. The solvent is removed under reduced pressure, the residue is taken with ethyl acetate, stirred, filtered and the solid cake washed with ethyl acetate (2 times). The filtrate is evaporated under reduced pressure. The residue is purified by chromatography over silicagel (gradient: CH₂Cl₂/MeOH/NH₄OH 100/0/0 to 97/3/0.3). The product obtained is redissolved in methanol, catched over an acidic column, washed with methanol and then released with ammonia 1M in methanol. The solvent is evaporated under reduced pressure to afford 540 mg of 1-[3-(2-methoxyethenyl)pyridin-2-yl]piperidin-2-one a4-2.

Yield: 11%.

LC-MS (MH⁺): 233.

4.3 Synthesis of [2-(2-oxopiperidin-1-yl)pyridin-3-yl]acetaldehyde a4-3

1-[3-(2-Methoxyethenyl)pyridin-2-yl]piperidin-2-one a4-2 (0.340 g, 1.464 mmol, 1 eq) is dissolved in a mixture of formic acid and water (10 ml/0.5 ml). The reaction mixture is heated at 50° C. overnight. The solvent is removed under reduced pressure to afford crude [2-(2-oxopiperidin-1-yl)pyridin-3-yl]acetaldehyde a4-3 which is used in the next step without any further purification.

LC-MS (MH⁺): 219.

4.4 Synthesis of 1-[3-(2-{3-[6-(propan-2-yloxy)pyridin-2-yl]pyrrolidin-1-yl}ethyl)pyridin-2-yl]piperidin-2-one oxalate 94

2-(Propan-2-yloxy)-6-(pyrrolidin-3-yl)pyridine a1-61 (0.302 g, 1.464 mmol, 1 eq) is dissolved in methanol (15 ml) and the solution is cooled at 0° C. Acetic acid (0.527 g, 8.784 mmol, 6 eq), N,N,-diisopropylethylamine (0.378 g, 2.928 mmol, 2 eq) and sodium cyanoborohydride (0.552 g, 8.784 mmol, 6 eq) are added. The reaction mixture is stirred for 5 min, and then poured on crude [2-(2-oxopiperidin-1-yl)pyridin-3-yl]acetaldehyde a4-3 (1.46 mmol, 1 eq) cooled at 0°. After 10 min at 0° C., the reaction mixture is warmed up to room temperature. Hydrochloric acid 1N is added until acidic pH. The solution is catched over an acidic column, washed with methanol and then released with ammonia 1M in methanol. The solvent is evaporated under reduced pressure. The residue is purified by LC-MS basic reverse phase (gradient $CH_3CN/H_2O/NaHCO_3$ from 5/95/0.5 to 95/5/0.5). The residue of evaporation is dissolved in a minimum of acetone and oxalic acid (1 eq) is added to form the salt. The solvent is removed under reduced pressure. The residue is taken in diethyl ether, the mixture is stirred, sonicated and filtered. The precipitate is washed with diethyl ether (2 times) to afford 75 mg of 1-[3-(2-{3-[6-(propan-2-yloxy)pyridin-2-yl]pyrrolidin-1-yl}ethyl)pyridin-2-yl]piperidin-2-one oxalate 94.

Yield: 12.5%.

LC-MS (MH+): 409.

Compounds 63, 70, 71, 79, 80, 88, 89, 90, 91, 92, 93, 95, 96, 97, 98, 99, 100, 101, 102, 103, 104, 105 and 106 may be synthesized according to the same method.

Example 5

Synthesis of 1-(2-{2-[3-(4-methyl-1,3-thiazol-2-yl)pyrrolidin-1-yl]ethyl}phenyl)piperidin-2-one oxalate 87

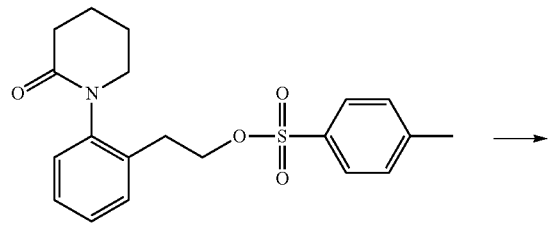

a2.3

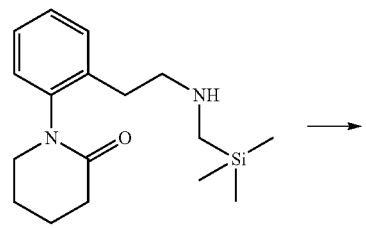

a5-1

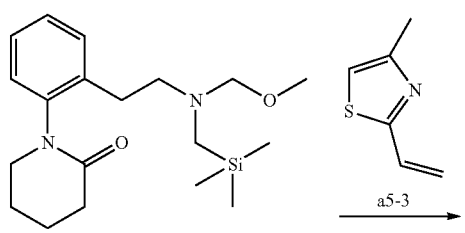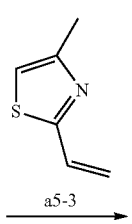

a5-2       a5-3

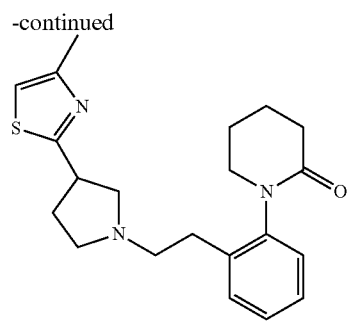

87

5.1 Synthesis of 1-[2-(2-{[(trimethylsilyl)methyl]amino}ethyl)phenyl]piperidin-2-one a5-1

To 2-[2-(2-oxopiperidin-1-yl)phenyl]ethyl 4-methyl benzenesulfonate a2-3 (22.4 g, 0.060 mol, 1 eq) in acetonitrile (100 ml) are added 1-(trimethylsilyl)methanamine (6.8 g, 0.066 mol, 1.1 eq) and $K_2CO_3$ (16.6 g, 0.120 mol, 2 eq). The reaction mixture is heated at 85° C. for 2 hours under nitrogen. After filtration the solvent is removed under reduced pressure and the residue obtained is purified by basic reverse phase chromatography (gradient $CH_3CN/H_2O/NaHCO_3$ from 50/50/0.1 to 80/20/0.1) to afford 7.66 g of 1-[2-(2-{[(trimethylsilyl)methyl]amino}ethyl)phenyl]piperidin-2-one a5-1.

Yield: 42%.

LC-MS (MH+): 305.

5.2 Synthesis of 1-[2-(2-{(methoxymethyl)[(trimethylsilyl)methyl]amino}ethyl)phenyl]piperidin-2-one a5-2

1-[2-(2-{[(Trimethylsilyl)methyl]amino}ethyl)phenyl]piperidin-2-one a5-1 (912 mg, 3 mmol, 1 eq) is slowly added at −10° C. to a solution of methanol (220 µl, 5.4 mmol, 1.8 eq) and aqueous formaldehyde (37%, 600 µl). The reaction mixture is stirred at 0° C. for 1 h. Potassium carbonate (2 g) is added and the mixture is stirred 1 h at 0° C. Dichloromethane (15 ml) is added, the mixture obtained is dried over $MgSO_4$, filtered, and the filtrate is concentrated under vacuum to afford 2.34 g of 1-[2-(2-{(methoxymethyl)[(trimethylsilyl)methyl]amino}ethyl)phenyl]piperidin-2-one a5-2.

Yield: 99%.

$^1$H NMR (CDCl$_3$, 400 MHz) δ: 7.23 (m, 1H), 7.18 (m, 2H), 7.04 (dd, J1=5.0 Hz, J2=3.6 Hz, 1H), 5.23 (s, 1H), 4.02 (m, 1H), 3.52 (m, 1H), 3.35 (m), 3.18 (s, 2H), 2.80 (m, 2H), 2.62 (m, 2H), 2.47 (m, 2H), 2.17 (m, 2H), 1.90 (m, 4H), 1.67 (m, 1H), 0.03 (m, 9H)

5.3 Synthesis of 2-ethenyl-4-methyl-1,3-thiazole a5-3

In a three-necked round bottom flask under argon, BuLi (1.6 M solution in hexane, 3.43 ml, 5.5 mmol, 1.1 eq) is slowly added to methyl(triphenyl)phosphonium bromide (1.79 g, 5 mmol, 1 eq) in THF (15 ml) without exceeding 5° C. After 1 h under stirring at 0° C., 4-methyl-1,3-thiazole-2-carbaldehyde (635 mg, 5 mmol, 1 eq) is added. The reaction mixture is allowed to return to ambient temperature and stirred overnight. The reaction is quenched with Rochelle salt (potassium sodium tartrate) (2 g) and 3 drops of water. The mixture is diluted with diethyl ether and dried over magnesium sulfate. Solvents are removed under vacuum and the crude product is distilled (+/−60° C.; 10$^{-2}$ Bar) to afford 335 mg of 2-ethenyl-4-methyl-1,3-thiazole a5-3 as a clear oil.

Yield: 54%.

$^1$H NMR (CDCl$_3$, 400 MHz) δ: 6.87 (dd, J$_1$=17.5 Hz, J$_2$=10.9 Hz, 1H), 6.78 (s, 1H), 6.01 (d, J=17.5 Hz, 1H), 5.50 (d, J=10.9 Hz, 1H), 2.44 (s, 3H).

The following intermediates may be synthesized according to the same method.

| a5-4 | 3-ethenyl-2-fluoropyridine | LC-MS (MH$^+$): 123 |
|---|---|---|
| a5-5 | 2-ethenyl-3-fluoropyridine | $^1$H NMR (CDCl$_3$, 400 MHz)δ: 8.27 (d, J = 4.4 Hz, 1 H), 7.26 (t, J = 9.3 Hz, 1 H), 7.08 (m, 1 H), 6.90 (dd, J1 = 17.4 Hz, J2 = 11.0 Hz, 1 H), 6.32 (dd, J1 = 17.4 Hz, J2 = 1.1 Hz, 1 H), 5.49 (d, J = 11.1 Hz, 1 H) |

5.4 Synthesis of 1-(2-{2-[3-(4-methyl-1,3-thiazol-2-yl)pyrrolidin-1-yl]ethyl}phenyl) piperidin-2-one oxalate 87

At 0° C., 1-[2-(2-{(methoxymethyl)[(trimethylsilyl)methyl]amino}ethyl)phenyl]piperidin-2-one a5-2 (696 mg, 2 mmol, 2 eq) is slowly added to 2-ethenyl-4-methyl-1,3-thiazole a5-3 (125 mg, 1 mmol, 1 eq) diluted in dichloromethane/TFA (90 μl/10 μl). The mixture is stirred at room temperature overnight. Solvent is removed under reduced pressure and the residue is purified by basic reverse phase chromatography on silicagel (gradient: acetonitrile/H$_2$O/NH$_4$OH from 30/70/0.1 to 60/40/0.1 in 10 minutes). The product is dissolved in a minimum of acetone and oxalic acid (1 eq) is added to form the salt that is filtered, washed with diethyl ether and dried under vacuum to afford 215 mg of 1-(2-{2-[3-(4-methyl-1,3-thiazol-2-yl)pyrrolidin-1-yl]ethyl}phenyl)piperidin-2-one oxalate 87.

Yield: 47%.

LC-MS (MH$^+$): 370.

Compounds 64, 74, 82, 83 and 84 may be synthesized according to the same method.

Example 6

Synthesis of 2-(1-{2-[2-(2-oxopiperidin-1-yl)phenyl]ethyl}piperidin-3-yl)benzamide oxalate 4

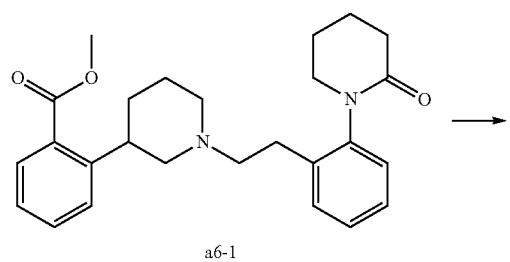

a6-1

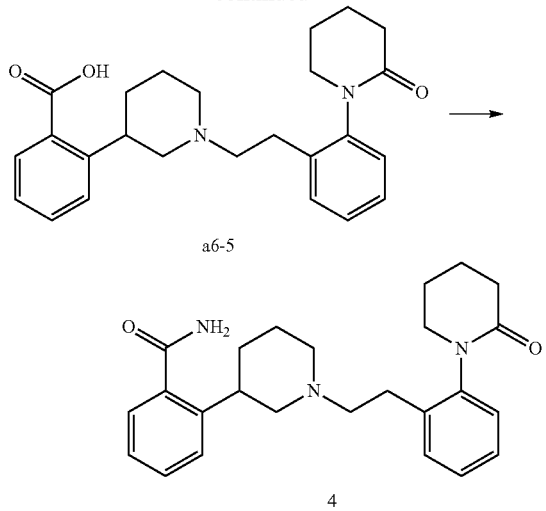

6.1 Synthesis of methyl 2-(1-{2-[2-(2-oxopiperidin-1-yl)phenyl]ethyl}piperidin-3-yl)benzoate a6-1

Methyl 2-(1-{2-[2-(2-oxopiperidin-1-yl)phenyl]ethyl}piperidin-3-yl)benzoate a6-1 may be prepared according to the procedure described in example 2.4.

LC-MS (MH$^+$): 421.

This is also the case of the following compounds:

| a6-2 | methyl 2-(1-{2-[2-(2-oxopiperidin-1-yl)phenyl]ethyl}pyrrolidin-3-yl)benzoate | LC-MS (MH$^+$): 407 |
|---|---|---|
| a6-3 | methyl 2-(1-{2-[2-(2-oxopiperidin-1-yl)phenyl]ethyl}pyrrolidin-3-yl)benzoate enantiomer 1 | LC-MS (MH$^+$): 407 |
| a6-4 | methyl 2-(1-{2-[2-(2-oxopiperidin-1-yl)phenyl]ethyl}pyrrolidin-3-yl)benzoate enantiomer 1 | LC-MS (MH$^+$): 407 |

6.2 Synthesis of 2-(1-{2-[2-(2-oxopiperidin-1-yl)phenyl]ethyl}piperidin-3-yl)benzoic acid a6-5

Methyl 2-(1-{2-[2-(2-oxopiperidin-1-yl)phenyl]ethyl}piperidin-3-yl)benzoate a6-1 (0.35 g, 0.84 mmol, 1 eq) is dissolved in methanol (5 ml). NaOH 5N (0.84 ml, 4.20 mmol, 5 eq) is added and the mixture is heated at 80° C. for 16 h. The reaction mixture is concentrated under reduced pressure and the residue obtained is taken up in MeOH, filtered, and evaporated to afford 0.34 g of crude 2-(1-{2-[2-(2-oxopiperidin-1-yl)phenyl]ethyl}piperidin-3-yl)benzoic acid a6-5 which is used in the next step without further purification.

Yield: assumed quantitative.

LC-MS (MH$^+$): 407.

The following intermediates may be synthesized according to the same method.

| a6-6 | 2-(1-{2-[2-(2-oxopiperidin-1-yl)phenyl]ethyl}pyrrolidin-3-yl)benzoic acid | LC-MS (MH$^+$): 393 |
|---|---|---|
| a6-7 | 2-(1-{2-[2-(2-oxopiperidin-1-yl)phenyl]ethyl}pyrrolidin-3-yl)benzoic acid enantiomer 1 | LC-MS (MH$^+$): 393 |
| a6-8 | 2-(1-{2-[2-(2-oxopiperidin-1-yl)phenyl]ethyl}pyrrolidin-3-yl)benzoic acid enantiomer 2 | LC-MS (MH$^+$): 393 |

6.3 Synthesis of 2-(1-{2-[2-(2-oxopiperidin-1-yl)phenyl]ethyl}piperidin-3-yl)benzamide oxalate 4

2-(1-{2-[2-(2-oxopiperidin-1-yl)phenyl]ethyl}piperidin-3-yl)benzoic acid a6-5 (0.34 g, 0.84 mmol, 1 eq) is dissolved in dry dichloromethane. Gaseous ammonia is bubbled through the solution for 15 min at 0° C. BOP (0.56 g, 1.27 mmol, 1.5 eq) is added and the mixture allowed to warm to room temperature overnight while a stream of ammonia is maintained. The mixture is evaporated to dryness and redissolved in dichloromethane. The organic layer is washed with 10% aqueous NaHCO3, dried over MgSO4 and concentrated under vacuum. The residue is purified by reverse phase HPLC (gradient: acetonitrile/H₂O/TFA from 20/80/0.1 to 50/50/0.1). The solution is catched over an acidic column, washed with methanol and then released with ammonia 1M in methanol. The solvent is evaporated under reduced pressure. The residue is recrystallized from ethyl acetate as an oxalic acid salt to afford 62 mg of 2-(1-{2-[2-(2-oxopiperidin-1-yl)phenyl]ethyl}piperidin-3-yl)benzamide oxalate 4.

Yield: 15%.
LC-MS (MH⁺): 406.

Example 7

Synthesis of N-methyl-2-(1-{2-[2-(2-oxopiperidin-1-yl)phenyl]ethyl}pyrrolidin-3-yl)benzamide oxalate 2

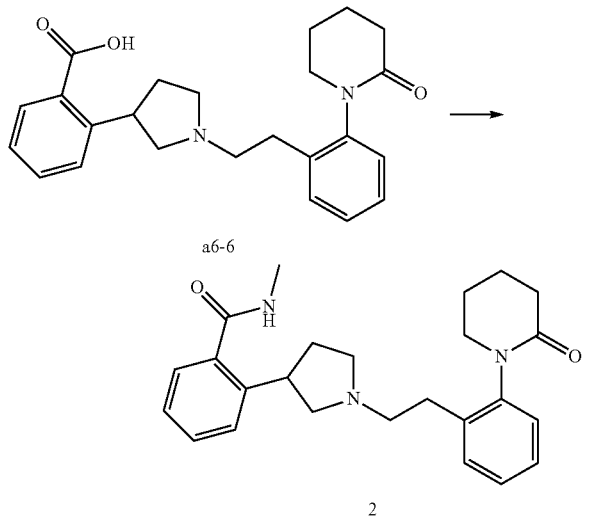

a6-6

2

2-(1-{2-[2-(2-oxopiperidin-1-yl)phenyl]ethyl}pyrrolidin-3-yl)benzoic acid a6-6 (0.67 g, 1.71 mmol, 1 eq) is dissolved in dichloromethane (13 ml). Gaseous MeNH₂ is bubbled through the solution for 5 min at 0° C. BOP (1.13 g, 2.56 mmol, 1.5 eq) is added and a stream of MeNH₂ was maintained for 5 min. The mixture is allowed to warm up to room temperature, stirred overnight, and then concentrated under vacuum. The residue is redissolved in dichloromethane, the organic layer is washed with a solution of 10% aqueous NaHCO₃, dried over MgSO₄ and concentrated under reduced pressure. The residue obtained is purified by chromatography over silicagel (eluent: CH₂Cl₂/MeOH/NH₄OH 94/6/0.6) followed by reverse phase HPLC (gradient: acetonitrile/H₂O/NH₄OH (aqueous, 0.1%) from 30/60/10 to 60/30/10 in 15 minutes). The residue is recrystallized from ethyl acetate as an oxalic acid salt to afford 250 mg of N-methyl-2-(1-{2-[2-(2-oxopiperidin-1-yl)phenyl]ethyl}pyrrolidin-3-yl)benzamide oxalate 2.

Yield: 36%.
LC-MS (MH⁺): 406.

Example 8

Synthesis of 1-[2-(2-{3-[2-(3-methyl-1,2,4-oxadiazol-5-yl)phenyl]pyrrolidin-1-yl}ethyl)phenyl]piperidin-2-one 11

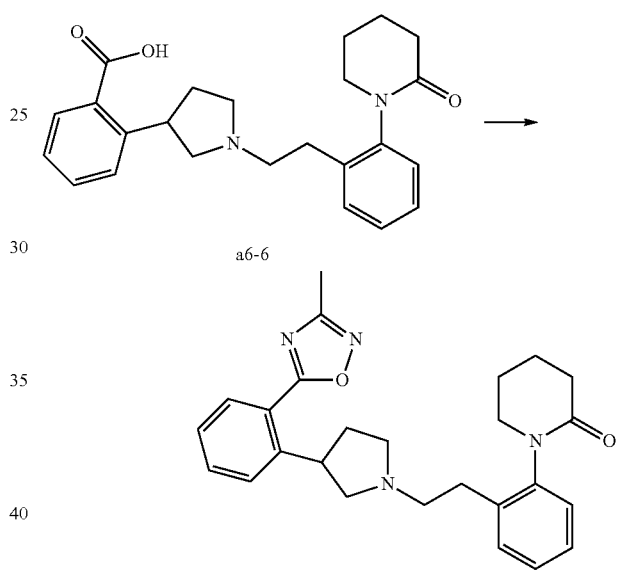

a6-6

11

2-(1-{2-[2-(2-oxopiperidin-1-yl)phenyl]ethyl}pyrrolidin-3-yl)benzoic acid a6-6 (0.31 g, 0.79 mmol, 1 eq) is dissolved in DMF and N,N'-carbonyldiimidazole (140 mg, 0.87 mmol, 1.1 eq) is added. The mixture is stirred at room temperature for 30 min, N-hydroxyacetamidine hydrochloride (95 mg, 0.87 mmol, 1.1 eq) is added and stirring is pursued for 4 hours. Another 1.1 eq of N,N'-carbonyldiimidazole and 1.1 eq of N-hydroxyacetamidine hydrochloride are added and the reaction mixture is stirred at reflux overnight. Dichloromethane and water are added and the organic layer is subsequently washed with water, HCl 1N, aqueous saturated NaHCO₃ and brine. The organic layer is dried over MgSO₄, evaporated and purified by preparative basic LC/MS (gradient: H₂O/acetonitrile/NH₄HCO₃ 0.5% w/v from 85/5/10 to 5/95/0 in 6.5 minutes) to afford 19 mg of 1-[2-(2-{3-[2-(3-methyl-1,2,4-oxadiazol-5-yl)phenyl]pyrrolidin-1-yl}ethyl)phenyl]piperidin-2-one 11.

Yield: 6%.
LC-MS (MH⁺): 431.

Example 9

Synthesis of (−)-1-[2-(2-{3-[2-(pyrrolidin-1-ylcarbonyl)phenyl]pyrrolidin-1-yl}ethyl)phenyl]piperidin-2-one 17

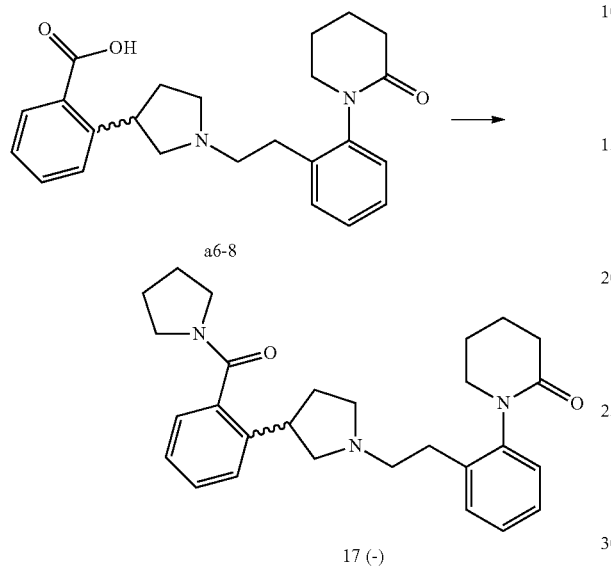

a6-8

17 (−)

2-(1-{2-[2-(2-oxopiperidin-1-yl)phenyl]ethyl}pyrrolidin-3-yl)benzoic acid enantiomer 2 a6-8 (2.72 g, 6.97 mmol, 1 eq) is dissolved in dichloromethane (100 ml). Pyrrolidine (0.69 ml, 8.36 mmol, 1.2 eq) is added followed by BOP reagent (Benzotriazole-1-yl-oxy-tris-(dimethylamino)-phosphonium hexafluorophosphate; 4.62 g, 10.45 mmol, 1.5 eq) and the reaction mixture is stirred at room temperature for 4 h. The mixture is evaporated to dryness, redissolved in dichloromethane and the organic layer is washed with HCl 1N and water, dried over MgSO$_4$ and evaporated. The residue is purified by reverse phase HPLC (gradient: acetonitrile/H$_2$O/ammonium formate from 5% to 95% of acetonitrile in 8 minutes) to afford 385 mg of (−)-1-[2-(2-{3-[2-(pyrrolidin-1-ylcarbonyl)phenyl]pyrrolidin-1-yl}ethyl)phenyl]piperidin-2-one 17.

Yield: 12%.

LC-MS (MH$^+$): 446.

Example 10

Synthesis of 4-[(1-{2-[2-(2-oxopiperidin-1-yl)phenyl]ethyl}pyrrolidin-3-yl)oxy]benzonitrile 50

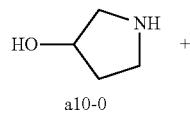

a10-0

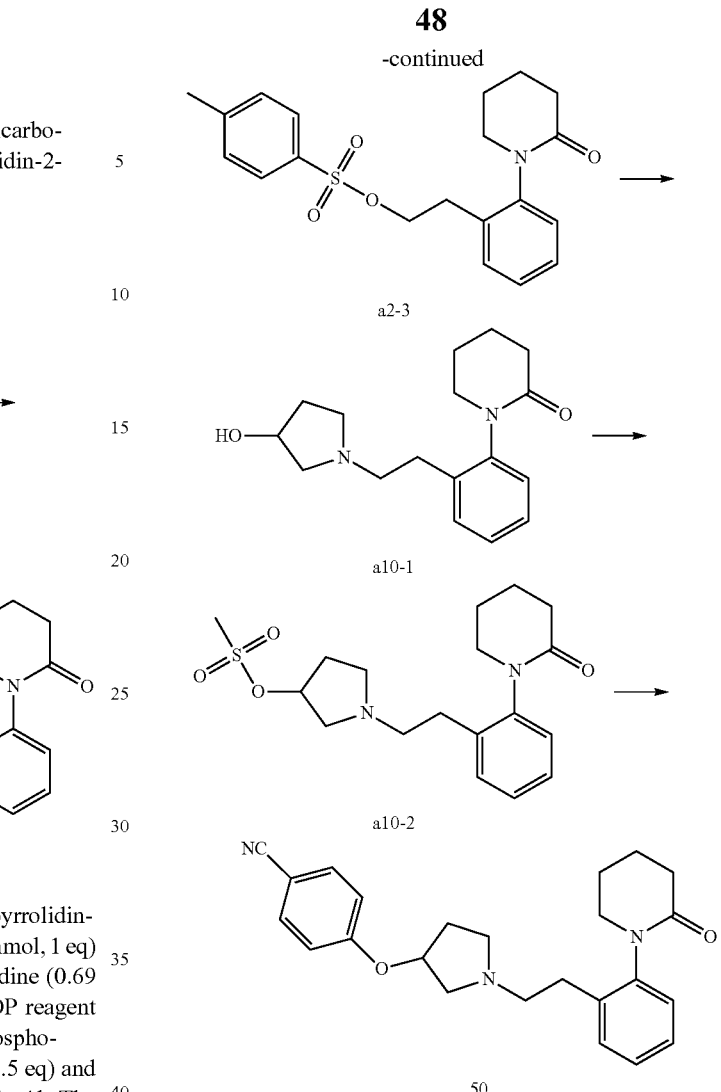

a2-3 a10-1 a10-2

50

10.1 Synthesis of 1-{2-[2-(3-hydroxypyrrolidin-1-yl)ethyl]phenyl}piperidin-2-one a10-1

To a solution of 2-[2-(2-oxopiperidin-1-yl)phenyl]ethyl 4-methyl benzenesulfonate a2-3 (11.95 g, 32 mmol, 1 eq) in acetonitrile (70 ml) is added K$_2$CO$_3$ (9.95 g, 48 mmol, 1.5 eq) then pyrrolidin-3-ol a10-0 (2.78 g, 32 mmol, 1 eq). The reaction mixture is stirred overnight at 85° C. After filtration on celite and solvent removal, the residue is purified by chromatography over silicagel (eluent: CH$_2$Cl$_2$/MeOH 93/7) to afford 6.68 g of 1-{2-[2-(3-hydroxypyrrolidin-1-yl)ethyl]phenyl}piperidin-2-one a10-1.

Yield: 72%.

LC-MS (MH$^+$): 289.

10.2 Synthesis of 1-{2-[2-(2-oxopiperidin-1-yl)phenyl]ethyl}pyrrolidin-3-yl methanesulfonate a10-2

To a stirred solution of 1-{2-[2-(3-hydroxypyrrolidin-1-yl)ethyl]phenyl}piperidin-2-one a10-1 (5.6 g, 19.5 mmol, 1 eq) in acetonitrile (50 ml) at room temperature is added dimethylaminopyridine (0.238 g, 1 mmol, 0.1 eq) and triethylamine (10.9 ml, 78 mmol, 4 eq). The solution is stirred at room temperature for 30 minutes. Mesyl chloride (4.5 ml, 59.5 mmol, 3 eq) is added to this solution. The reaction mixture is stirred at room temperature overnight. After solvent removal, the residue is redissolved in dichloromethane (250 ml) and the organic layer washed with water (100 ml), 1M HCl (120 ml) and water (250 ml). The combined aqueous phases are neutralised by addition of aqueous NaOH and extracted with dichloromethane (3×200 ml). The combined organic layers are dried over $MgSO_4$ and evaporated under vacuum. Purification of the residue obtained by chromatography over silicagel (eluent: $CH_2Cl_2$/MeOH/$NH_3$ 97/2.7/0.3) affords 5.07 g of pure 1-{2-[2-(2-oxopiperidin-1-yl)phenyl]ethyl}pyrrolidin-3-yl methanesulfonate a10-2.

Yield: 71%.
LC-MS (MH$^+$): 367.

10.3 Synthesis of 4-[(1-{2-[2-(2-oxopiperidin-1-yl)phenyl]ethyl}pyrrolidin-3-yl)oxy]benzonitrile 50

To a solution of 1-{2-[2-(2-oxopiperidin-1-yl)phenyl]ethyl}pyrrolidin-3-yl methanesulfonate a10-2 (0.183 g, 0.5 mmol, 1 eq) in acetonitrile (4 ml) is added $K_2CO_3$ (0.138 g, 1 mmol, 2 eq) and 4-hydroxybenzonitrile (0.060 g, 0.5 mmol, 1 eq). The solution is stirred overnight at 85° C. After filtration and solvent removal, the residue is purified by basic reverse phase chromatography on silicagel (gradient: $CH_3CN$/$H_2O$/$NH_4OH$ from 40/60/0.1 to 70/30/0.1) to give 85 mg of pure 4-[(1-{2-[2-(2-oxopiperidin-1-yl)phenyl]ethyl}pyrrolidin-3-yl)oxy]benzonitrile 50.

Yield: 43%.
LC-MS (MH$^+$): 390.

Example 11

Synthesis of 4-[(1-{2-[2-(2-oxopiperidin-1-yl)phenyl]ethyl}azetidin-3-yl)oxy]benzonitrile oxalate 55

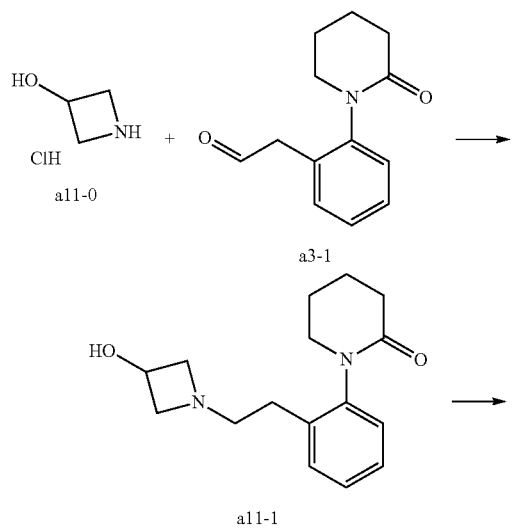

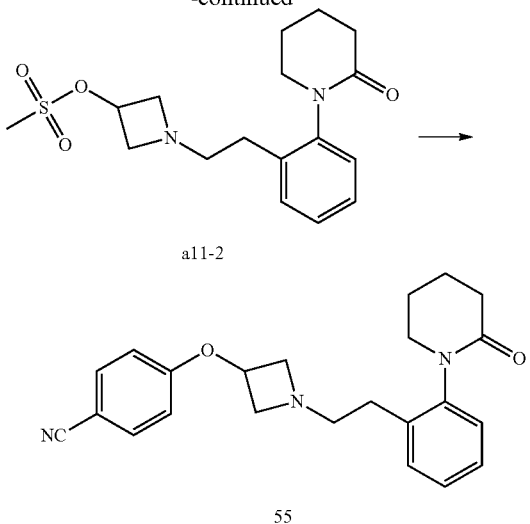

11.1 Synthesis of 1-{2-[2-(3-hydroxyazetidin-1-yl)ethyl]phenyl}piperidin-2-one a11-1

To [2-(2-oxopiperidin-1-yl)phenyl]acetaldehyde a3-1 (1.32 g, 6.09 mmol, 1 eq) in methanol (50 ml) is added azetidin-3-ol hydrochloride al 1-0 (0.76 g, 6.96 mmol, 1.14 eq). After stirring at room temperature for approximately 30 minutes, acetic acid (522 μl, 9.13 mmol, 1.5 eq), then $NaBH_3CN$ (1.15 g, 18.26 mmol, 3 eq) are added. The reaction mixture is stirred overnight at room temperature, then filtered and loaded on an ion exchange acidic resin cartridge prewashed with methanol. The cartridge is then washed with approximately 3 column volumes of methanol, then eluted with 3 column volumes of 1M ammonia in methanol. This eluate is evaporated to dryness. To the residue obtained is added water (50 ml) and dichloromethane (50 ml). After vigorous shaking and addition of brine, the 2 phases are separated. The organic phase is washed with water (50 ml). The aqueous phases are pooled and washed 3 times with iPrOH/$CH_2Cl_2$ (25 ml/50 ml). The organic phases are combined, evaporated to dryness to give 212.6 mg of 1-{2-[2-(3-hydroxyazetidin-1-yl)ethyl]phenyl}piperidin-2-one a11-1 (212.6 mg, 0.775 mmole if assumed pure, 12.7% yield), which is used in next step without any further purification.

Yield: 13%.
LC-MS (MH$^+$): 275.

11.2 Synthesis of 1-{2-[2-(2-oxopiperidin-1-yl)phenyl]ethyl}azetidin-3-yl methanesulfonate a11-2

To 1-{2-[2-(3-hydroxyazetidin-1-yl)ethyl]phenyl}piperidin-2-one a11-1 (212 mg, 0.77 mmol, 1 eq) in dichloromethane (15 ml) under nitrogen is added triethylamine (216.04 μl, 1.55 mmol, 2 eq). Methanesulfonyl chloride (106.53 mg, 0.93 mmol, 1.2 eq) is added at 0° C. and the reaction mixture is allowed to reach room temperature while stirring for 2 hours under a nitrogen atmosphere. Additional triethylamine (216 μl, 1.55 mmol, 2 eq) and methanesulfonyl chloride (106.53 mg, 0.93 mmol, 1.2 eq) are added, and the reaction mixture stirred at room temperature under nitrogen for an additional hour. Water (50 ml) is then added, the two phases vigorously shaken and separated. The organic phase is dried over $MgSO_4$, filtered and evaporated to dryness to give 1-{2-[2-(2-oxopiperidin-1-yl)phenyl]ethyl}azetidin-3-yl methanesulfonate a11-2 which is used in next step without any further purification.

Yield: assumed quantitative.

LC-MS (MH$^+$): 353.

11.3 Synthesis of 4-[(1-{2-[2-(2-oxopiperidin-1-yl)phenyl]ethyl}azetidin-3-yl)oxy]benzonitrile oxalate 55

To 1-{2-[2-(2-oxopiperidin-1-yl)phenyl]ethyl}azetidin-3-yl methanesulfonate a11-2 (273 mg, 0.775 mmol, 1 eq) and 4-hydroxybenzonitrile (110.8 mg, 0.93 mmol, 1.2 eq) in acetonitrile (5 ml) is added, under stirring, K$_2$CO$_3$ (374.9 mg, 2.71 mmol, 3.5 eq). The reaction mixture is heated at 100° C. for 10 minutes under microwave conditions. The reaction mixture is cooled, diluted with a mixture of acetonitrile/CH$_2$Cl$_2$/MeOH/DMF (1/1/1/1) (approximately 10 ml) to ensure the solubilisation of the expected product. The suspension obtained is loaded on an ion exchange acidic resin cartridge (2 g) prewashed with methanol. The cartridge is washed with approximately 3 column volumes of methanol, then eluted with 3 column volumes of 1M ammonia in methanol. The eluate is evaporated to dryness and the crude material is purified by reverse phase chromatography (gradient: acetonitrile//H$_2$O/NH$_4$OH from 40/60/0.1 to 70/30/0.1 in 10 minutes). The residue obtained is dissolved in acetone (approximately 2 ml) and oxalic acid (4.4 mg, 0.05 mmole, 1 eq) in acetone (2 ml) is added. This solution is evaporated slowly and some crystals appear. Acetone (approximately 2 ml) then diethylether (approximately 10 ml) are added to give a white precipitate which is filtrated, extensively washed with diethylether and dried overnight at 40° C. under vacuum to afford 15.5 mg of 4-[(1-{2-[2-(2-oxopiperidin-1-yl)phenyl]ethyl}azetidin-3-yl)oxy]benzonitrile oxalate 55.

Yield: 4.3% over 2 steps.

LC-MS (MH$^+$): 376.

Example 12

Synthesis of 1-(2-{2-[3-(1-acetylpiperidin-2-yl)pyrrolidin-1-yl]ethyl}phenyl)piperidin-2-one 72

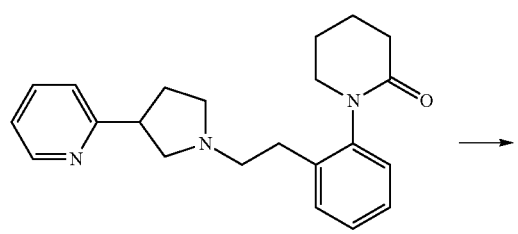

36

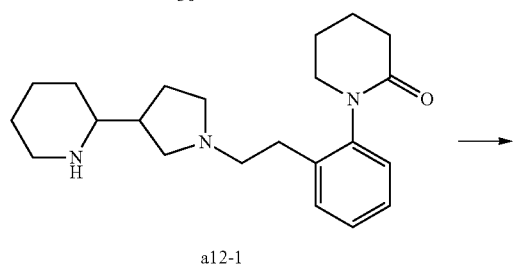

a12-1

-continued

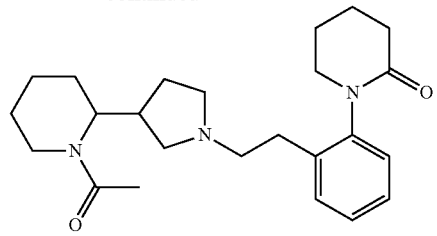

72

12.1 Synthesis of 1-(2-{2-[3-(piperidin-2-yl)pyrrolidin-1-yl]ethyl}phenyl)piperidin-2-one a12-1

1-(2-{2-[3-(pyridin-2-yl)pyrrolidin-1-yl]ethyl}phenyl)piperidin-2-one 36 (30 mg, 0.085 mmol, 1 eq) in glacial acetic acid is hydrogenated on PtO$_2$ at 40° C. and 40 Psi for 0.5 hour in a H-cube reactor. The solvent is removed under vacuum to afford 28 mg of crude 1-(2-{2-[3-(piperidin-2-yl)pyrrolidin-1-yl]ethyl}phenyl)piperidin-2-one a12-1 as a yellow oil which is used in the next step without any further purification.

Yield: 93%.

LC-MS (MH$^+$): 356.

12.2 Synthesis of 1-(2-{2-[3-(1-acetyl piperidin-2-yl) pyrrolidin-1-yl]ethyl}phenyl)piperidin-2-one 72

To a solution of 1-(2-{2-[3-(piperidin-2-yl)pyrrolidin-1-yl]ethyl}phenyl)piperidin-2-one a12-1 (25 mg, 0.070 mmol, 1 eq) in diethylether (2 ml) at 0° C. are added triethylamine and acetic anhydride (7 µl, 0.077 mmol, 1.1 eq). The mixture is stirred for 1 hour at room temperature. The solvent is removed under vacuum. The residue obtained is purified by basic reverse phase chromatography (gradient: acetonitrile/H$_2$O/ammonium formate from 5% to 95% of acetonitrile in 8 minutes) to afford 14.5 mg of 1-(2-{2-[3-(1-acetylpiperidin-2-yl)pyrrolidin-1-yl]ethyl}phenyl)piperidin-2-one 72 as a yellow oil.

Yield: 50%.

LC-MS (MH$^+$): 398.

Example 13

Synthesis of 1-(2-{2-[3-(2-fluoro-2-methylpropyl) pyrrolidin-1-yl]ethyl}phenyl)piperidin-2-one 85

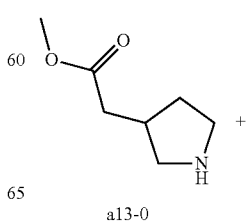

a13-0

+

-continued

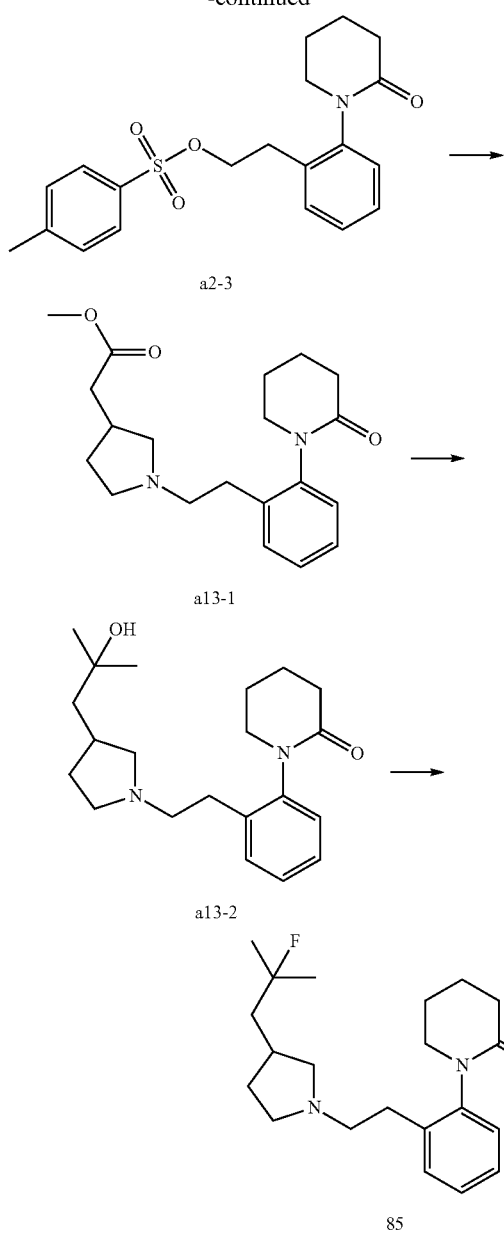

a2-3 a13-1 a13-2

85

13.1 Synthesis of methyl (1-{2-[2-(2-oxopiperidin-1-yl)phenyl]ethyl}pyrrolidin-3-yl)acetate a13-1

To a solution of 2-[2-(2-oxopiperidin-1-yl)phenyl]ethyl 4-methylbenzenesulfonate a2-3 (2.85 g, 7.65 mmol, 1 eq) in DMF (10 ml) at room temperature are added diisopropylethylamine (2.65 ml, 15.30 mmol, 2 eq) and methylpyrrolidin-3-ylacetate a13-0 (1.08 g, 7.65 mmol, 1 eq). The mixture is stirred at 80° C. overnight. The solvent is removed under vacuum. The residue obtained is purified by chromatography over silicagel (eluent: $CH_2Cl_2$/EtOH 95/5) to afford 1.05 g of methyl (1-{2-[2-(2-oxopiperidin-1-yl)phenyl]ethyl}pyrrolidin-3-yl)acetate a13-1 as a yellow oil.

Yield: 42%.

LC-MS (MH$^+$): 345.

13.2 Synthesis of 1-(2-{2-[3-(2-hydroxy-2-methyl-propyl)pyrrolidin-1-yl]ethyl}phenyl)piperidin-2-one a13-2

Methyl (1-{2-[2-(2-oxopiperidin-1-yl)phenyl]ethyl}pyrrolidin-3-yl)acetate a13-1 (0.15 g, 0.435 mmol, 1 eq) is dissolved in THF (5 ml). MeMgBr (3M in diethylether, 435 ml, 1.3 mmol, 3 eq) is added dropwise at 0° C. The reaction mixture is stirred at room temperature for 1 hour, and then quenched with saturated aqueous $NH_4Cl$. The two phases are separated, the aqueous layer is further extracted with AcOEt (3×20 ml), the pooled organic phases are then washed with brine (20 ml), dried with $Na_2SO_4$ and concentrated under reduced pressure to afford 54 mg of 1-(2-{2-[3-(2-hydroxy-2-methylpropyl)pyrrolidin-1-yl]ethyl}phenyl)piperidin-2-one a13-2 as a yellow oil which is used in the next step without any further purification.

Yield: 36%.

LC-MS (MH$^+$): 345.

13.3 Synthesis of 1-(2-{2-[3-(2-fluoro-2-methylpropyl)pyrrolidin-1-yl]ethyl}phenyl) piperidin-2-one 85

Diethylaminosulfur trifluoride (31 µl, 0.235 mmol, 1.5 eq) is added to 1-(2-{2-[3-(2-hydroxy-2-methyl propyl)pyrrolidin-1-yl]ethyl}phenyl)piperidin-2-one a13-2 (54 mg, 0.157 mmol, 1 eq) in dichloromethane (5 ml) dropwise and the reaction mixture stirred at room temperature overnight. The reaction mixture is poured into water and stirring is pursued for 1 hour. After phase separation, the aqueous phase is further extracted with dichloromethane (3 times). The combined organic phases are washed with brine (1 time), dried over $Na_2SO_4$, filtered and concentrated under reduced pressure. The residue is purified by basic reverse phase chromatography (gradient: acetonitrile/$H_2O$/ammonium formiate from 5% to 40% of acetonitrile in 8 minutes) to afford 6 mg of 1-(2-{2-[3-(2-fluoro-2-methylpropyl)pyrrolidin-1-yl]ethyl}phenyl)piperidin-2-one 85 as a yellow oil.

Yield: 65%.

LC-MS (MH$^+$): 347.

Example 14

Synthesis of 1-[2-(2-{3-[2-oxo-2-(pyrrolidin-1-yl)ethyl]pyrrolidin-1-yl}ethyl)phenyl]piperidin-2-one 86

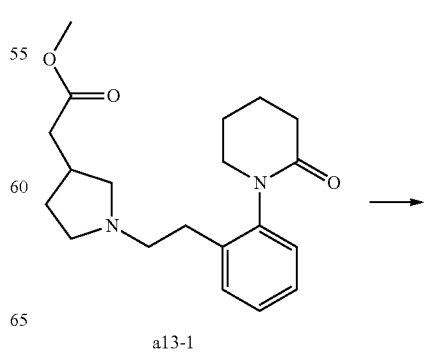

a13-1

-continued

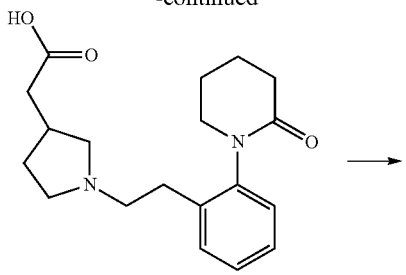

a14-1

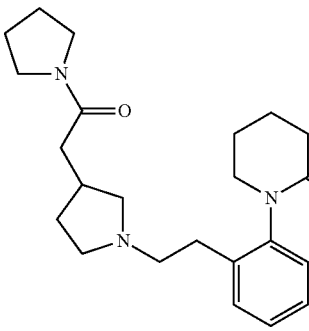

86

14.1 Synthesis of (1-{2-[2-(2-oxopiperidin-1-yl)phenyl]ethyl}pyrrolidin-3-yl)acetic acid a14-1

Methyl (1-{2-[2-(2-oxopiperidin-1-yl)phenyl]ethyl}pyrrolidin-3-yl)acetate a13-1 (500 mg, 0.87 mmol, 1 eq) is dissolved in MeOH/H$_2$O (4 ml/1 ml) and LiOH (47 mg, 1.7 mmol, 2 eq) is added. The reaction mixture is stirred at 30° C. for 1 hour, then quenched with HCl 1M (100 μl). The resulting mixture is diluted with n-butanol (15 ml), and stirred overnight at room temperature. After phase separation the organic layer is dried on Na$_2$SO$_4$, filtered and the filtrate is concentrated under reduced pressure to afford 229 mg of (1-{2-[2-(2-oxopiperidin-1-yl)phenyl]ethyl}pyrrolidin-3-yl)acetic acid a14-1 as a colorless oil which is used in the next step without any further purification.

Yield: 80%.
LC-MS (MH$^+$): 331.

14.2 Synthesis of 1-[2-(2-{3-[2-oxo-2-(pyrrolidin-1-yl)ethyl]pyrrolidin-1-yl}ethyl)phenyl]piperidin-2-one 86

To (1-{2-[2-(2-oxopiperidin-1-yl)phenyl]ethyl}pyrrolidin-3-yl)acetic acid a14-1 (115 mg, 0.348 mmol, 1 eq) and pyrrolidine (32 μl, 0.382 mmol 1.1 eq) in dichloromethane (5 ml) are added dicyclohexylcarbodiimide (79 mg, 0.82 mmol, 1.1 eq), hydroxybenzotriazole (52 mg, 0.382 mmol, 1.1 eq) and diisopropylethylamine (131 μl, 0.731 mmol, 2.1 eq). The reaction mixture is stirred overnight at room temperature, then filtered and concentrated under reduced pressure. The residue is purified by reverse phase chromatography (gradient: CH$_3$CN/H$_2$O/NH$_4$OH from 30/70/0.1 to 60/40/0.1) to afford 9 mg of 1-[2-(2-{3-[2-oxo-2-(pyrrolidin-1-yl)ethyl]pyrrolidin-1-yl}ethyl)phenyl]piperidin-2-one 86 as a yellow oil.

Yield: 7%.
LC-MS (MH$^+$): 384.

Example 15

Synthesis of 1-[3-(2-{3-[6-(2,2,2-trifluoroethoxy)pyridin-2-yl]pyrrolidin-1-yl}ethyl)pyridin-2-yl]piperidin-2-one 108

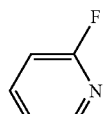

a15-1

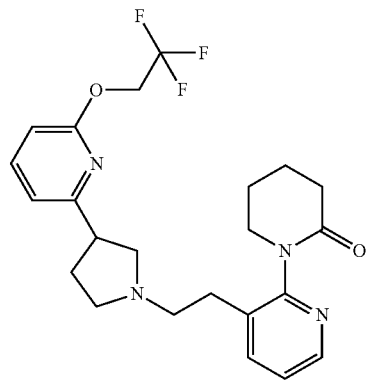

108

15.1 Synthesis of 1-(3-{2-[3-(6-fluoropyridin-2-yl)pyrrolidin-1-yl]ethyl}pyridin-2-yl)piperidin-2-one a15-1

1-(3-{2-[3-(6-fluoropyridin-2-yl)pyrrolidin-1-yl]ethyl}pyridin-2-yl)piperidin-2-one a15-1 may be prepared according to the procedure described in example 4.4.
LC-MS (MH$^+$): 369.

15.2 Synthesis of 1-[3-(2-{3-[6-(2,2,2-trifluoroethoxy)pyridin-2-yl]pyrrolidin-1-yl}ethyl)pyridin-2-yl]piperidin-2-one 108

1-(3-{2-[3-(6-fluoropyridin-2-yl)pyrrolidin-1-yl]ethyl}pyridin-2-yl)piperidin-2-one a15-1 (32 mg, 0.087 mmol, 1 eq), 2,2,2-trifluoroethanol (13 mg, 0.13 mmol, 1.5 eq) and t-BuOK (48.8 mg, 0.43 mmol, 5 eq) are dissolved in DMSO. The reaction mixture is stirred at room temperature. After 2 hours, 2,2,2-trifluoroethanol (8.7 mg, 0.087 mmol, 1 eq) is added and the reaction mixture is stirred overnight. Ethyl acetate and aqueous saturated NaCl solution are then added, the two phases separated and the aqueous layer is reextracted with ethyl acetate (3 times). The organic layers are pooled, dried with MgSO$_4$, filtered and condensed under reduced pressure. The residue is purified by basic reverse phase chromatography (gradient: water/acetonitrile/solvent C from 90/0/10 to 5/85/10 in 10 minutes; solvent C: acetonitrile/water 1/1+NH$_4$CO$_3$ 0.4% w/v and NH$_4$OH 0.05% v/v) to afford 11.7 mg of 1-[3-(2-{3-[6-(2,2,2-trifluoroethoxy)pyridin-2-yl]pyrrolidin-1-yl}ethyl)pyridin-2-yl]piperidin-2-one 108.
Yield: 30%.
LC-MS (MH$^+$): 449.

Example 16

Synthesis of 1-[3-(2-{3-[6-(difluoromethoxy)pyridin-2-yl]pyrrolidin-1-yl}ethyl)pyridin-2-yl]piperidin-2-one 109

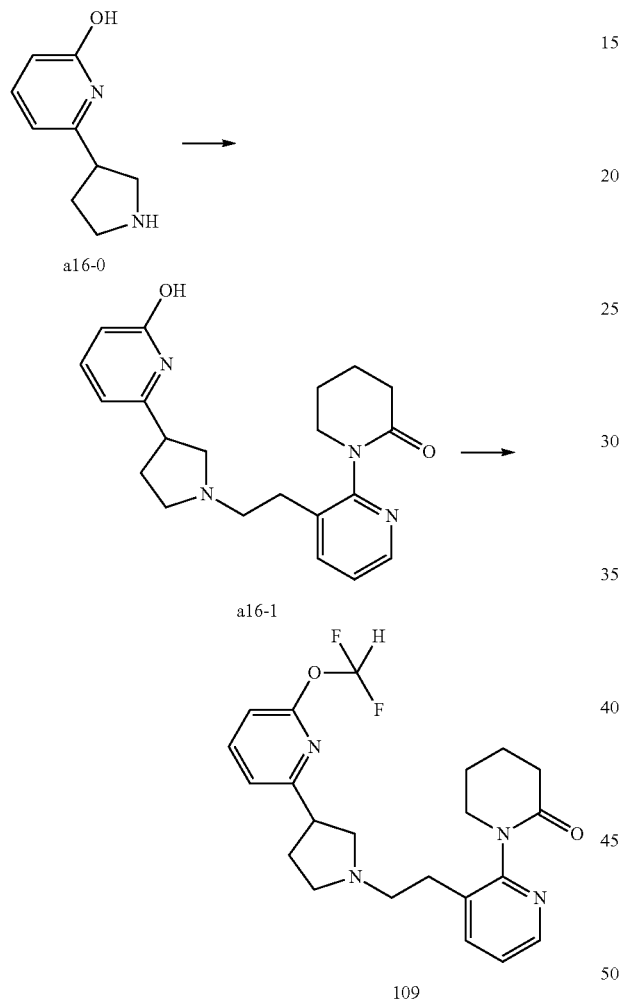

16.1 Synthesis of 1-(3-{2-[3-(6-hydroxypyridin-2-yl)pyrrolidin-1-yl]ethyl}pyridin-2-yl)piperidin-2-one a16-1

1-(3-{2-[3-(6-hydroxypyridin-2-yl)pyrrolidin-1-yl]ethyl}pyridin-2-yl)piperidin-2-one a16-1 may be prepared from 6-(pyrrolidin-3-yl)pyridin-2-ol a16-0 according to the method described in example 4.4.
Yield: 46%.
LC-MS (MH$^+$): 367.

16.2 Synthesis of 1-[3-(2-{3-[6-(difluoromethoxy)pyridin-2-yl]pyrrolidin-1-yl}ethyl)pyridin-2-yl]piperidin-2-one 109

2,2-Difluoro-2-(fluorosulfonyl)acetic acid (9.72 mg, 0.054 mmol, 1 eq) is added slowly, under stirring, to a mixture of 1-(3-{2-[3-(6-hydroxypyridin-2-yl)pyrrolidin-1-yl]ethyl}pyridin-2-yl)piperidin-2-one a16-1 (20 mg, 0.054 mmol, 1 eq) and dry sodium sulfate (0.78 mg, 0.005 mmol, 0.1 eq) in dry acetonitrile (400 µl). The reaction is stirred for 2 h at room temperature, then water (100 µl) is added. The resulting solution is concentrated in vacuo. The residue is purified by basic reverse phase chromatography (gradient: H$_2$O/acetonitrile/NH$_4$OH from 50/50/0.1 to 20/80/0.1) to afford 9.4 mg of 1-[3-(2-{3-[6-(difluoromethoxy)pyridin-2-yl]pyrrolidin-1-yl}ethyl)pyridin-2-yl]piperidin-2-one 109.
Yield: 41%.
LC-MS (MH$^+$): 417.

Example 17

Synthesis of 1-[1-methyl-4-(2-{3-[4-(trifluoromethyl)phenyl]pyrrolidin-1-yl}ethyl)-1H-pyrazol-3-yl]piperidin-2-one oxalate 111

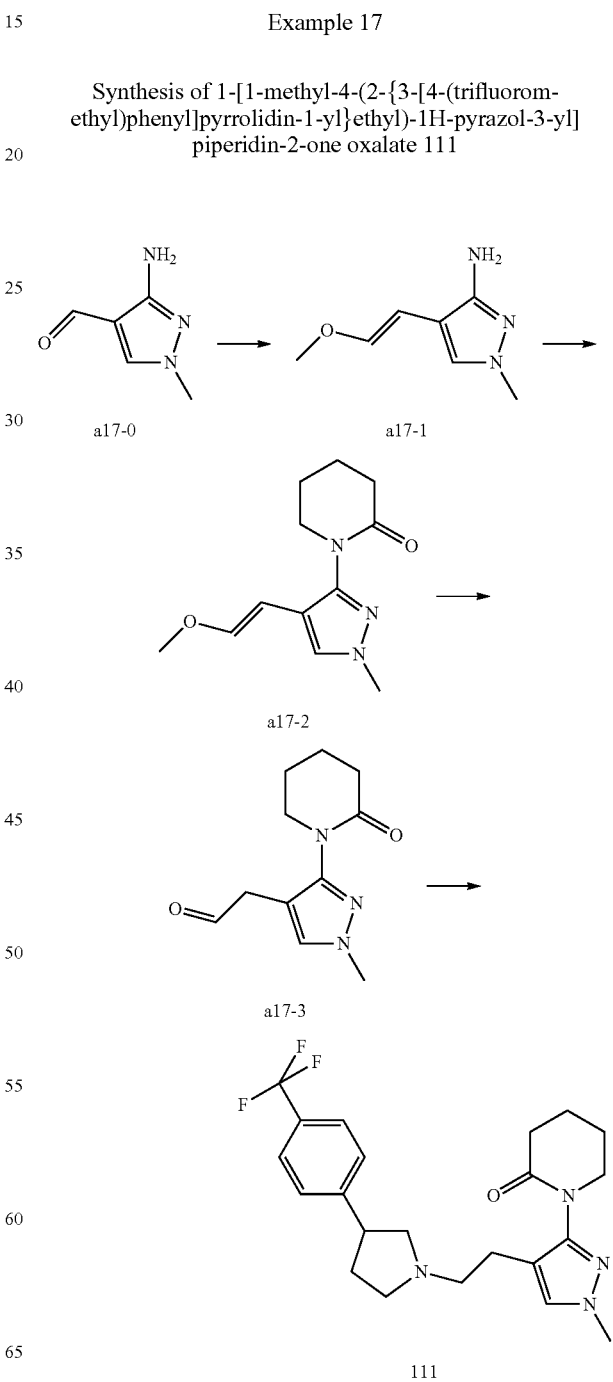

17.1 Synthesis of 4-(2-methoxyvinyl)-1-methyl-1H-pyrazol-3-amine a17-1

4-(2-methoxyvinyl)-1-methyl-1H-pyrazol-3-amine a17-1 may be prepared from 3-amino-1-methyl-1H-pyrazole-4-carbaldehyde a17-0 according to the procedure described in example 4.2.

Yield: assumed quantitative.
LC-MS (MH+): 154.

17.2 Synthesis of 1-[4-(2-methoxyvinyl)-1-methyl-1H-pyrazol-3-yl]piperidin-2-one a17-2

A mixture of 4-(2-methoxyvinyl)-1-methyl-1H-pyrazol-3-amine a17-1 (500 mg, 3.27 mmol, 1 eq), 5-bromovaleryl chloride (651.9 mg, 3.27 mmol, 1 eq), potassium hydroxide (550.1 mg, 9.80 mmol, 3 eq), 4-dimethymaminopyridine (39.9 mg, 0.33 mmole, 0.1 eq) and N,N,N-tributylbutan-1-aminium bromide (105.3 mg, 0.33 mmole, 0.1 eq) in toluene (15 ml) is heated to reflux overnight. After filtration and evaporation the residue is purified by reverse phase chromatography (basic mode, gradient: H$_2$O/acetonitrile/NH$_4$OH from 80/20/0.1 to 50/50/0.1 in 10 minutes) to afford 1-[4-(2-methoxyvinyl)-1-methyl-1H-pyrazol-3-yl]piperidin-2-one a17-2.

LC-MS (MH+): 236.

17.3 Synthesis of [1-methyl-3-(2-oxopiperidin-1-yl)-1H-pyrazol-4-yl]acetaldehyde a17-3

[1-methyl-3-(2-oxopiperidin-1-yl)-1H-pyrazol-4-yl]acetaldehyde a17-3 may be prepared from 1-[4-(2-methoxyvinyl)-1-methyl-1H-pyrazol-3-yl]piperidin-2-one a17-2 according to the procedure described in example 4.3.

17.4 Synthesis of 1-[1-methyl-4-(2-{3-[4-(trifluoromethyl)phenyl]pyrrolidin-1-yl}ethyl)-1H-pyrazol-3-yl]piperidin-2-one oxalate 111

1-[1-methyl-4-(2-{3-[4-(trifluoromethyl)phenyl]pyrrolidin-1-yl}ethyl)-1H-pyrazol-3-yl]piperidin-2-one oxalate 111 may be prepared from [1-methyl-3-(2-oxopiperidin-1-yl)-1H-pyrazol-4-yl]acetaldehyde a17-3 according to the procedure described in example 4.4.

Yield: 39% from a17-2 (over 2 steps).
LC-MS (MH+): 421.

Example 18

Synthesis of 1-[3-{2-[3-(pyridin-2-yl)pyrrolidin-1-yl]ethyl}-5-(trifluoromethyl)pyridin-2-yl]piperidin-2-one 110

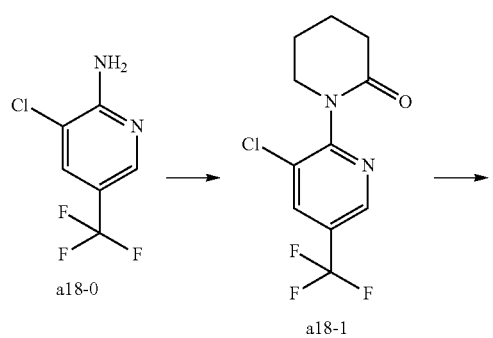

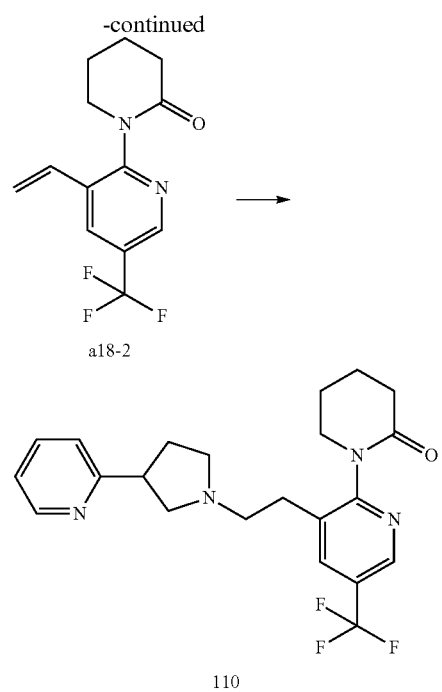

18.1 Synthesis of 1-[3-chloro-5-(trifluoromethyl)pyridin-2-yl]piperidin-2-one al 8-1

To a solution of 3-chloro-5-(trifluoromethyl)pyridin-2-amine a18-0 (700 mg, 3.54 mmol, 1 eq) in dry THF (15 ml) cooled at 0° C. is added NaH 60% in mineral oil (283 mg, 7.08 mmol, 2 eq). The reaction mixture is stirred at 0° C. for 10 minutes then at room temperature for 20 minutes. The reaction mixture is then cooled down to 0° C. and 5-bromovaleryl chloride (707 mg, 3.543 mmol, 1 eq) is added. The reaction mixture is stirred at 70° C. for 3 hours then evaporated to dryness. The residue obtained is retaken in dichloromethane, washed with aqueous NH$_4$Cl (1 time), washed with saturated aqueous NaHCO$_3$ (1 time). The organic phase is dried over MgSO$_4$, filtered and evaporated to dryness. The residue obtained is purified by flash chromatography over silicagel (24 g, gradient: dichloromethane/MeOH from 100/0 to 94/6) to afford 480 mg of 1-[3-chloro-5-(trifluoromethyl)pyridin-2-yl]piperidin-2-one al 8-1.

Yield: 49%.
LC-MS (MH+): 279/281.

18.2 Synthesis of 1-[5-(trifluoromethyl)-3-vinylpyridin-2-yl]piperidin-2-one al 8-2

To a solution of 1-[3-chloro-5-(trifluoromethyl)pyridin-2-yl]piperidin-2-one al 8-1 (260 mg, 0.933 mmol, 1 eq) and vinylboronic acid pinacol ester (287 mg, 1.866 mmol, 2 eq) in a mixture of acetonitrile/water (3/2) is added tripotassium phosphate (793 mg, 3.732 mmol, 2 eq), (2,6-dimethoxy-1,1'-biphenyl-2-yl)dicyclohexylphosphine (77 mg, 0.187 mmol, 0.2 eq), Palladium(II) acetate (21 mg, 0.093 mmol, 0.1 eq) and the reaction mixture is heated at 120° C. for 40 minutes. After evaporation the residue is retaken in dichloromethane, this organic phase is washed with saturated aqueous NaHCO$_3$ (2 times), dried over MgSO$_4$, filtered and evaporated to dryness. The residue obtained is purified by flash chromatography over silicagel (12 g; gradient: dichloromethane/MeOH from 100/0 to 94/6) to afford 380 mg of 1-[5-(trifluoromethyl)-3-vinylpyridin-2-yl]piperidin-2-one a18-2.

Yield: assumed quantitative.

LC-MS (MH+): 271.

18.3 Synthesis of 1-[3-{2-[3-(pyridin-2-yl)pyrrolidin-1-yl]ethyl}-5-(trifluoromethyl)pyridin-2-yl]piperidin-2-one 110

To a solution of 1-[5-(trifluoromethyl)-3-vinylpyridin-2-yl]piperidin-2-one a18-2 (310 mg, 1.147 mmol, 1 eq) and 2-pyrrolidin-3-yl pyridine (221 mg, 1.491 mmol, 1.3 eq) in ethanol (10 ml) is added triethylamine (348 mg, 479 µl, 3.441 mmol, 3 eq). The reaction mixture is stirred at 90° C. for 7 hours, then heated overnight at 85° C. The reaction mixture is evaporated to dryness and retaken in dichloromethane. This organic phase is washed with aqueous NH$_4$Cl (1 time), saturated aqueous NaHCO$_3$ (2 times), then dried over MgSO$_4$, filtered and evaporated to dryness. The residue obtained is purified by flash chromatography over silicagel (12 g; gradient: from dichloromethane/MeOH 100/0 to 94/6), dried under vacuum to afford 91.4 mg of 1-[3-{2-[3-(pyridin-2-yl)pyrrolidin-1-yl]ethyl}-5-(trifluoromethyl)pyridin-2-yl]piperidin-2-one 110.

Yield: 19%.

LC-MS (MH+): 419.

Example 19

Synthesis of 1-(5-fluoro-3-{2-[3-(pyridin-2-yl)pyrrolidin-1-yl]ethyl}pyridin-2-yl)piperidin-2-one (80/20 mixture of enantiomers) 112

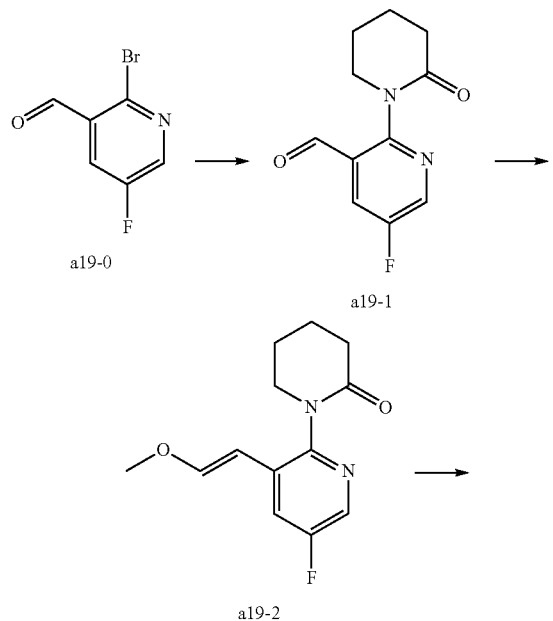

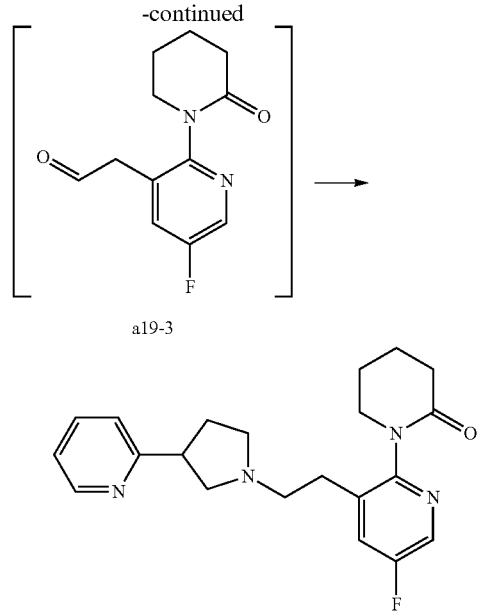

19.1 Synthesis of 5-fluoro-2-(2-oxopiperidin-1-yl)nicotinaldehyde a19-1

5-Fluoro-2-(2-oxopiperidin-1-yl)nicotinaldehyde a19-1 may be prepared from 2-bromo-5-fluoronicotinaldehyde a19-0 according to the procedure described in example 4.1.

Yield: assumed quantitative.

LC-MS (MH+): 223.

19.2 Synthesis of 1-[5-fluoro-3-(2-methoxyvinyl)pyridin-2-yl]piperidin-2-one a19-2

1-[5-Fluoro-3-(2-methoxyvinyl)pyridin-2-yl]piperidin-2-one a19-2 may be prepared from 5-fluoro-2-(2-oxopiperidin-1-yl)nicotinaldehyde a19-1 according to the procedure described in example 4.2.

Yield: 80%.

LC-MS (MH+): 251.

19.3 Synthesis of 1-(5-fluoro-3-{2-[3-(pyridin-2-yl)pyrrolidin-1-yl]ethyl}pyridin-2-yl)piperidin-2-one (80/20 mixture of enantiomers) 112

To a solution of 1-[5-fluoro-3-(2-methoxyvinyl)pyridin-2-yl]piperidin-2-one a19-2 (620 mg, 2.477 mmol, 1 eq) in acetonitrile (25 ml) is added at 0° C. sodium iodide (557 mg, 3.716 mmol, 1.5 eq) and trimethylsilyl chloride (404 mg, 3.716 mmol, 1.5 eq), and the reaction mixture is stirred at room temperature for 16 hours to form in situ [5-fluoro-2-(2-oxopiperidin-1-yl)pyridin-3-yl]acetaldehyde a19-3. In parallel, 2-(pyrrolidin-3-yl)pyridine enantiomer 2 dihydrochloride a1-67 (654 mg, 2.973 mmol, 1.2 eq) is dissolved in acetonitrile, loaded on a carbonate resin, the resin washed with dichloromethane and the pooled filtrates are evaporated to dryness to afford 2-(pyrrolidin-3-yl)pyridine enantiomer 2 as a free base. The residue obtained is added to intermediate a19-3. NaBH(OAc)$_3$ (1050 mg, 4.954 mmol, 2 eq) is added, the reaction mixture is stirred overnight and is still incomplete. Racemic 2-(pyrrolidin-3-yl)pyridine (0.4 eq) is added, the reaction mixture heated overnight at 90° C. and evaporated to dryness. The residue of evaporation is retaken in dichloromethane. This organis phase is washed with saturated aqueous NaHCO$_3$ (2 times), dried over MgSO$_4$, filtered and evaporated to dryness. The residue obtained is dissolved in acetonitrile (12 ml), HCl 5M (approximately 4 ml) is added and the mixture is stirred at 40° C. for 3 hours. Dichloromethane is then added, and the organic phase washed with saturated aqueous NaHCO$_3$ (2 times), dried over MgSO$_4$, filtered and evaporated to dryness. This residue is purified by flash chromatography over silicagel (12 g; gradient: from CH$_2$Cl$_2$/MeOH 100/0 to 94/6), then by reverse phase chromatography (basic conditions: gradient: acetonitrile/H$_2$O/NH$_4$OH from 20/80/0.1 to 50/50/0.1) to afford 38 mg of 1-(5-fluoro-3-{2-[3-(pyridin-2-yl)pyrrolidin-1-yl]ethyl}pyridin-2-yl)piperidin-2-one 112 as a 80/20 mixture of enantiomers.

Yield: 4.2%.

LC-MS (MH$^+$): 369.

Table (I) indicates the IUPAC name of the compound, the ion peak observed in mass spectroscopy, the 1H NMR description, the melting point or onset on DSC, and the alphaD.

TABLE I

Physical Characterization of Example Compounds.

| n° | ADDUCT | IUPAC_NAME | LC-MS (MH$^+$) | NMR description (CDCl$_3$ otherwise specified) | αD (589 nm) |
|---|---|---|---|---|---|
| 1 | 1.oxalic acid | (+)-2-(1-{2-[2-(2-oxopiperidin-1-yl)phenyl]ethyl}pyrrolidin-3-yl)benzamide oxalate | 392 | 7.57 (dd, J = 7.8, 3.8 Hz, 1 H), 7.45 (m, 1 H), 7.39 (m, 2 H), 7.31 (m, 3 H), 7.23 (m, 1 H), 3.91 (m, 1 H), 3.69 (m, 1 H), 3.59 (m, 1 H), 3.47 (m, 2 H), 3.39 (m, 1 H), 3.33 (d, J = 6.3 Hz, 2 H), 3.26 (m, 1 H), 2.83 (m, 2 H), 2.45 (m, 1 H), 2.38 (s, 1 H), 2.33 (d, J = 5.8 Hz, 1 H), 2.10 (m, 1 H), 1.91 (s, 2 H), 1.85 (d, J = 0.8 Hz, 2 H) | +0.005 (0.51%) |
| 2 | 1.oxalic acid | N-methyl-2-(1-{2-[2-(2-oxopiperidin-1-yl)phenyl]ethyl}pyrrolidin-3-yl)benzamide oxalate | 406 | 8.34 (q, J = 3.8 Hz, 1 H), 7.58 (dd, J = 7.8, 4.5 Hz, 1 H), 7.45 (m, 1 H), 7.32 (m, 6 H), 3.81 (m, 5 H), 3.58 (m, 1 H), 3.35 (m, 1 H), 2.84 (m, 2 H), 2.76 (d, J = 4.5 Hz, 3 H), 2.42 (m, 2 H), 2.30 (d, J = 1.8 Hz, 2 H), 2.11 (m, 1 H), 1.88 (m, 4 H) | |
| 3 | 1.oxalic acid | 2-(1-{2-[2-(2-oxopiperidin-1-yl)phenyl]ethyl}pyrrolidin-3-yl)benzonitrile oxalate | 374 | 7.84 (d, J = 7.8 Hz, 1 H), 7.76 (m, 2 H), 7.47 (s, 1 H), 7.40 (m, 1 H), 7.32 (m, 2 H), 7.22 (m, 1 H), 3.88 (m, 2 H), 3.69 (d, J = 9.3 Hz, 1 H), 3.58 (m, 1 H), 3.43 (d, J = 1.5 Hz, 2 H), 3.36 (m, 1 H), 3.33 (s, 1 H), 3.25 (m, 2 H), 2.81 (m, 2 H), 2.47 (s, 1 H), 2.35 (d, J = 16.6 Hz, 2 H), 2.06 (m, 1 H), 1.87 (m, 4 H) | |
| 4 | 1.oxalic acid | 2-(1-{2-[2-(2-oxopiperidin-1-yl)phenyl]ethyl}piperidin-3-yl)benzamide oxalate | 406 | — | |
| 5 | 1.oxalic acid | 1-[2-(2-{3-[2-(trifluoromethyl)phenyl]pyrrolidin-1-yl}ethyl)phenyl]piperidin-2-one oxalate | 417 | 7.87 (t, J = 7.0 Hz, 1 H), 7.73 (m, 2 H), 7.49 (m, 1 H), 7.40 (m, 1 H), 7.32 (m, 2 H), 7.22 (m, 1 H), 3.83 (m, 1 H), 3.40 (m, 8 H), 2.82 (m, 2 H), 2.46 (s, 1 H), 2.39 (m, 1 H), 2.30 (m, 1 H), 2.08 (m, 1 H), 1.89 (s, 4 H) | |
| 6 | 1.oxalic acid | 1-(2-{2-[3-(2-methoxyphenyl)pyrrolidin-1-yl]ethyl}phenyl)piperidin-2-one oxalate | 379 | 7.32 (m, 6 H), 7.03 (d, J = 8.0 Hz, 1 H), 6.96 (t, J = 7.5 Hz, 1 H), 3.81 (s, 3 H), 3.52 (m, 9 H), 2.82 (m, 2 H), 2.44 (m, 1 H), 2.32 (m, 2 H), 2.08 (m, 1 H), 1.89 (s, 4 H) | |
| 7 | 1.oxalic acid | 1-(2-{2-[3-(3-methoxyphenyl)pyrrolidin-1-yl]ethyl}phenyl)piperidin-2-one oxalate | 379 | 7.40 (m, 1 H), 7.27 (m, 4 H), 6.93 (m, 2 H), 6.84 (dd, J = 7.8, 1.5 Hz, 1 H), 3.76 (s, 3 H), 3.40 (m, 9 H), 2.83 (m, 2 H), 2.37 (m, 3 H), 2.04 (m, 1 H), 1.86 (m, 4 H) | |
| 8 | 1.oxalic acid | 1-(2-{2-[3-(4-methoxyphenyl)pyrrolidin-1-yl]ethyl}phenyl)piperidin-2-one oxalate | 379 | 7.40 (m, 1 H), 7.28 (m, 5 H), 6.92 (d, J = 8.5 Hz, 2 H), 3.72 (m, 4 H), 3.58 (m, 1 H), 3.47 (m, 3 H), 3.30 (m, 3 H), 3.15 (m, 1 H), 2.84 (m, 2 H), 2.46 (m, 1 H), 2.34 (m, 2 H), 2.00 (m, 1 H), 1.88 (m, 4 H) | |
| 9 | 1.oxalic acid | 1-(2-{2-[3-(2-fluorophenyl)pyrrolidin-1-yl]ethyl}phenyl)piperidin-2-one oxalate | 367 | 7.50 (m, 1 H), 7.41 (m, 1 H), 7.32 (m, 3 H), 7.21 (m, 3 H), 3.77 (m, 1 H), 3.69 (m, 1 H), 3.58 (m, 1 H), 3.40 (m, 3 H), 3.25 (m, 3 H), 2.82 (m, 2 H), 2.46 (s, 1 H), 2.35 (m, 2 H), 2.07 (m, 1 H), 1.90 (m, 4 H) | |
| 10 | 1.oxalic acid | 1-(2-{2-[3-(2-chlorophenyl)pyrrolidin-1-yl]ethyl}phenyl)piperidin-2-one oxalate | 383/385 | 7.58 (m, 1 H), 7.47 (s, 1 H), 7.39 (m, 2 H), 7.31 (m, 3 H), 7.22 (m, 1 H), 3.92 (m, 1 H), 3.62 (m, 2 H), 3.39 (m, 3 H), 3.23 (m, 3 H), 2.82 (m, 2 H), 2.45 (m, 1 H), 2.34 (m, 2 H), 2.05 (m, 1 H), 1.88 (d, J = 4.5 Hz, 4 H) | |
| 11 | | 1-[2-(2-{3-[2-(3-methyl-1,2,4-oxadiazol-5-yl)phenyl]pyrrolidin-1-yl}ethyl)phenyl]piperidin-2-one | 431 | — | |
| 12 | 1.oxalic acid | (+)-2-(1-{2-[2-(2-oxopiperidin-1-yl)phenyl]ethyl}pyrrolidin-3-yl)benzonitrile oxalate | 374 | 7.84 (d, J = 7.5 Hz, 1 H), 7.75 (m, 2 H), 7.47 (s, 1 H), 7.40 (m, 1 H), 7.31 (m, 2 H), 7.22 (m, 1 H), 3.90 (m, 1 H), 3.70 (m, 1 H), 3.59 (m, 1 H), 3.45 (m, 2 H), 3.34 (d, J = 11.8 Hz, 1 H), 3.25 (m, 2 H), 2.82 (m, 2 H), 2.47 (s, 1 H), 2.34 (d, J = 16.8 Hz, 2 H), 2.06 (m, 1 H), 1.84 (m, 4 H) | +0.042 (0.52%) |
| 13 | 1.oxalic acid | (−)-2-(1-{2-[2-(2-oxopiperidin-1-yl)phenyl]ethyl}pyrrolidin-3-yl)benzonitrile oxalate | 374 | 7.84 (d, J = 7.5 Hz, 1 H), 7.75 (m, 2 H), 7.47 (s, 1 H), 7.40 (m, 1 H), 7.31 (m, 2 H), 7.22 (m, 1 H), 3.90 (m, 1 H), 3.70 (m, 1 H), 3.59 (m, 1 H), 3.45 (m, 2 H), 3.34 (d, J = 11.8 Hz, 1 H), 3.25 (m, 2 H), 2.82 (m, 2 H), 2.47 (s, 1 H), 2.34 (d, J = 16.8 Hz, 2 H), 2.06 (m, 1 H), 1.84 (m, 4 H) | −0.073 (0.92%) |

TABLE I-continued

Physical Characterization of Example Compounds.

| n° | ADDUCT | IUPAC_NAME | LC-MS (MH+) | NMR description (CDCl3 otherwise specified) | αD (589 nm) |
|---|---|---|---|---|---|
| 14 | | 1-{2-[2-(3-phenylpyrrolidin-1-yl)ethyl]phenyl}piperidin-2-one | 349 | 7.26 (m, 9 H), 3.58 (m, 1 H), 3.45 (m, 1 H), 3.31 (m, 1 H), 2.96 (td, J = 8.5, 2.8 Hz, 1 H), 2.70 (m, 2 H), 2.63 (m, 2 H), 2.56 (m, 2 H), 2.45 (s, 1 H), 2.36 (m, 2 H), 2.23 (m, 1 H), 1.86 (m, 4 H), 1.74 (m, 1 H) | |
| 15 | 1.oxalic acid | 3-(1-{2-[2-(2-oxopiperidin-1-yl)phenyl]ethyl}pyrrolidin-3-yl)benzonitrile oxalate | 374 | 7.95 (m, 1 H), 7.75 (m, 2 H), 7.60 (t, J = 7.8 Hz, 1 H), 7.44 (m, 1 H), 7.35 (d, J = 3.5 Hz, 2 H), 7.26 (m, 1 H), 3.63 (m, 9 H), 2.86 (m, 2 H), 2.41 (m, 3 H), 2.19 (m, 1 H), 1.92 (s, 4 H) | |
| 16 | 1.oxalic acid | 4-(1-{2-[2-(2-oxopiperidin-1-yl)phenyl]ethyl}pyrrolidin-3-yl)benzonitrile oxalate | 374 | 7.86 (d, J = 8.0 Hz, 2 H), 7.62 (m, 2 H), 7.44 (d, J = 3.8 Hz, 1 H), 7.35 (d, J = 3.3 Hz, 2 H), 7.27 (m, 1 H), 3.63 (m, 9 H), 2.88 (m, 2 H), 2.44 (m, 3 H), 2.18 (m, 1 H), 1.93 (s, 4 H) | |
| 17 | | (−)-1-[2-(2-{3-[2-(pyrrolidin-1-ylcarbonyl)phenyl]pyrrolidin-1-yl}ethyl)phenyl]piperidin-2-one | 446 | 7.48 (dd, J = 7.8, 4.3 Hz, 1 H), 7.37 (m, 2 H), 7.24 (m, 3 H), 7.14 (m, 2 H), 3.58 (m, 1 H), 3.47 (t, J = 6.8 Hz, 2 H), 3.32 (s, 14 H), 3.25 (d, J = 8.0 Hz, 1 H), 3.02 (t, J = 6.5 Hz, 2 H), 2.84 (t, J = 7.5 Hz, 1 H), 2.68 (m, 6 H), 2.55 (m, 1 H), 2.36 (t, J = 5.3 Hz, 2 H), 2.17 (m, 1 H), 1.88 (m, 6 H), 1.75 (m, 3 H) | −0.037 (0.45%) |
| 18 | 1.oxalic acid | 1-(2-{2-[3-(2-methoxyphenyl)piperidin-1-yl]ethyl}phenyl)piperidin-2-one oxalate | 393 | 7.27 (m, 6 H), 6.99 (m, 2 H), 3.80 (s, 3 H), 3.57 (m, 1 H), 3.40 (m, 4 H), 3.12 (m, 2 H), 2.89 (m, 4 H), 2.36 (m, 2 H), 1.85 (m, 7 H), 1.69 (s, 1 H) | |
| 19 | 1.oxalic acid | (+)-1-(2-{2-[3-(2-methoxyphenyl)pyrrolidin-1-yl]ethyl}phenyl)piperidin-2-one oxalate | 379 | 7.32 (m, 6 H), 7.03 (d, J = 8.0 Hz, 1 H), 6.96 (t, J = 7.5 Hz, 1 H), 3.81 (s, 3 H), 3.52 (m, 9 H), 2.82 (m, 2 H), 2.44 (m, 1 H), 2.32 (m, 2 H), 2.08 (m, 1 H), 1.89 (s, 4 H) | +0.013 (0.52%) |
| 20 | 1.oxalic acid | (−)-1-(2-{2-[3-(2-methoxyphenyl)pyrrolidin-1-yl]ethyl}phenyl)piperidin-2-one oxalate | 379 | 7.32 (m, 6 H), 7.03 (d, J = 8.0 Hz, 1 H), 6.96 (t, J = 7.5 Hz, 1 H), 3.81 (s, 3 H), 3.52 (m, 9 H), 2.82 (m, 2 H), 2.44 (m, 1 H), 2.32 (m, 2 H), 2.08 (m, 1 H), 1.89 (s, 4 H) | −0.015 (0.63%) |
| 21 | 1.oxalic acid | 1-[2-(2-{3-[3-(trifluoromethyl)phenyl]pyrrolidin-1-yl}ethyl)phenyl]piperidin-2-one | 417 | — | |
| 22 | 1.oxalic acid | 1-(2-{2-[3-(3-fluorophenyl)pyrrolidin-1-yl]ethyl}phenyl)piperidin-2-one oxalate | 367 | — | |
| 23 | 1.oxalic acid | 1-{2-[2-(3-phenylazetidin-1-yl)ethyl]phenyl}piperidin-2-one oxalate | 335 | 7.41 (m, 5 H), 7.31 (m, 3 H), 7.22 (m, 1 H), 4.34 (d, J = 16.1 Hz, 2 H), 4.07 (m, 3 H), 3.57 (m, 1 H), 3.29 (m, 3 H), 2.65 (m, 2 H), 2.37 (m, 2 H), 1.88 (m, 4 H) | |
| 24 | 1.oxalic acid | 1-(2-{2-[3-(3-fluorophenyl)piperidin-1-yl]ethyl}phenyl)piperidin-2-one oxalate | 381 | 7.39 (m, 2 H), 7.30 (m, 2 H), 7.16 (m, 4 H), 3.57 (m, 1 H), 3.39 (m, 4 H), 3.09 (m, 3 H), 2.84 (m, 3 H), 2.36 (m, 2 H), 1.87 (m, 7 H), 1.67 (m, 1 H), 1.06 (t, J = 7.0 Hz, 1 H) | |
| 25 | 1.oxalic acid | 1-(2-{2-[3-(3-methoxyphenyl)piperidin-1-yl]ethyl}phenyl)piperidin-2-one oxalate | 393 | 7.34 (m, 1 H), 7.25 (m, 3 H), 7.18 (m, 1 H), 6.83 (m, 3 H), 3.75 (s, 3 H), 3.56 (m, 1 H), 3.35 (m, 2 H), 3.21 (m, 2 H), 2.89 (m, 3 H), 2.74 (m, 2 H), 2.34 (m, 2 H), 1.84 (m, 6 H), 1.63 (m, 2 H) | |
| 26 | 1.oxalic acid | 1-{2-[2-(3-phenylpiperidin-1-yl)ethyl]phenyl}piperidin-2-one oxalate | 363 | 7.35 (t, J = 7.7 Hz, 3 H), 7.27 (m, 5 H), 7.19 (m, 1 H), 3.56 (m, 1 H), 3.31 (m, 3 H), 2.98 (m, 3 H), 2.74 (m, 4 H), 2.34 (m, 2 H), 1.84 (m, 7 H), 1.62 (m, 1 H) | |
| 27 | 1.oxalic acid | 1-(2-{2-[3-(4-chlorophenyl)pyrrolidin-1-yl]ethyl}phenyl)piperidin-2-one oxalate | 383/385 | (DMSO) 7.41 (s, 1 H), 7.33 (m, 4 H), 7.24 (m, 2 H), 7.13 (m, 1 H), 3.48 (m, 4 H), 3.22 (m, 7 H), 2.73 (m, 2 H), 2.25 (m, 2 H), 1.94 (m, 1 H), 1.75 (m, 4 H). | |
| 28 | 1.oxalic acid | 1-(2-{2-[3-(3-chlorophenyl)pyrrolidin-1-yl]ethyl}phenyl)piperidin-2-one oxalate | 383/385 | (DMSO) 7.47 (d, 1 H, J = 1.9 Hz), 7.39 (m, 2 H), 7.31 (m, 4 H), 7.22 (m, 1 H), 3.56 (m, 4 H), 3.30 (m, 8 H), 2.83 (m, 2 H), 2.36 (m, 3 H), 1.86 (m, 4 H) | |
| 29 | 1.oxalic acid | 1-(2-{2-[3-(benzyloxy)pyrrolidin-1-yl]ethyl}phenyl)piperidin-2-one oxalate | 379 | 7.20 (m, 9 H), 4.43 (s, 2 H), 4.22 (s, 1 H), 3.49 (m, 1 H), 3.33 (s, 2 H), 3.25 (d, J = 5.3 Hz, 2 H), 3.20 (m, 1 H), 3.11 (m, 2 H), 2.72 (m, 2 H), 2.36 (s, 1 H), 2.25 (m, 1 H), 2.09 (m, 1 H), 2.00 (m, 1 H), 1.79 (m, 4 H) | |
| 30 | 1.oxalic acid | 1-(2-{2-[3-(4-fluorophenyl)azetidin-1-yl]ethyl}phenyl)piperidin-2-one oxalate | 353 | 7.49 (m, 2 H), 7.43 (m, 1 H), 7.32 (m, 2 H), 7.23 (m, 3 H), 4.30 (m, 2 H), 4.02 (m, 3 H), 3.58 (m, 1 H), 3.29 (m, 3 H), 2.64 (m, 2 H), 2.46 (m, 1 H), 2.35 (m, 1 H), 1.85 (m, 4 H) | |
| 31 | 1.oxalic acid | 3-(1-{2-[2-(2-oxopiperidin-1-yl)phenyl]ethyl}azetidin-3-yl)benzonitrile oxalate | 360 | 7.97 (s, 1 H), 7.77 (s, 2 H), 7.59 (s, 1 H), 7.42 (s, 1 H), 7.32 (s, 2 H), 7.22 (s, 1 H), 4.33-4.30 (d, 2 H), 4.10 (s, 3 H), 2.64-2.33 (m overlap with solvent peak), 1.88 (s, 4 H) | |
| 32 | 1.oxalic acid | 1-(2-{2-[3-(2-fluorophenyl)azetidin-1-yl]ethyl}phenyl)piperidin-2-one oxalate | 353 | 7.52-7.19 (m, 8 H), 4.40-4.06 (m, 6 H), 3.34-3.25 (m, 4 H), 2.72-2.60 (m, 2 H), 2.38-2.31 (m, 1 H), 1.89 (s, 4 H) | |

TABLE I-continued

Physical Characterization of Example Compounds.

| n° | ADDUCT | IUPAC_NAME | LC-MS (MH+) | NMR description (CDCl₃ otherwise specified) | αD (589 nm) |
|---|---|---|---|---|---|
| 33 | 1.oxalic acid | 1-{2-[2-(3-cyclohexylpyrrolidin-1-yl)ethyl]phenyl}piperidin-2-one oxalate | 355 | 7.43 (internal standard), 7.37-7.34 (m, 1H), 7.31-7.25 (m, 2H), 7.19-7.15 (m, 1H), 6.88-6.71 (internal standard), 3.67-3.51 (m, 3H), 3.37-3.17 (m, 4H), 3.15-2.6 (m, 4H), 2.45-2.32 (m, 2H), 2.14-1.80 (m, 6H), 1.73-1.49 (m, 6H), 1.25-1.02 (m, 4H), 0.95-0.81 (m, 2H), 0.16 (internal standard) | |
| 34 | 1.oxalic acid | 1-(2-{2-[3-(2-hydroxyphenyl)pyrrolidin-1-yl]ethyl}phenyl)piperidin-2-one oxalate | 365 | 7.17 (m, 1 H), 7.08 (m, 2 H), 6.98 (m, 2 H), 6.86 (m, 1 H), 6.62 (m, 1 H), 6.56 (m, 1 H), 3.48 (m, 2 H), 3.35 (m, 1 H), 3.23 (m, 2 H), 3.06 (m, 4 H), 2.60 (m, 2 H), 2.22 (m, 1 H), 2.09 (m, 2 H), 1.88 (m, 1 H), 1.64 (m, 4 H) | |
| 35 | 2.oxalic acid | 1-(2-{2-[3-(pyridin-2-yl)pyrrolidin-1-yl]ethyl}phenyl)piperidin-2-one dioxalate | 350 | 8.56 (d, J = 4.5 Hz, 1 H), 7.80 (td, J = 7.5, 1.5 Hz, 1 H), 7.41 (d, J = 7.3 Hz, 2 H), 7.33 (m, 3 H), 7.23 (m, 1 H), 3.56 (m, 9 H), 2.85 (m, 2 H), 2.44 (m, 2 H), 2.34 (m, 1 H), 2.13 (m, 1 H), 1.86 (m, 4 H) | |
| 36 | | 1-(2-{2-[3-(pyridin-2-yl)pyrrolidin-1-yl]ethyl}phenyl)piperidin-2-one | 350 | 8.56 (d, J = 4.5 Hz, 1 H), 7.80 (td, J = 7.5, 1.5 Hz, 1 H), 7.41 (d, J = 7.3 Hz, 2 H), 7.33 (m, 3 H), 7.23 (m, 1 H), 3.56 (m, 9 H), 2.85 (m, 2 H), 2.44 (m, 2 H), 2.34 (m, 1 H), 2.13 (m, 1 H), 1.86 (m, 4 H) | |
| 37 | 1.oxalic acid | 1-(2-{2-[3-(4-fluorophenyl)pyrrolidin-1-yl]ethyl}phenyl)piperidin-2-one oxalate | 367 | 7.18 (m, 3 H), 7.08 (m, 2 H), 6.96 (m, 3 H), 3.23 (m, 9 H), 2.59 (m, 2 H), 2.17 (m, 2 H), 2.08 (m, 1 H), 1.79 (m, 1 H), 1.62 (m, 4 H) | |
| 38 | 1.oxalic acid | 1-(2-{2-[(3R)-3-(2,2,2-trifluoroethyl)pyrrolidin-1-yl]ethyl}phenyl)piperidin-2-one oxalate | 355 | 7.38 (m, 1 H), 7.30 (m, 2 H), 7.21 (m, 1 H), 3.58 (m, 1 H), 3.47 (m, 1 H), 3.31 (m, 3 H), 3.17 (m, 2 H), 2.97 (m, 1 H), 2.79 (m, 2 H), 2.56 (m, 4 H), 2.32 (m, 1 H), 2.17 (m, 1 H), 1.88 (d, J = 5.0 Hz, 4 H), 1.73 (dd, J = 12.0, 8.3 Hz, 1 H) | |
| 39 | 1.trifluoro-acetate | 1-(2-{2-[(3S)-3-(2,2,2-trifluoroethyl)pyrrolidin-1-yl]ethyl}phenyl)piperidin-2-one trifluoroacetate | 355 | 7.38 (m, 1 H), 7.30 (m, 2 H), 7.21 (m, 1 H), 3.58 (m, 1 H), 3.47 (m, 1 H), 3.31 (m, 3 H), 3.17 (m, 2 H), 2.97 (m, 1 H), 2.79 (m, 2 H), 2.56 (m, 4 H), 2.32 (m, 1 H), 2.17 (m, 1 H), 1.88 (d, J = 5.0 Hz, 4 H), 1.73 (dd, J = 12.0, 8.3 Hz, 1 H) | |
| 40 | 1.oxalic acid | 1-(2-{2-[(3S)-3-(2,2,2-trifluoroethyl)pyrrolidin-1-yl]ethyl}phenyl)piperidin-2-one oxalate | 355 | 7.36 (m, 1 H), 7.29 (m, 2 H), 7.19 (m, 1 H), 3.57 (m, 1 H), 3.33 (m, 2 H), 3.09 (m, 4 H), 2.75 (m, 3 H), 2.45 (m, 2 H), 2.35 (m, 1 H), 2.14 (m, 1 H), 1.89 (m, 4 H), 1.69 (m, 1 H) | |
| 41 | 1.oxalic acid | 4-(1-{2-[2-(2-oxopiperidin-1-yl)phenyl]ethyl}piperidin-3-yl)benzonitrile oxalate | 388 | 7.85 (d, J = 8.1 Hz, 2 H), 7.53 (d, J = 8.1 Hz, 2 H), 7.28 (m, 4 H), 3.57 (m, 1 H), 3.44 (m, 3 H), 3.32 (m, 1 H), 3.07 (m, 4 H), 2.83 (m, 3 H), 2.36 (m, 2 H), 1.89 (m, 7 H), 1.70 (m, 1 H) | |
| 42 | 1.oxalic acid | (−)-4-(1-{2-[2-(2-oxopiperidin-1-yl)phenyl]ethyl}pyrrolidin-3-yl)benzonitrile oxalate | 374 | 7.60 (d, J = 8.0 Hz, 2 H), 7.36 (d, J = 8.2 Hz, 2 H), 7.17 (m, 1 H), 7.08 (m, 2 H), 6.99 (m, 1 H), 3.29 (m, 9 H), 2.60 (m, 2 H), 2.16 (m, 3 H), 1.83 (m, 1 H), 1.63 (m, 4 H) | −0.076 (0.53%) |
| 43 | 1.15.oxalic acid | (+)-4-(1-{2-[2-(2-oxopiperidin-1-yl)phenyl]ethyl}pyrrolidin-3-yl)benzonitrile oxalate | 374 | 7.60 (m, 2 H), 7.36 (m, 2 H), 7.16 (m, 1 H), 7.08 (m, 2 H), 6.98 (m, 1 H), 3.51 (m, 1 H), 3.43 (m, 1 H), 3.35 (m, 1 H), 3.23 (m, 2 H), 3.15 (d, J = 7.0 Hz, 1 H), 3.03 (m, 3 H), 2.59 (m, 2 H), 2.32 (dd, J = 0.9, 0.4 Hz, 1 H), 2.20 (m, 1 H), 2.12 (m, 1 H), 1.82 (m, 1 H), 1.65 (m, 4 H) | +0.081 (0.5%) |
| 44 | 1.oxalic acid | 1-(2-{2-[3-(2-methoxyphenyl)azetidin-1-yl]ethyl}phenyl)piperidin-2-one oxalate | 365 | 7.41-7.20 (m, 6 H), 7.02-6.96 (m, 2 H), 4.34-4.30 (m, 2 H), 4.16-4.01 (m, 2 H), 3.79 (s, 2 H), 2.66-2.61 (m, 1 H), 2.37-2.33 (m, 1 H), 1.88 (s, 4 H) | |
| 45 | 1.oxalic acid | 1-(2-{2-[3-(3-fluorophenyl)azetidin-1-yl]ethyl}phenyl)piperidin-2-one oxalate | 353 | 7.26-6.93 (m, 8 H), 4.15-4.07 (m, 2 H), 3.92-3.81 (m, 3 H), 2.52-2.39 (m, 2 H), 2.20-2.14 (m, 1 H), 1.70 (s, 4 H) | |
| 46 | 1.oxalic acid | 1-(2-{2-[3-(3,4-difluorophenyl)pyrrolidin-1-yl]ethyl}phenyl)piperidin-2-one oxalate | 385 | 7.53 (m, 1 H), 7.41 (m, 2 H), 7.32 (m, 2 H), 7.23 (m, 2 H), 3.71 (m, 1 H), 3.57 (m, 2 H), 3.42 (m, 2 H), 3.33 (m, 1 H), 3.21 (m, 2 H), 2.81 (m, 2 H), 2.40 (m, 2 H), 2.30 (m, 1 H), 2.03 (m, 1 H), 1.87 (m, 4 H) | |
| 47 | 1.oxalic acid | 1-(2-{2-[3-(3-methoxyphenyl)azetidin-1-yl]ethyl}phenyl)piperidin-2-one oxalate | 365 | 7.41 (s, 1 H), 7.35 (d, J = 3.0 Hz, 1 H), 7.22 (m, 2 H), 7.14 (m, 1 H), 6.90 (m, 2 H), 6.79 (d, J = 8.0 Hz, 1 H), 4.24 (m, 2 H), 3.98 (m, 3 H), 3.70 (s, 3 H), 3.49 (m, 1 H), 3.23 (m, 3 H), 2.56 (m, 2 H), 2.42 (s, 1 H), 2.26 (d, J = 16.8 Hz, 1 H), 1.79 (m, 4 H) | |
| 48 | 1.oxalic acid | 1-{2-[2-(3-benzylpyrrolidin-1-yl)ethyl]phenyl}piperidin-2-one oxalate | 363 | 7.37 (m, 1 H), 7.30 (m, 4 H), 7.21 (m, 4 H), 3.57 (m, 1 H), 3.31 (m, 4 H), 3.17 (m, 2 H), 2.93 (m, 1 H), 2.75 (m, 4 H), 2.60 (m, 1 H), 2.37 (m, 2 H), 2.02 (m, 1 H), 1.85 (m, 4 H), 1.68 (m, 1 H) | |
| 49 | 1.oxalic acid | 1-(2-{2-[3-(2-methoxyphenoxy)pyrrolidin-1-yl]ethyl}phenyl)piperidin-2-one oxalate | 395 | (DMSO) 7.38 (m, 1 H), 7.31 (m, 2 H), 7.21 (m, 1 H), 6.99 (m, 3 H), 6.90 (m, 1 H), 5.03 (s, 1 H), 3.78 (m, 3 H), 3.58 (m, 2 H), 3.35 (m, 4 H), 3.18 (m, 2 H), 2.80 (m, 2 H), 2.33 (m, 2 H), 2.09 (m, 1 H), 1.84 (m, 4 H). | |
| 50 | | 4-[(1-{2-[2-(2-oxopiperidin-1-yl)phenyl]ethyl}pyrrolidin-3-yl)oxy]benzonitrile | 390 | 7.36 (d, J = 8.2 Hz, 2 H), 7.08 (m, 4 H), 6.92 (m, 1 H), 6.69 (d, J = 8.6 Hz, 2 H), 4.66 (m, 1 H), 3.38 (m, 1 H), 3.22 (m, 1 H), 2.73 (m, 3 H), 2.52 (m, 4 H), 2.38 (m, 3 H), 2.16 (m, 1 H), 1.79 (m, 5 H) | |

TABLE I-continued

Physical Characterization of Example Compounds.

| n° | ADDUCT | IUPAC_NAME | LC-MS (MH+) | NMR description (CDCl3 otherwise specified) | αD (589 nm) |
|---|---|---|---|---|---|
| 51 | 1.oxalic acid | 1-(2-{2-[3-(tetrahydro-2H-pyran-4-yl)pyrrolidin-1-yl]ethyl}phenyl)piperidin-2-one oxalate | 357 | 7.38 (m, 1 H), 7.31 (m, 2 H), 7.21 (m, 1 H), 3.84 (m, 2 H), 3.57 (m, 1 H), 3.25 (m, 9 H), 2.79 (m, 2 H), 2.46 (m, 1 H), 2.33 (m, 1 H), 2.05 (m, 2 H), 1.88 (m, 4 H), 1.56 (m, 4 H), 1.20 (m, 2 H) | |
| 52 | | 1-{2-[2-(3-benzylazetidin-1-yl)ethyl]phenyl}piperidin-2-one | 349 | 7.28 (m, 6 H), 7.19 (m, 1 H), 7.10 (m, 3 H), 3.58 (m, 1 H), 3.42 (m, 3 H), 2.90 (m, 4 H), 2.78 (m, 1 H), 2.67 (m, 1 H), 2.51 (m, 4 H), 1.96 (m, 4 H) | |
| 53 | | 1-(2-{2-[3-(pyridin-3-yl)pyrrolidin-1-yl]ethyl}phenyl)piperidin-2-one | 350 | 8.51 (s, 1 H), 8.44 (d, J = 4.7 Hz, 1 H), 7.62 (d, J = 8.0 Hz, 1 H), 7.35 (m, 1 H), 7.27 (m, 2 H), 7.22 (dd, J = 7.6, 4.9 Hz, 1 H), 7.13 (m, 1 H), 3.60 (m, 1 H), 3.40 (m, 2 H), 3.09 (m, 1 H), 2.78 (m, 6 H), 2.61 (m, 3 H), 2.36 (m, 2 H), 1.91 (m, 5 H) | |
| 54 | 1.trifluoro acetic acid | 1-(2-{2-[3-(4,4-difluorocyclohexyl)pyrrolidin-1-yl]ethyl}phenyl)piperidin-2-one trifluoroacetate | 391 | — | |
| 55 | 1.oxalic acid | 4-[(1-{2-[2-(2-oxopiperidin-1-yl)phenyl]ethyl}azetidin-3-yl)oxy]benzonitrile oxalate | 376 | 7.69-7.67 (d, 2 H), 7.25-7.07 (m, 4 H), 6.93-6.91 (d, 2 H), 5.01 (s, 1 H), 4.34-4.25 (m, 2 H), 3.82-3.08 (m, overlap with solvent peak), 2.55-2.18 (m, overlap with solvent peak), 1.74 (s, 4 H) | |
| 56 | 1.trifluoro acetic acid | 1-(2-{2-[3-(2-methylpropyl)pyrrolidin-1-yl]ethyl}phenyl)piperidin-2-one trifluoroacetate | 329 | 7.54 (m, 3 H), 7.35 (m, 1 H), 4.05 (m, 2 H), 3.82 (m, 1 H), 3.61 (m, 2 H), 3.48 (m, 1 H), 3.15 (m, 4 H), 2.84 (m, 2 H), 2.66 (m, 2 H), 2.42 (m, 1 H), 2.19 (m, 4 H), 1.90 (m, 1 H), 1.75 (m, 1 H), 1.54 (m, 2 H), 1.10 (m, 6 H) | |
| 57 | 1.trifluoro acetic acid | 1-{2-[2-(3-propylpyrrolidin-1-yl)ethyl]phenyl}piperidin-2-one trifluoroacetate | 315 | 11.12 (m, 1 H), 9.33 (s, 2 H), 7.33 (m, 3 H), 7.14 (m, 1 H), 3.85 (m, 2 H), 3.62 (m, 1 H), 3.36 (m, 3 H), 2.96 (m, 3 H), 2.64 (m, 2 H), 2.42 (m, 2 H), 2.23 (m, 1 H), 2.00 (m, 4 H), 1.70 (m, 1 H), 1.36 (m, 4 H), 0.91 (m, 3 H) | |
| 58 | | 3-[(1-{2-[2-(2-oxopiperidin-1-yl)phenyl]ethyl}azetidin-3-yl)oxy]benzonitrile | 376 | 7.40 (m, 1 H), 7.28 (m, 4 H), 7.14 (m, 1 H), 7.00 (m, 2 H), 4.75 (m, 1 H), 3.83 (m, 1 H), 3.61 (m, 1 H), 3.42 (m, 1 H), 3.15 (m, 2 H), 2.79 (m, 2 H), 2.57 (m, 4 H), 1.98 (m, 4 H) | |
| 59 | | 2-[(1-{2-[2-(2-oxopiperidin-1-yl)phenyl]ethyl}azetidin-3-yl)oxy]benzonitrile | 376 | 7.59 (m, 1 H), 7.50 (m, 1 H), 7.33 (m, 1 H), 7.28 (m, 3 H), 7.12 (m, 1 H), 7.02 (m, 1 H), 6.70 (d, 1 H), 4.87 (m, 1 H), 3.91 (m, 1 H), 3.62 (m, 1 H), 3.45 (m, 1 H), 3.24 (m, 2 H), 2.88 (m, 1 H), 2.74 (m, 1 H), 2.59 (m, 4 H), 1.97 (m, 3 H) | |
| 60 | | 1-(2-{2-[3-(4-fluorophenoxy)azetidin-1-yl]ethyl}phenyl)piperidin-2-one | 369 | — | |
| 61 | | 1-(2-{2-[3-(3-methoxyphenoxy)azetidin-1-yl]ethyl}phenyl)piperidin-2-one | 381 | — | |
| 62 | | 1-(2-{2-[3-(2-bromobenzyl)azetidin-1-yl]ethyl}phenyl)piperidin-2-one | 427/429 | 7.53 (m, 1 H), 7.29 (m, 2 H), 7.23 (m, 2 H), 7.10 (m, 3 H), 3.57 (m, 1 H), 3.42 (m, 3 H), 3.00 (m, 2 H), 2.88 (m, 3 H), 2.69 (m, 1 H), 2.53 (m, 5 H), 1.96 (m, 4 H) | |
| 63 | | 4-(1-{2-[2-(2-oxopiperidin-1-yl)pyridin-3-yl]ethyl}pyrrolidin-3-yl)benzonitrile | 375 | 8.35 (m, 1 H), 7.81 (m, 1 H), 7.71 (m, 2 H), 7.44 (m, 2 H), 7.31 (m, 1 H), 3.87 (m, 1 H), 3.43 (m, 3 H), 2.88 (m, 1 H), 2.75 (m, 1 H), 2.64 (m, 5 H), 2.32 (m, 3 H), 1.87 (m, 4 H), 1.70 (m, 1 H). | |
| 64 | | 1-(2-{2-[3-(4-methyl-1,3-thiazol-5-yl)pyrrolidin-1-yl]ethyl}phenyl)piperidin-2-one | 370 | 8.33 (s, 1 H), 7.12 (m, 1 H), 7.05 (m, 2 H), 6.91 (dd, J1 = 5.0 Hz, J2 = 3.6 Hz, 1 H), 3.43 (m, 2 H), 3.23 (m, 1 H), 2.89 (d, J = 0.9 Hz, 1 H), 2.59 (m, 6 H), 2.34 (m, 3 H), 2.19 (m, 4 H), 1.78 (m, 5 H), 1.54 (m, 2 H) | |
| 65 | 1.oxalic acid | 1-(2-{2-[3-(5-bromo-2-methoxyphenoxy)azetidin-1-yl]ethyl}phenyl)piperidin-2-one oxalate | 459 | (DMSO) 7.40 (m, 1 H), 7.30 (m, 2 H), 7.18 (m, 2 H), 6.98 (m, 2 H), 4.99 (m, 1 H), 4.36 (m, 4 H), 3.95 (m, 3 H), 3.80 (m, 3 H), 3.59 (m, 2 H), 3.36 (m, 1 H), 3.16 (m, 2 H), 2.65 (m, 2 H), 2.37 (m, 2 H), 1.87 (m, 4 H) | |
| 66 | 1.oxalic acid | 1-{2-[2-(3-phenoxyazetidin-1-yl)ethyl]phenyl}piperidin-2-one oxalate | 351 | (DMSO) 7.40 (m, 1 H), 7.31 (m, 4 H), 7.20 (m, 1 H), 7.01 (t, 1 H, J = 7.3 Hz), 6.86 (d, 2 H, J = 8.0 Hz), 5.00 (m, 1 H), 4.37 (m, 4 H), 3.84 (m, 3 H), 3.58 (m, 1 H), 3.31 (m, 1 H), 3.17 (m, 2 H), 2.62 (m, 2 H), 2.36 (m, 1 H), 1.86 (m, 4 H) | |
| 67 | | 1-{2-[2-(3-tert-butylpyrrolidin-1-yl)ethyl]phenyl}piperidin-2-one | 329 | 7.39-7.33 (m, 1H), 7.33-7.27 (m, 3H, including CDCl3), 7.17-7.13 (m, 1H), 3.66-3.45 (m, 2H), 2.94-2.70 (m, 5H), 2.63-2.56 (m, 3H), 2.49-2.40 (m, 1H), 2.35-2.25 (m, 1H), 2.16-2.07 (m, 1H), 2.04-1.94 (m, 4H), 1.89-1.80 (m, 1H), 1.66-1.55 (m, 1H), 0.9 (s, 9H) | |
| 68 | 1.oxalic acid | 1-{2-[2-(3-(2-methoxyphenoxy)azetidin-1-yl]ethyl}phenyl)piperidin-2-one oxalate | 381 | (DMSO) 7.33 (m, 1 H), 7.23 (m, 2 H), 7.13 (m, 1 H), 6.93 (m, 2 H), 6.80 (m, 1 H), 6.71 (m, 1 H), 4.84 (m, 1 H), 4.32 (m, 4 H), 3.91 (m, 3 H), 3.70 (s, 3 H), 3.49 (m, 1 H), 3.24 (m, 1 H), 3.13 (m, 2 H), 2.55 (m, 2 H), 2.27 (m, 1 H), 1.77 (m, 4 H). | |
| 69 | | 1-(2-{2-[3-(2-chloro-2,2-difluoroethyl)pyrrolidin-1-yl]ethyl}phenyl)piperidin-2-one | 371/373 | — | |

TABLE I-continued

Physical Characterization of Example Compounds.

| n° | ADDUCT | IUPAC_NAME | LC-MS (MH+) | NMR description (CDCl₃ otherwise specified) | αD (589 nm) |
|---|---|---|---|---|---|
| 70 | | 1-(3-{2-[3-(pyridin-2-yl)pyrrolidin-1-yl]ethyl}pyridin-2-yl)piperidin-2-one | 351 | 8.56 (d, J = 4.0 Hz, 1 H), 8.41 (m, 1 H), 7.86 (d, J = 7.5 Hz, 1 H), 7.79 (t, J = 7.5 Hz, 1 H), 7.38 (m, 2 H), 7.31 (m, 1 H), 3.84 (m, 1 H), 3.76 (m, 2 H), 3.40 (m, 6 H), 2.85 (m, 2 H), 2.37 (m, 3 H), 2.12 (m, 1 H), 1.87 (m, 4 H) | |
| 71 | 1.oxalic acid | 1-(3-{2-[3-(pyridin-2-yl)pyrrolidin-1-yl]ethyl}pyridin-2-yl)piperidin-2-one oxalate | 351 | 8.56 (d, J = 4.0 Hz, 1 H), 8.41 (m, 1 H), 7.86 (d, J = 7.5 Hz, 1 H), 7.79 (t, J = 7.5 Hz, 1 H), 7.38 (m, 2 H), 7.31 (m, 1 H), 3.84 (m, 1 H), 3.76 (m, 2 H), 3.40 (m, 6 H), 2.85 (m, 2 H), 2.37 (m, 3 H), 2.12 (m, 1 H), 1.87 (m, 4 H) | |
| 72 | | 1-(2-{2-[3-(1-acetylpiperidin-2-yl)pyrrolidin-1-yl]ethyl}phenyl)piperidin-2-one | 398 | — | |
| 73 | | 1-(2-{2-[3-(pyridin-4-yl)pyrrolidin-1-yl]ethyl}phenyl)piperidin-2-one | 350 | 8.47 (s, 2 H), 7.33 (m, 1 H), 7.25 (dd, J1 = 5.2 Hz, J2 = 3.8 Hz, 2 H), 7.17 (d, J = 3.4 Hz, 2 H), 7.11 (dd, J1 = 5.5 Hz, J2 = 3.7 Hz, 1 H), 3.58 (m, 1 H), 3.41 (m, 1 H), 3.31 (m, 1 H), 3.01 (m, 1 H), 2.58 (m, 3 H), 2.33 (m, 1 H), 1.87 (m, 5 H) | |
| 74 | | 1-(2-{2-[3-(2-fluoropyridin-3-yl)pyrrolidin-1-yl]ethyl}phenyl)piperidin-2-one | 368 | 8.06 (m, 1 H), 7.77 (m, 1 H), 7.36 (m, 1 H), 7.29 (m, 1 H), 7.13 (m, 2 H), 3.61 (m, 2 H), 3.45 (m, 1 H), 3.05 (m, 1 H), 2.80 (m, 7 H), 2.59 (m, 2 H), 2.35 (m, 1 H), 1.92 (m, 6 H), 1 additional proton due to an impurity | |
| 75 | | 1-(2-{2-[3-(tetrahydrofuran-2-yl)pyrrolidin-1-yl]ethyl}phenyl)piperidin-2-one | 343 | 7.29 (m, 1 H), 7.22 (m, 2 H), 7.14 (m, 1 H), 3.58 (m, 4 H), 3.33 (m, 1 H), 3.25 (m, 1 H), 3.12 (m, 4 H), 2.97 (m, 1 H), 2.70 (m, 2 H), 2.37 (d, J = 2.3 Hz, 1 H), 2.29 (m, 2 H), 1.85 (m, 8 H), 1.58 (m, 1 H), 1.38 (m, 1 H) | |
| 76 | 1.oxalic acid | 1-(2-{2-[3-(tetrahydrofuran-2-yl)pyrrolidin-1-yl]ethyl}phenyl)piperidin-2-one oxalate | 343 | 7.29 (m, 1 H), 7.22 (m, 2 H), 7.14 (m, 1 H), 3.58 (m, 4 H), 3.33 (m, 1 H), 3.25 (m, 1 H), 3.12 (m, 4 H), 2.97 (m, 1 H), 2.70 (m, 2 H), 2.37 (d, J = 2.3 Hz, 1 H), 2.29 (m, 2 H), 1.85 (m, 8 H), 1.58 (m, 1 H), 1.38 (m, 1 H) | |
| 77 | 1.trifluoro acetic acid | (+)-1-(2-{2-[3-(tetrahydro-2H-pyran-4-yl)pyrrolidin-1-yl]ethyl}phenyl)piperidin-2-one trifluoroacetate | 357 | 7.29 (m, 1 H), 7.21 (m, 2 H), 7.12 (m, 1 H), 3.76 (m, 2 H), 3.49 (dd, J = 12.0, 6.8 Hz, 1 H), 3.16 (m, 8 H), 2.78 (m, 1 H), 2.69 (m, 2 H), 2.37 (m, 1 H), 2.26 (m, 1 H), 1.95 (m, 2 H), 1.78 (m, 4 H), 1.57 (m, 1 H), 1.47 (m, 2 H), 1.35 (m, 1 H), 1.12 (m, 2 H) | +0.006 (0.6%) |
| 78 | 1.oxalic acid | (+)-1-(2-{2-[3-(tetrahydro-2H-pyran-4-yl)pyrrolidin-1-yl]ethyl}phenyl)piperidin-2-one oxalate | 357 | 7.29 (m, 1 H), 7.21 (m, 2 H), 7.12 (m, 1 H), 3.76 (m, 2 H), 3.49 (dd, J = 12.0, 6.8 Hz, 1 H), 3.16 (m, 8 H), 2.78 (m, 1 H), 2.69 (m, 2 H), 2.37 (m, 1 H), 2.26 (m, 1 H), 1.95 (m, 2 H), 1.78 (m, 4 H), 1.57 (m, 1 H), 1.47 (m, 2 H), 1.35 (m, 1 H), 1.12 (m, 2 H) | +0.003 (0.52%) |
| 79 | 1.oxalic acid | 1-(3-{2-[(3S)-3-(2,2,2-trifluoroethyl)pyrrolidin-1-yl]ethyl}pyridin-2-yl)piperidin-2-one oxalate | 356 | 8.37 (m, 1 H), 7.88 (m, 1 H), 7.30 (m, 1 H), 3.85 (m, 2 H), 3.47 (m, 1 H), 3.37 (m, 1 H), 3.17 (m, 4 H), 2.94 (m, 1 H), 2.79 (m, 2 H), 2.59 (m, 2 H), 2.35 (m, 1 H), 2.18 (m, 1 H), 1.93 (m, 4 H), 1.72 (m, 1 H), missing H obscured by solvant (H2O) | |
| 80 | | 1-(3-{2-[(3S)-3-(2,2,2-trifluoroethyl)pyrrolidin-1-yl]ethyl}pyridin-2-yl)piperidin-2-one | 356 | 8.40 (d, 1H), 7.83 (d, 1H), 7.37 (quad, 1H), 3.66 (m, H2O), 3.47 (m, 3H), 3.38 (m, 3H), 3.25 (m, 5H), 2.93 (m, 1H), 2.80 (m, 2H), 2.52 (dmso), 2.38 (m, 1H), 2.19 (m, 1H), 1.91 (m, 4H), 1.73 (m, 1H) | |
| 81 | 1.trifluoro acetic acid | 1-(2-{2-[3-(tetrahydro-2H-pyran-3-yl)pyrrolidin-1-yl]ethyl}phenyl)piperidin-2-one trifluoroacetate | 357 | — | |
| 82 | | 1-(2-{2-[3-(6-methoxypyridin-2-yl)pyrrolidin-1-yl]ethyl}phenyl)piperidin-2-one | 380 | — | |
| 83 | | 1-(2-{2-[3-(5-fluoropyridin-2-yl)pyrrolidin-1-yl]ethyl}phenyl)piperidin-2-one | 368 | 8.47 (s, 1 H), 7.64 (m, 1 H), 7.37 (m, 2 H), 7.25 (m, 2 H), 7.16 (d, J = 4.0 Hz, 1 H), 3.54 (m, 2 H), 3.02 (s, 1 H), 2.79 (s, 0 H), 2.60 (m, 3 H), 2.36 (m, 4 H), 2.18 (m, 3 H), 1.88 (m, 7 H) | |
| 84 | | 1-(2-{2-[3-(3-fluoropyridin-2-yl)pyrrolidin-1-yl]ethyl}phenyl)piperidin-2-one | 368 | 8.39 (d, J = 4.6 Hz, 1 H), 7.66 (t, J = 9.1 Hz, 1 H), 7.35 (m, 2 H), 7.26 (m, 2 H), 7.16 (m, 1 H), 3.75 (m, 1 H), 3.58 (m, 1 H), 3.13 (m, 2 H), 2.94 (m, 1 H), 2.67 (m, 5 H), 2.35 (m, 4 H), 2.16 (m, 3 H), 1.87 (m, 5 H) | |
| 85 | | 1-(2-{2-[3-(2-fluoro-2-methylpropyl)pyrrolidin-1-yl]ethyl}phenyl)piperidin-2-one | 347 | — | |
| 86 | | 1-[2-(2-{3-[2-oxo-2-(pyrrolidin-1-yl)ethyl]pyrrolidin-1-yl}ethyl)phenyl]piperidin-2-one | 384 | — | |

TABLE I-continued

Physical Characterization of Example Compounds.

| n° | ADDUCT | IUPAC_NAME | LC-MS (MH+) | NMR description (CDCl₃ otherwise specified) | αD (589 nm) |
|---|---|---|---|---|---|
| 87 | 1.oxalic acid | 1-(2-{2-{3-(4-methyl-1,3-thiazol-2-yl)pyrrolidin-1-yl]ethyl}phenyl)piperidin-2-one oxalate | 370 | 8.29 (s, 1 H), 8.18 (m, 1 H), 8.11 (m, 2 H), 8.02 (m, 2 H), 4.76 (m, 1 H), 4.52 (m, 1 H), 4.37 (m, 1 H), 4.18 (m, 4 H), 4.00 (m, 2 H), 3.60 (m, 2 H), 3.23 (m, 1 H), 3.15 (m, 4 H), 2.98 (m, 1 H), 2.88 (s, 1 H) | |
| 88 | | 1-(3-{2-[3-(5-fluoropyridin-2-yl)pyrrolidin-1-yl]ethyl}pyridin-2-yl)piperidin-2-one | 369 | 8.39 (m, 2 H), 7.70 (d, J = 7.6 Hz, 1 H), 7.31 (m, 1 H), 7.20 (m, 2 H), 3.99 (m, 1 H), 3.56 (m, 1 H), 3.38 (m, 1 H), 3.11 (m, 1 H), 2.78 (m, 7 H), 2.55 (m, 2 H), 2.33 (m, 1 H), 2.01 (m, 6 H), 1.77 (m, 2 H) | |
| 89 | 1.oxalic acid | 1-(3-{2-[3-(pyridin-2-yl)pyrrolidin-1-yl]ethyl}pyridin-2-yl)piperidin-2-one oxalate, isomer A | 351 | 8.56 (m, 1 H), 8.40 (m, 1 H), 7.87 (m, 1 H), 7.78 (m, 1 H), 7.40 (m, 2 H), 7.30 (m, 1 H), 2.85 (m, 2 H), 2.42 (m, 2 H), 2.15 (m, 1 H), 1.86 (m, 4 H), missing H obscured by solvent (H2O) | |
| 90 | 1.oxalic acid | (+)-1-(3-{2-[3-(4,4-difluorocyclohexyl)pyrrolidin-1-yl]ethyl}pyridin-2-yl)piperidin-2-one oxalate | 392 | (DMSO) 8.41 (d, 1 H, J = 3.6 Hz), 7.83 (m, 1 H), 7.38 (m, 1 H), 3.84 (m, 1 H), 3.34 (m, 6 H), 2.88 (m, 3 H), 2.34 (m, 1 H), 2.08 (m, 4 H), 1.79 (m, 9 H), 1.39 (m, 1 H), 1.20 (m, 2 H) | +0.010 (0.51%, 365 nm) |
| 91 | 1.oxalic acid | (−)-1-(3-{2-[3-(4,4-difluorocyclohexyl)pyrrolidin-1-yl]ethyl}pyridin-2-yl)piperidin-2-one oxalate, | 392 | (DMSO) 8.40 (dd, 1 H, J = 4.6, 1.4 Hz), 7.83 (dd, 1 H, J = 7.5, 1.1 Hz), 7.37 (dd, 1 H, J = 7.6, 4.8 Hz), 3.84 (d, 2 H, J = 6.7 Hz), 3.30 (m, 7 H), 2.81 (d, 3 H, J = 7.4 Hz), 2.05 (m, 5 H), 1.80 (m, 8 H), 1.19 (m, 2 H) | −0.008 (0.52%, 365 nm) |
| 92 | | 1-(3-{2-[3-(6-methoxypyridin-2-yl)pyrrolidin-1-yl]ethyl}pyridin-2-yl)piperidin-2-one | 381 | — | |
| 93 | 1.oxalic acid | 1-(3-{2-[3-(6-methoxypyridin-2-yl)pyrrolidin-1-yl]ethyl}pyridin-2-yl)piperidin-2-one oxalate | 381 | 1H 1.03 s 6.84 1H 2.68 d 4.05 d 0.68 1H 2.88 s 1.32 1H 3.12 m 2.15 1H 3.58 m 2.30 1H 4.32 M 32.10 1H 7.47 d 1.07 d 8.18 1H 7.71 d 1.05 d 7.13 1H 8.14 dd 1.08 d 6.97 1H 4.86 1H 8.29 s 1.55 1H 8.44 t 1.05 t 7.65 1H 8.64 d 1.00 d 7.15 1H 9.18 d 1.00 d 3.53 | |
| 94 | 1.oxalic acid | 1-[3-(2-{3-[6-(propan-2-yloxy)pyridin-2-yl]pyrrolidin-1-yl}ethyl)pyridin-2-yl]piperidin-2-one oxalate | 409 | 9.21 (d, J = 4.5 Hz, 1 H), 8.66 (d, J = 7.5 Hz, 1 H), 8.43 (t, J = 7.8 Hz, 1 H), 8.17 (dd, J1 = 7.5 Hz, J2 = 4.8 Hz, 1 H), 7.69 (d, J = 7.2 Hz, 1 H), 7.42 (d, J = 8.2 Hz, 1 H), 6.05 (m, 1 H), 4.65 (m, 1 H), 4.54 (m, 1 H), 4.46 (m, 1 H), 4.23 (m, 6 H), 3.64 (m, 2 H), 3.31 (m, 1 H), 3.17 (m, 2 H), 2.94 (m, 1 H), 2.66 (m, 4 H), 2.08 (d, J = 6.1 Hz, 6 H) | |
| 95 | 1.oxalic acid | 1-(3-{2-[(3R)-3-(2,2,2-trifluoroethyl)pyrrolidin-1-yl]ethyl}pyridin-2-yl)piperidin-2-one oxalate | 356 | (DMSO) 8.39 (m, 1 H), 7.83 (m, 1 H), 7.35 (m, 1 H), 3.85 (m, 1 H), 3.47 (m, 1 H), 3.28 (m, 5 H), 2.97 (m, 1 H), 2.80 (m, 2 H), 2.56 (m, 3 H), 2.33 (m, 1 H), 2.18 (m, 1 H), 1.88 (m, 4 H), 1.72 (m, 1 H) | |
| 96 | 1.oxalic acid | 6-(1-{2-[2-(2-oxopiperidin-1-yl)pyridin-3-yl]ethyl}pyrrolidin-3-yl)pyridine-2-carbonitrile oxalate | 376 | 9.21 (dd, J1 = 4.4 Hz, J2 = 1.1 Hz, 1 H), 8.86 (t, J = 7.8 Hz, 1 H), 8.77 (m, 1 H), 8.66 (m, 1 H), 8.56 (d, J = 7.9 Hz, 1 H), 8.17 (dd, J1 = 7.6 Hz, J2 = 4.8 Hz, 1 H), 4.62 (m, 4 H), 4.14 (m, 6 H), 3.65 (m, 2 H), 3.13 (m, 3 H), 2.92 (m, 2 H), 2.66 (m, 4 H) | |
| 97 | 1.oxalic acid | 1-(3-{2-[3-(3-fluoropyridin-2-yl)pyrrolidin-1-yl]ethyl}pyridin-2-yl)piperidin-2-one oxalate | 369 | 9.22 (dd, J1 = 8.4 Hz, J2 = 4.0 Hz, 2 H), 8.66 (d, J = 7.3 Hz, 1 H), 8.54 (m, 1 H), 8.24 (m, 1 H), 8.18 (m, 1 H), 4.78 (m, 2 H), 4.66 (m, 2 H), 4.49 (m, 1 H), 4.14 (m, 6 H), 3.64 (m, 2 H), 3.16 (m, 3 H), 2.98 (m, 1 H) | |
| 98 | | 1-[3-(2-{3-[6-(trifluoromethyl)pyridin-2-yl]pyrrolidin-1-yl}ethyl)pyridin-2-yl]piperidin-2-one | 419 | — | |
| 99 | | 1-[3-(2-{3-[(5-fluoropyridin-2-yl)oxy]azetidin-1-yl}ethyl)pyridin-2-yl]piperidin-2-one | 371 | 8.32 (m, 1 H), 8.08 (m, 1 H), 7.74 (m, 1 H), 7.67 (m, 1 H), 7.27 (m, 1 H), 6.86 (m, 1 H), 5.03 (m, 1 H), 3.81 (m, 1 H), 3.64 (m, 2 H), 3.28 (s, 1 H), 2.94 (m, 2 H), 2.61 (m, 2 H), 2.34 (m, 4 H), 1.83 (m, 4 H). | |
| 100 | 1.oxalic acid | 1-(3-{2-[3-(4-fluorophenoxy)azetidin-1-yl]ethyl}pyridin-2-yl)piperidin-2-one oxalate | 370 | 8.40 (m, 1 H), 7.85 (m, 1 H), 7.35 (m, 1 H), 7.15 (m, 2 H), 6.90 (m, 2 H), 4.96 (m, 1 H), 4.33 (s, 2 H), 3.82 (m, 3 H), 3.36 (m, 1 H), 3.22 (m, 2 H), 2.65 (m, 2 H), 2.30 (m, 1 H), 2.09 (m, 1 H), 1.85 (m, 4 H) | |
| 101 | 1.oxalic acid | 1-(3-{2-[3-(2-fluorophenoxy)azetidin-1-yl]ethyl}pyridin-2-yl)piperidin-2-one oxalate | 370 | 9.18 (m, 1 H), 8.64 (m, 1 H), 8.18 (m, 1 H), 8.07 (m, 1 H), 7.94 (m, 1 H), 7.79 (m, 2 H), 5.83 (m, 1 H), 5.15 (m, 3 H), 4.65 (s, 3 H), 4.15 (m, 1 H), 3.99 (m, 2 H), 3.43 (m, 2 H), 3.14 (m, 1 H), 2.64 (m, 4 H) | |
| 102 | 1.oxalic acid | (−)-1-(3-{2-[3-(pyridin-2-yl)pyrrolidin-1-yl]ethyl}pyridin-2-yl)piperidin-2-one oxalate | 351 | (DMSO) 8.55 (m, 1 H), 8.40 (m, 1 H), 7.87 (m, 1 H), 7.77 (m, 1 H), 7.40 (m, 2 H), 7.29 (m, 1 H), 3.88 (m, 1 H), 3.73 (m, 2 H), 3.39 (m, 6 H), 2.86 (m, 2 H), 2.56 (s, 1 H), 2.37 (m, 2 H), 2.13 (m, 1 H), 1.84 (m, 4 H) | −0.144 (0.5%) |

TABLE I-continued

Physical Characterization of Example Compounds.

| n° | ADDUCT | IUPAC_NAME | LC-MS (MH+) | NMR description (CDCl$_3$ otherwise specified) | αD (589 nm) |
|---|---|---|---|---|---|
| 103 | | 1-(3-{2-[3-(6-methylpyridin-2-yl)pyrrolidin-1-yl]ethyl}pyridin-2-yl)piperidin-2-one | 365 | 8.31 (dd, J1 = 4.7 Hz, J2 = 1.5 Hz, 1 H), 7.78 (d, J = 7.6 Hz, 1 H), 7.53 (t, J = 7.7 Hz, 1 H), 7.27 (dd, J1 = 7.4 Hz, J2 = 4.8 Hz, 1 H), 7.02 (t, J = 6.5 Hz, 2 H), 3.81 (m, 1 H), 3.38 (m, 1 H), 2.94 (t, J = 8.3 Hz, 1 H), 2.71 (m, 1 H), 2.58 (m, 6 H), 2.36 (m, 5 H), 2.12 (m, 1 H), 1.88 (m, 5 H) | |
| 104 | 1.oxalic acid | 1-[3-(2-{3-[6-(1H-pyrazol-1-yl)pyridin-2-yl]pyrrolidin-1-yl}ethyl)pyridin-2-yl]piperidin-2-one oxalate | 417 | (DMSO) 8.75 (m, 1 H), 8.42 (m, 1 H), 8.00 (m, 1 H), 7.87 (m, 1 H), 7.81 (m, 2 H), 7.34 (m, 2 H), 6.60 (m, 1 H), 2.86 (m, 2 H), 2.34 (m, 1 H), 2.19 (m, 1 H), 1.83 (m, 4 H), 1.03 (m, 1 H), missing H are obscured by solvent (H2O) | |
| 105 | | 1-(3-{2-[3-(4-methoxypyrimidin-2-yl)pyrrolidin-1-yl]ethyl}pyridin-2-yl)piperidin-2-one | 382 | — | |
| 106 | | 1-[3-(2-{3-[6-(4-fluorophenyl)pyridin-2-yl]pyrrolidin-1-yl}ethyl)pyridin-2-yl]piperidin-2-one | 445 | — | |
| 107 | 1.oxalic acid | 1-[3-(2-{3-[6-(cyclobutyloxy)pyridin-2-yl]pyrrolidin-1-yl}ethyl)pyridin-2-yl]piperidin-2-one oxalate | 421 | (DMSO) 9.20 (m, 1 H), 8.66 (d, J = 7.0 Hz, 1 H), 8.45 (t, J = 7.8 Hz, 1 H), 8.17 (dd, J1 = 7.6 Hz, J2 = 4.8 Hz, 1 H), 7.72 (d, J = 7.2 Hz, 1 H), 7.45 (d, J = 8.2 Hz, 1 H), 5.91 (t, J = 7.4 Hz), 4.46 (m, 4 H), 4.15 (m, 7 H), 3.64 (m, 2 H), 3.18 (m, 4 H), 2.86 (m, 3 H), 2.62 (m, 5 H), 2.42 (d, J = 10.1 Hz, 1 H) | |
| 108 | | 1-[3-(2-{3-[6-(2,2,2-trifluoroethoxy)pyridin-2-yl]pyrrolidin-1-yl}ethyl)pyridin-2-yl]piperidin-2-one | 449 | — | |
| 109 | | 1-[3-(2-{3-[6-(difluoromethoxy)pyridin-2-yl]pyrrolidin-1-yl}ethyl)pyridin-2-yl]piperidin-2-one | 417 | — | |
| 110 | | 1-[3-{2-[3-(pyridin-2-yl)pyrrolidin-1-yl]ethyl}-5-(trifluoromethyl)pyridin-2-yl]piperidin-2-one | 419 | (DMSO) 9.55 (s, 1 H), 9.26 (d, 1 H, J = 4.4 Hz), 9.06 (s, 1 H), 8.46 (t, 1 H, J = 7.6 Hz), 8.04 (m, 1 H), 7.98 (m, 1 H), 4.69 (m, 0 H), 4.22 (m, 2 H), 3.77 (m, 1 H), 3.49 (m, 7 H), 3.17 (m, 2 H), 2.97 (m, 1 H), 2.72 (m, 5 H) | |
| 111 | 1.oxalic acid | 1-[3-{2-[3-(pyridin-2-yl)pyrrolidin-1-yl]ethyl}-5-(trifluoromethyl)pyridin-2-yl]piperidin-2-one oxalate | 421 | (DMSO) 8.52 (d, 2H, J = 8.03 Hz), 8.39 (d, 2H, J = 8.03 Hz), 8.35 (s, 1H), 4.54 (s, 3H), 2.62 (m, 3H), 4.44 (m, 2H), 4.33 (m, 2H), 4.17 (broad m, 2H), 3.98 (m, 2H), 3.38 (t, 2H), 3.18 (m, 2H), 2.82 (m, 1H), 2.62 (m, 3H), other signals masked by solvent peaks | |
| 112 | | 1-(5-fluoro-3-{2-[3-(pyridin-2-yl)pyrrolidin-1-yl]ethyl}pyridin-2-yl)piperidin-2-one (80/20 mixture of enantiomers) | 369 | 9.27 (m, 1 H), 9.13 (d, 1 H, J = 2.9 Hz), 8.61 (d, 1 H, J = 9.3 Hz), 8.47 (td, 1 H, J = 7.7, 1.8 Hz), 8.07 (d, 1 H, J = 7.9 Hz), 7.99 (m, 1 H), 4.58 (m, 1 H), 4.24 (dd, 1 H, J = 9.5, 7.4 Hz), 3.79 (t, 1 H, J = 8.4 Hz), 3.43 (m, 6 H), 3.15 (d, 3 H, J = 14.8 Hz), 2.96 (dd, 1 H, J = 2.4, 1.1 Hz), 2.79 (m, 1 H), 2.66 (m, 5 H) | |

Example 20

[$^3$H]-5-Carboxytryptamine (5-CT) Binding Assay

Cell culture conditions and membrane preparation:

HEK293 Flp-In cells stably expressing human 5-HT$_{7D}$ receptor were generated in-house. Cells were subcultured in DMEM supplemented with 10% dialyzed FBS, 100 IU/ml penicillin, 100 µg/ml streptomycin and 200 µg/ml hygromycin. Cells were grown at 37° C. in a humidified atmosphere containing 5% CO$_2$. Membrane preparations were performed as described in Gillard et al., Eur. J. Pharmacol. (2006) 536, 102-108.

[$^3$H]-5-Carboxytryptamine (5-CT) Binding Assay:

The affinity of compounds for human 5-HT$_{7D}$ receptors was measured in a competition assay against [$^3$H]5-CT. This binding assay was adapted from Plassat et al. (1993). Briefly, membranes of HEK293 Flp-In cells expressing human 5-HT$_{7D}$ receptors (1-5 µg proteins per assay) were incubated at 25° C. for 180 min in 0.2 ml of a 50 mM Tris-HCl buffer (pH 7.4) containing 2 mM MgCl$_2$, 0.3-0.4 nM [$^3$H]5-CT and increasing concentrations of test compounds. The non-specific binding (NSB) was defined as the residual binding observed in the presence of 10 µM serotonin (5-HT). Membrane-bound and free radioligand were separated by rapid filtration through glass fiber filters presoaked in 0.1% polyethylenimine. Samples and filters were rinsed with ice-cold 50 mM Tris-HCl buffer (pH 7.4). Radioactivity trapped onto the filters was counted by liquid scintillation in a β-counter.

Compounds of formula I according to the invention show pKi values of at least 7.0.

Example 21

Measurement of Intracellular cAMP Concentration

The antagonism of test compounds on human 5-HT$_{7D}$ was assessed in a cAMP assay by measuring the rightward shifts of a concentration-response curve of 5-CT and the decrease in 5-CT maximal effect. Briefly, human 5-HT$_{7D}$ HEK293 Flp-In cells were preincubated at 750 cells per well for 60 min at 25° C. in 40 μl of HBSS buffer (pH 7.4) containing 20 nM HEPES, 0.1 mM IBMX and test compound. 5-CT was added at increasing concentrations and samples were incubated for another 60 min. Termination of the incubation and measurement of cAMP levels by HTRF were performed according to the guidelines provided with the kit (HTRF cAMP dynamic kit—62AM2PEC, CisBio International, France). Reference 5-HT$_7$ antagonist compound was mianserin.

Best compounds of formula I according to the invention have an unsurmontable effect, i.e. they inhibit the maximum effect induced by 5-CT.

Example 22

Dural Extravasation Model of Migraine

In the established model of dural extravasation, a compound-induced reduction of plasma protein extravasation into the dura is thought to be predictive of activity in the dural inflammation observed in migraine (Johnson, Neuroreport, 1997, 8, 2237-2240). Sprague-dawley rats (280-350 g) are anesthetized (pentobarbital 60 mg/kg i.p.), the femoral vein is then catheterized (PE 50 ID 0.58 mm, OD 0.965 mm) for Fluorescein isothiocyanate-bovine serum albumin (FITC-BSA) infusion and drug injection, and a tracheotomy is performed to ease breathing. The rat body temperature is maintained at 37° C.

The rat is then placed on a stereotaxic frame (Kopf instruments); the anterio-prosteriority reference (0) is taken at the interear bar. Following a midline sagital scalp incision, two craniotomies are performed manually (with a 2.2 mm strawberry shape manual probe; position: +5.4 mm from interear line, +3.8 mm from the middle suture). Two stimulating electrodes (A-M Systems Stainless steel insulated electrodes 0.10 diameter, 12 MΩ, inclination 8°, width between the electrodes: 1.6 mm) are then introduced in the left trigeminal ganglia (9.1 mm depth from the surface of the skull). The position is confirmed by the blink of the left eye following stimulation (1 pulse 60 μA).

The test compound is administered intravenously (1 ml/kg); Approximately 5 min post injection, FITC-BSA (Sigma A9771 prepared at 50 mg/kg in phosphate buffer solution Sigma P4417) is perfused (0.3 ml/2 min) via the femoral vein catheter.

At the end of the perfusion, the trigeminal ganglia is stimulated electrically (60 μA, 200 ms, 4 Hz) for 3 min.

Alternatively, the compound is dosed orally before anaesthesia approximately 45 min before electrical stimulation as described above.

Immediately following the stimulation, the rat are killed by exsanguination, the top of the skull is removed, and the left (ipsilateral to the stimulation) and right (contralateral to the stimulation) dura maters are collected and placed in filtered water then on microscope slides, and let to dry (30° protected from the light, minimum 3 h).

The electrode position in the trigeminal ganglia (Anterio-posterior and dorso/ventral) is verified under microscope (×16).

The level of fluorescence in dura maters ipsi- and contralateral to the trigeminal ganglia stimulation is quantified with a digital camera (Hamamatsu C4742-98 filter for FITC objective Nikon 2.8×) and analysis software (WIT5.3, Logical vision).

Preferred compounds are those effectively preventing fluorescence ipsilateral to the trigeminal ganglia stimulation and therefore preventing extravasation.

The invention claimed is:

1. A 2-Oxo-piperidinyl compound of the form according to formula I, or a geometrical isomer, enantiomer, diastereomer or mixture, or a pharmaceutically acceptable salt thereof, (I)

wherein

X is either CH or N; Y is either —NR$^4$— or —CH=CH—; with the proviso that X is N when Y is —NR$^4$—;

n is an integer selected from 1, 2 or 3; m is 1 or 2;

R$^1$ is a substituted or unsubstituted C$_{1-6}$ alkyl, a substituted or unsubstituted aryl, a substituted or unsubstituted heterocycle, a substituted or unsubstituted C$_{3-8}$ cycloalkyl; or R$^1$ is a —O—R$^2$ moiety;

R$^2$ is a substituted or unsubstituted C$_{1-6}$ alkyl, a substituted or unsubstituted aryl or a substituted or unsubstituted heteroaryl;

R$^3$ is hydrogen, substituted or unsubstituted C$_{1-4}$ alkyl or halogen; and

R$^4$ is hydrogen or C$_{1-4}$ alkyl.

2. The compound according to claim 1 having formula I-A, (I-A)

wherein

X is either CH or N;

n is an integer selected from 1, 2 or 3; m is 1 or 2;

R$^1$ is a substituted or unsubstituted C$_{1-6}$ alkyl, a substituted or unsubstituted aryl, a substituted or unsubstituted heterocycle, a substituted or unsubstituted C$_{3-8}$ cycloalkyl; or R$^1$ is a —O—R$^2$ moiety whereby R$^2$ is a substituted or unsubstituted C$_{1-6}$ alkyl, a substituted or unsubstituted aryl or a substituted or unsubstituted heteroaryl; and R$^3$ is hydrogen, substituted or unsubstituted C$_{1-4}$ alkyl or halogen.

3. The compound according to claim 1 having formula I-B,

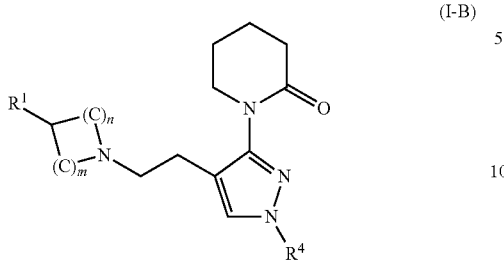

(I-B)

wherein n is an integer selected from 1, 2 or 3; m is 1 or 2;

$R^1$ is a substituted or unsubstituted $C_{1-6}$ alkyl, a substituted or unsubstituted aryl, a substituted or unsubstituted heterocycle, a substituted or unsubstituted $C_{3-8}$ cycloalkyl; or $R^1$ is a —O—$R^2$ moiety; whereby $R^2$ is a substituted or unsubstituted $C_{1-6}$ alkyl, a substituted or unsubstituted aryl or a substituted or unsubstituted heteroaryl; and $R^4$ is hydrogen or $C_{1-4}$ alkyl.

4. The compound according to claim 1, wherein $R^1$ is benzyl, 2-bromobenzyl, tert-butyl, 2-methylpropyl, 2-fluoro-2-methylpropyl, 2-chloro-2,2-difluoroethyl, 2-oxo-2-(pyrrolidin-1-yl)ethyl, 2,2,2-trifluoroethyl, propyl, phenyl, 2-carbamoylphenyl, 2-chlorophenyl, 3-chlorophenyl, 4-chlorophenyl, 2-cyanophenyl, 3-cyanophenyl, 4-cyanophenyl, 3,4-difluorophenyl, 2-fluorophenyl, 3-fluorophenyl, 4-fluorophenyl, 2-hydroxyphenyl, 2-methoxyphenyl, 3-methoxyphenyl, 4-methoxy-phenyl, 2-(methylcarbamoyl)phenyl, 2-(3-methyl-1,2,4-oxadiazol-5-yl)phenyl, 2-(pyrrolidin-1-ylcarbonyl)phenyl, 2-(trifluoromethyl)phenyl, 3-(trifluoromethyl)phenyl, 4-(trifluoromethyl)phenyl, cyclohexyl, 4,4-difluorocyclohexyl, pyridin-2-yl, 6-cyanopyridin-2-yl, 3-fluoropyridin-2-yl, 5-fluoropyridin-2-yl, 6-methoxypyridin-2-yl, 6-methylpyridin-2-yl, 6-(4-fluorophenyl)pyridin-2-yl, 6-(propan-2-yloxy)pyridin-2-yl, 6-(1H-pyrazol-1-yl)pyridin-2-yl, 6-trifluoromethylpyridin-2-yl, 6-(cyclobutyloxy)pyridin-2-yl, 6-(difluoromethoxy)pyridin-2-yl, 6-(2,2,2-trifluoroethoxy)pyridin-2-yl, pyridin-3-yl, 2-fluoropyridin-3-yl, pyridin-4-yl, 4-methoxypyrimidin-2-yl, 4-methyl-1,3-thiazol-2-yl, 4-methyl-1,3-thiazol-5-yl, 1-acetylpiperidin-2-yl, tetrahydro-2H-pyran-3-yl, tetrahydro-2H-pyran-4-yl, tetrahydrofuran-2-yl.

5. The compound according to claim 1 having formula I-C,

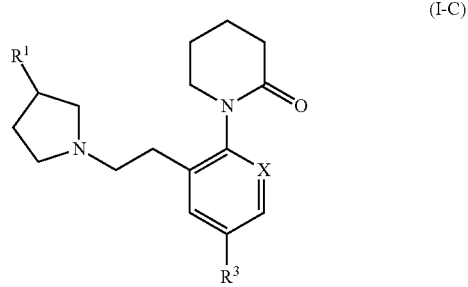

(I-C)

wherein

X is either CH or N;

$R^1$ is a substituted or unsubstituted $C_{1-4}$ alkyl, a substituted or unsubstituted aryl, a substituted or unsubstituted heteroaryl, a substituted or unsubstituted heterocycloalkyl, a substituted or unsubstituted $C_{3-6}$ cycloalkyl; or $R^1$ is a —O—$R^2$ moiety;

$R^2$ is a substituted or unsubstituted $C_{1-4}$-alkyl aryl, a substituted or unsubstituted aryl, or a substituted or unsubstituted heteroaryl; and $R^3$ is hydrogen, substituted or unsubstituted $C_{1-4}$ alkyl or halogen.

6. The compound according to claim 1 having formula I-D,

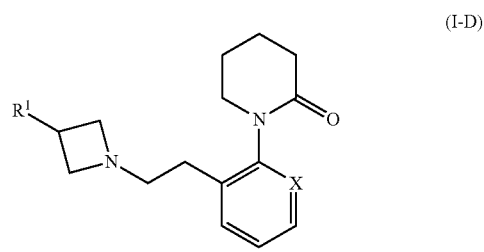

(I-D)

wherein

X is either CH or N;

$R^1$ is a substituted or unsubstituted $C_{1-4}$ alkyl, a substituted or unsubstituted aryl, a substituted or unsubstituted heteroaryl, a substituted or unsubstituted heterocycloalkyl, a substituted or unsubstituted $C_{3-6}$ cycloalkyl; or $R^1$ is a —O—$R^2$ moiety; and $R^2$ is a substituted or unsubstituted $C_{1-4}$-alkyl aryl, a substituted or unsubstituted aryl, or a substituted or unsubstituted heteroaryl.

7. The compound according to claim 1 having formula I-E,

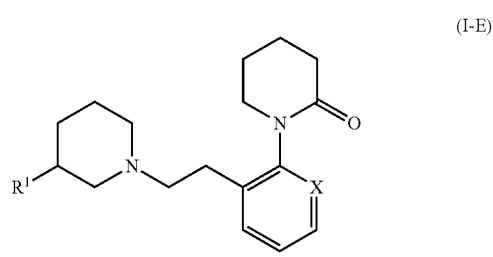

(I-E)

wherein

X is either CH or N;

$R^1$ is a substituted or unsubstituted $C_{1-4}$ alkyl, a substituted or unsubstituted phenyl, a substituted or unsubstituted pyridinyl, a substituted or unsubstituted pyrimidinyl, a substituted or unsubstituted thiazolyl, a substituted or unsubstituted piperidinyl, a substituted or unsubstituted tetrahydropyranyl, a substituted or unsubstituted tetrahydrofuranyl, a substituted or unsubstituted cyclohexyl; or $R^1$ is a —O—$R^2$ moiety; and $R^2$ is a substituted or unsubstituted benzyl, a substituted or unsubstituted phenyl, or a substituted or unsubstituted pyridinyl.

8. The compound according to claim 1 selected from the group comprising:

(+)-2-(1-{2-[2-(2-oxopiperidin-1-yl)phenyl]ethyl}pyrrolidin-3-yl)benzamide oxalate;

N-methyl-2-(1-{2-[2-(2-oxopiperidin-1-yl)phenyl]ethyl}pyrrolidin-3-yl)benzamide oxalate;

2-(1-{2-[2-(2-oxopiperidin-1-yl)phenyl]ethyl}pyrrolidin-3-yl)benzonitrile oxalate;
2-(1-{2-[2-(2-oxopiperidin-1-yl)phenyl]ethyl}piperidin-3-yl)benzamide oxalate;
1-[2-(2-{3-[2-(trifluoromethyl)phenyl]pyrrolidin-1-yl}ethyl)phenyl]piperidin-2-one oxalate;
1-(2-{2-[3-(2-methoxyphenyl)pyrrolidin-1-yl]ethyl}phenyl)piperidin-2-one oxalate;
1-(2-{2-[3-(3-methoxyphenyl)pyrrolidin-1-yl]ethyl}phenyl)piperidin-2-one oxalate;
1-(2-{2-[3-(4-methoxyphenyl)pyrrolidin-1-yl]ethyl}phenyl)piperidin-2-one oxalate;
1-(2-{2-[3-(2-fluorophenyl)pyrrolidin-1-yl]ethyl}phenyl)piperidin-2-one oxalate;
1-(2-{2-[3-(2-chlorophenyl)pyrrolidin-1-yl]ethyl}phenyl)piperidin-2-one oxalate;
1-[2-(2-{3-[2-(3-methyl-1,2,4-oxadiazol-5-yl)phenyl]pyrrolidin-1-yl}ethyl)phenyl]piperidin-2-one;
(+)-2-(1-{2-[2-(2-oxopiperidin-1-yl)phenyl]ethyl}pyrrolidin-3-yl)benzonitrile oxalate;
(−)-2-(1-{2-[2-(2-oxopiperidin-1-yl)phenyl]ethyl}pyrrolidin-3-yl)benzonitrile oxalate;
1-{2-[2-(3-phenylpyrrolidin-1-yl)ethyl]phenyl}piperidin-2-one;
3-(1-{2-[2-(2-oxopiperidin-1-yl)phenyl]ethyl}pyrrolidin-3-yl)benzonitrile oxalate;
4-(1-{2-[2-(2-oxopiperidin-1-yl)phenyl]ethyl}pyrrolidin-3-yl)benzonitrile oxalate;
(−)-1-[2-(2-{3-[2-(pyrrolidin-1-ylcarbonyl)phenyl]pyrrolidin-1-yl}ethyl)phenyl]piperidin-2-one;
1-(2-{2-[3-(2-methoxyphenyl)piperidin-1-yl]ethyl}phenyl)piperidin-2-one oxalate;
(+)-1-(2-{2-[3-(2-methoxyphenyl)pyrrolidin-1-yl]ethyl}phenyl)piperidin-2-one oxalate;
(−)-1-(2-{2-[3-(2-methoxyphenyl)pyrrolidin-1-yl]ethyl}phenyl)piperidin-2-one oxalate;
1-[2-(2-{3-[3-(trifluoromethyl)phenyl]pyrrolidin-1-yl}ethyl)phenyl]piperidin-2-one oxalate;
1-(2-{2-[3-(3-fluorophenyl)pyrrolidin-1-yl]ethyl}phenyl)piperidin-2-one oxalate;
1-{2-[2-(3-phenylazetidin-1-yl)ethyl]phenyl}piperidin-2-one oxalate;
1-(2-{2-[3-(3-fluorophenyl)piperidin-1-yl]ethyl}phenyl)piperidin-2-one oxalate;
1-(2-{2-[3-(3-methoxyphenyl)piperidin-1-yl]ethyl}phenyl)piperidin-2-one oxalate;
1-{2-[2-(3-phenylpiperidin-1-yl)ethyl]phenyl}piperidin-2-one oxalate;
1-(2-{2-[3-(4-chlorophenyl)pyrrolidin-1-yl]ethyl}phenyl)piperidin-2-one oxalate;
1-(2-{2-[3-(3-chlorophenyl)pyrrolidin-1-yl]ethyl}phenyl)piperidin-2-one oxalate;
1-(2-{2-[3-(benzyloxy)pyrrolidin-1-yl]ethyl}phenyl)piperidin-2-one oxalate;
1-(2-{2-[3-(4-fluorophenyl)azetidin-1-yl]ethyl}phenyl)piperidin-2-one oxalate;
3-(1-{2-[2-(2-oxopiperidin-1-yl)phenyl]ethyl}azetidin-3-yl)benzonitrile oxalate;
1-(2-{2-[3-(2-fluorophenyl)azetidin-1-yl]ethyl}phenyl)piperidin-2-one oxalate;
1-{2-[2-(3-cyclohexylpyrrolidin-1-yl)ethyl]phenyl}piperidin-2-one oxalate;
1-(2-{2-[3-(2-hydroxyphenyl)pyrrolidin-1-yl]ethyl}phenyl)piperidin-2-one oxalate;
1-(2-{2-[3-(pyridin-2-yl)pyrrolidin-1-yl]ethyl}phenyl)piperidin-2-one dioxalate;
1-(2-{2-[3-(pyridin-2-yl)pyrrolidin-1-yl]ethyl}phenyl)piperidin-2-one;
1-(2-{2-[3-(4-fluorophenyl)pyrrolidin-1-yl]ethyl}phenyl)piperidin-2-one oxalate;
1-(2-{2-[(3R)-3-(2,2,2-trifluoroethyl)pyrrolidin-1-yl]ethyl}phenyl)piperidin-2-one oxalate;
1-(2-{2-[(3S)-3-(2,2,2-trifluoroethyl)pyrrolidin-1-yl]ethyl}phenyl)piperidin-2-one trifluoroacetate;
1-(2-{2-[(3S)-3-(2,2,2-trifluoroethyl)pyrrolidin-1-yl]ethyl}phenyl)piperidin-2-one oxalate;
4-(1-{2-[2-(2-oxopiperidin-1-yl)phenyl]ethyl}piperidin-3-yl)benzonitrile oxalate;
(−)-4-(1-{2-[2-(2-oxopiperidin-1-yl)phenyl]ethyl}pyrrolidin-3-yl)benzonitrile oxalate;
(+)-4-(1-{2-[2-(2-oxopiperidin-1-yl)phenyl]ethyl}pyrrolidin-3-yl)benzonitrile oxalate;
1-(2-{2-[3-(2-methoxyphenyl)azetidin-1-yl]ethyl}phenyl)piperidin-2-one oxalate;
1-(2-{2-[3-(3-fluorophenyl)azetidin-1-yl]ethyl}phenyl)piperidin-2-one oxalate;
1-(2-{2-[3-(3,4-difluorophenyl)pyrrolidin-1-yl]ethyl}phenyl)piperidin-2-one oxalate;
1-(2-{2-[3-(3-methoxyphenyl)azetidin-1-yl]ethyl}phenyl)piperidin-2-one oxalate;
1-{2-[2-(3-benzylpyrrolidin-1-yl)ethyl]phenyl}piperidin-2-one oxalate;
1-(2-{2-[3-(2-methoxyphenoxy)pyrrolidin-1-yl]ethyl}phenyl)piperidin-2-one oxalate;
4-[(1-{2-[2-(2-oxopiperidin-1-yl)phenyl]ethyl}pyrrolidin-3-yl)oxy]benzonitrile;
1-(2-{2-[3-(tetrahydro-2H-pyran-4-yl)pyrrolidin-1-yl]ethyl}phenyl)piperidin-2-one oxalate;
1-{2-[2-(3-benzylazetidin-1-yl)ethyl]phenyl}piperidin-2-one;
1-(2-{2-[3-(pyridin-3-yl)pyrrolidin-1-yl]ethyl}phenyl)piperidin-2-one;
1-(2-{2-[3-(4,4-difluorocyclohexyl)pyrrolidin-1-yl]ethyl}phenyl)piperidin-2-one trifluoroacetate;
4-[(1-{2-[2-(2-oxopiperidin-1-yl)phenyl]ethyl}azetidin-3-yl)oxy]benzonitrile oxalate;
1-(2-{2-[3-(2-methylpropyl)pyrrolidin-1-yl]ethyl}phenyl)piperidin-2-one trifluoroacetate;
1-{2-[2-(3-propylpyrrolidin-1-yl)ethyl]phenyl}piperidin-2-one trifluoroacetate;
3-[(1-{2-[2-(2-oxopiperidin-1-yl)phenyl]ethyl}azetidin-3-yl)oxy]benzonitrile;
2-[(1-{2-[2-(2-oxopiperidin-1-yl)phenyl]ethyl}azetidin-3-yl)oxy]benzonitrile;
1-(2-{2-[3-(4-fluorophenoxy)azetidin-1-yl]ethyl}phenyl)piperidin-2-one;
1-(2-{2-[3-(3-methoxyphenoxy)azetidin-1-yl]ethyl}phenyl)piperidin-2-one;
1-(2-{2-[3-(2-bromobenzyl)azetidin-1-yl]ethyl}phenyl)piperidin-2-one;
4-(1-{2-[2-(2-oxopiperidin-1-yl)pyridin-3-yl]ethyl}pyrrolidin-3-yl)benzonitrile;
1-(2-{2-[3-(4-methyl-1,3-thiazol-5-yl)pyrrolidin-1-yl]ethyl}phenyl)piperidin-2-one;
1-(2-{2-[3-(5-bromo-2-methoxyphenoxy)azetidin-1-yl]ethyl}phenyl)piperidin-2-one oxalate;
1-{2-[2-(3-phenoxyazetidin-1-yl)ethyl]phenyl}piperidin-2-one oxalate;
1-{2-[2-(3-tert-butylpyrrolidin-1-yl)ethyl]phenyl}piperidin-2-one;
1-(2-{2-[3-(2-methoxyphenoxy)azetidin-1-yl]ethyl}phenyl)piperidin-2-one oxalate;

1-(2-{2-[3-(2-chloro-2,2-difluoroethyl)pyrrolidin-1-yl]
ethyl}phenyl)piperidin-2-one;
1-(3-{2-[3-(pyridin-2-yl)pyrrolidin-1-yl]ethyl}pyridin-2-
yl)piperidin-2-one;
1-(3-{2-[3-(pyridin-2-yl)pyrrolidin-1-yl]ethyl}pyridin-2-
yl)piperidin-2-one oxalate;
1-(2-{2-[3-(1-acetylpiperidin-2-yl)pyrrolidin-1-yl]
ethyl}phenyl)piperidin-2-one;
1-(2-{2-[3-(pyridin-4-yl)pyrrolidin-1-yl]ethyl}phenyl)piperidin-2-one;
1-(2-{2-[3-(2-fluoropyridin-3-yl)pyrrolidin-1-yl]
ethyl}phenyl)piperidin-2-one;
1-(2-{2-[3-(tetrahydrofuran-2-yl)pyrrolidin-1-yl]
ethyl}phenyl)piperidin-2-one;
1-(2-{2-[3-(tetrahydrofuran-2-yl)pyrrolidin-1-yl]
ethyl}phenyl)piperidin-2-one oxalate;
(+)-1-(2-{2-[3-(tetrahydro-2H-pyran-4-yl)pyrrolidin-1-
yl]ethyl}phenyl)piperidin-2-one trifluoroacetate;
(+)-1-(2-{2-[3-(tetrahydro-2H-pyran-4-yl)pyrrolidin-1-
yl]ethyl}phenyl)piperidin-2-one oxalate;
1-(3-{2-[(3S)-3-(2,2,2-trifluoroethyl)pyrrolidin-1-yl]
ethyl}pyridin-2-yl)piperidin-2-one oxalate;
1-(3-{2-[(3S)-3-(2,2,2-trifluoroethyl)pyrrolidin-1-yl]
ethyl}pyridin-2-yl)piperidin-2-one;
1-(2-{2-[3-(tetrahydro-2H-pyran-3-yl)pyrrolidin-1-yl]
ethyl}phenyl)piperidin-2-one trifluoroacetate;
1-(2-{2-[3-(6-methoxypyridin-2-yl)pyrrolidin-1-yl]
ethyl}phenyl)piperidin-2-one;
1-(2-{2-[3-(5-fluoropyridin-2-yl)pyrrolidin-1-yl]
ethyl}phenyl)piperidin-2-one;
1-(2-{2-[3-(3-fluoropyridin-2-yl)pyrrolidin-1-yl]
ethyl}phenyl)piperidin-2-one;
1-(2-{2-[3-(2-fluoro-2-methylpropyl)pyrrolidin-1-yl]
ethyl}phenyl)piperidin-2-one;
1-[2-(2-{3-[2-oxo-2-(pyrrolidin-1-yl)ethyl]pyrrolidin-1-
yl}ethyl)phenyl]piperidin-2-one;
1-(2-{2-[3-(4-methyl-1,3-thiazol-2-yl)pyrrolidin-1-yl]
ethyl}phenyl)piperidin-2-one oxalate;
1-(3-{2-[3-(5-fluoropyridin-2-yl)pyrrolidin-1-yl]
ethyl}pyridin-2-yl)piperidin-2-one;
1-(3-{2-[3-(pyridin-2-yl)pyrrolidin-1-yl]ethyl}pyridin-2-
yl)piperidin-2-one oxalate, isomer A;
(+)-1-(3-{2-[3-(4,4-difluorocyclohexyl)pyrrolidin-1-yl]
ethyl}pyridin-2-yl)piperidin-2-one oxalate;
(−)-1-(3-{2-[3-(4,4-difluorocyclohexyl)pyrrolidin-1-yl]
ethyl}pyridin-2-yl)piperidin-2-one oxalate;
1-(3-{2-[3-(6-methoxypyridin-2-yl)pyrrolidin-1-yl]
ethyl}pyridin-2-yl)piperidin-2-one;
1-(3-{2-[3-(6-methoxypyridin-2-yl)pyrrolidin-1-yl]
ethyl}pyridin-2-yl)piperidin-2-one oxalate;
1-[3-(2-{3-[6-(propan-2-yloxy)pyridin-2-yl]pyrrolidin-1-
yl}ethyl)pyridin-2-yl]piperidin-2-one oxalate;
1-(3-{2-[(3R)-3-(2,2,2-trifluoroethyl)pyrrolidin-1-yl]
ethyl}pyridin-2-yl)piperidin-2-one oxalate;
6-(1-{2-[2-(2-oxopiperidin-1-yl)pyridin-3-yl]
ethyl}pyrrolidin-3-yl)pyridine-2-carbonitrile oxalate;
1-(3-{2-[3-(3-fluoropyridin-2-yl)pyrrolidin-1-yl]
ethyl}pyridin-2-yl)piperidin-2-one oxalate;
1-[3-(2-{3-[6-(trifluoromethyl)pyridin-2-yl]pyrrolidin-1-
yl}ethyl)pyridin-2-yl]piperidin-2-one;
1-[3-(2-{3-[(5-fluoropyridin-2-yl)oxy]azetidin-1-
yl}ethyl)pyridin-2-yl]piperidin-2-one;
1-(3-{2-[3-(4-fluorophenoxy)azetidin-1-yl]ethyl}pyridin-
2-yl)piperidin-2-one oxalate;
1-(3-{2-[3-(2-fluorophenoxy)azetidin-1-yl]ethyl}pyridin-
2-yl)piperidin-2-one oxalate;
(−)-1-(3-{2-[3-(pyridin-2-yl)pyrrolidin-1-yl]
ethyl}pyridin-2-yl)piperidin-2-one oxalate;
1-(3-{2-[3-(6-methylpyridin-2-yl)pyrrolidin-1-yl]
ethyl}pyridin-2-yl)piperidin-2-one;
1-[3-(2-{3-[6-(1H-pyrazol-1-yl)pyridin-2-yl]pyrrolidin-
1-yl}ethyl)pyridin-2-yl]piperidin-2-one oxalate;
1-(3-{2-[3-(4-methoxypyrimidin-2-yl)pyrrolidin-1-yl]
ethyl}pyridin-2-yl)piperidin-2-one;
1-[3-(2-{3-[6-(4-fluorophenyl)pyridin-2-yl]pyrrolidin-1-
yl}ethyl)pyridin-2-yl]piperidin-2-one;
1-[3-(2-{3-[6-(cyclobutyloxy)pyridin-2-yl]pyrrolidin-1-
yl}ethyl)pyridin-2-yl]piperidin-2-one oxalate;
1-[3-(2-{3-[6-(2,2,2-trifluoroethoxy)pyridin-2-yl]pyrrolidin-1-yl]ethyl}pyridin-2-yl]piperidin-2-one;
1-[3-(2-{3-[6-(difluoromethoxy)pyridin-2-yl]pyrrolidin-
1-yl}ethyl)pyridin-2-yl]piperidin-2-one;   1-[3-{2-[3-
(pyridin-2-yl)pyrrolidin-1-yl]ethyl}-5-(trifluoromethyl)pyridin-2-yl]piperidin-2-one;
1-[3-{2-[3-(pyridin-2-yl)pyrrolidin-1-yl]ethyl}-5-(trifluoromethyl)pyridin-2-yl]piperidin-2-one oxalate; and
1-(5-fluoro-3-{2-[3-(pyridin-2-yl)pyrrolidin-1-yl]
ethyl}pyridin-2-yl)piperidin-2-one.

9. A pharmaceutical composition comprising a compound according to claim 1 in combination with a pharmaceutically acceptable diluent or carrier.

10. A method of treating migraine in a subject comprising administering to the subject a therapeutically effective amount of a compound according to claim 1.

11. The compound according to claim 7 wherein $R^2$ is benzyl or substituted or unsubstituted phenyl.

* * * * *